United States Patent
Dimitrov et al.

(10) Patent No.: US 10,472,412 B2
(45) Date of Patent: Nov. 12, 2019

(54) BISPECIFIC MULTIVALENT FUSION PROTEINS

(71) Applicants: The United States of America, as represented by the Secretary, Department of Health and Human Services, Bethesda, MD (US); Fudan University, Shanghai (CN)

(72) Inventors: Dimiter S. Dimitrov, Frederick, MD (US); Weizao Chen, Frederick, MD (US); Tianlei Ying, Shanghai (CN)

(73) Assignees: The United States of America, as represented by the Secretary, Department of Health and Human Services, Bethesda, MD (US); Fudan University, Shanghai (CN)

( * ) Notice: Subject to any disclaimer, the term of this patent is extended or adjusted under 35 U.S.C. 154(b) by 14 days.

(21) Appl. No.: 15/561,268

(22) PCT Filed: Dec. 16, 2015

(86) PCT No.: PCT/US2015/066131
§ 371 (c)(1),
(2) Date: Sep. 25, 2017

(87) PCT Pub. No.: WO2016/153572
PCT Pub. Date: Sep. 29, 2016

(65) Prior Publication Data
US 2018/0118815 A1    May 3, 2018

Related U.S. Application Data

(60) Provisional application No. 62/138,003, filed on Mar. 25, 2015.

(51) Int. Cl.
*A61K 39/21* (2006.01)
*C07K 16/10* (2006.01)
(Continued)

(52) U.S. Cl.
CPC ...... *C07K 16/1063* (2013.01); *A61K 47/6803* (2017.08); *A61P 31/18* (2018.01);
(Continued)

(58) Field of Classification Search
None
See application file for complete search history.

(56) References Cited

U.S. PATENT DOCUMENTS

| 8,911,728 B2 | 12/2014 | Dimitrov et al. |
| 2002/0164328 A1 | 11/2002 | Shinkawa et al. |

(Continued)

FOREIGN PATENT DOCUMENTS

| WO | WO 00/61739 A1 | 10/2000 |
| WO | WO 01/29246 A1 | 4/2001 |

(Continued)

OTHER PUBLICATIONS

Allaway et al., "Expression and characterization of CD4-IgG2, a novel heterotetramer that neutralizes primary HIV type 1 isolates," *AIDS Res. Hum. Retroviruses*, 11 (5), 533-539 (1995).
(Continued)

*Primary Examiner* — Janet L Andres
*Assistant Examiner* — Stuart W Snyder
(74) *Attorney, Agent, or Firm* — Leydig, Voit & Mayer, Ltd.

(57) ABSTRACT

The invention provides a construct comprising two or more fusion proteins of Formulas (I)-(IV): A-(optional linker)-C-(optional linker)-B (Formula I), B-(optional linker)-D-(optional linker)-E-(optional linker)-B (Formula II), A-(optional linker)-C (Formula III), and B-(optional linker)-D-(optional linker)-E (Formula IV), wherein A denotes an antibody or antibody fragment, B denotes a single domain CD4, C denotes an immunoglobulin light chain constant region D denotes an immunoglobulin heavy chain constant
(Continued)

region, and E denotes an Fc region or a portion thereof that is optionally defucosylated.

16 Claims, 23 Drawing Sheets

Specification includes a Sequence Listing.

(51) Int. Cl.
  *C07K 14/73* (2006.01)
  *A61K 47/68* (2017.01)
  *A61P 31/18* (2006.01)
  *A61K 38/00* (2006.01)
  *A61K 39/00* (2006.01)

(52) U.S. Cl.
  CPC ........ *C07K 14/70514* (2013.01); *A61K 38/00* (2013.01); *A61K 2039/505* (2013.01); *C07K 2317/14* (2013.01); *C07K 2317/21* (2013.01); *C07K 2317/31* (2013.01); *C07K 2317/35* (2013.01); *C07K 2317/41* (2013.01); *C07K 2317/515* (2013.01); *C07K 2317/522* (2013.01); *C07K 2317/526* (2013.01); *C07K 2317/53* (2013.01); *C07K 2317/569* (2013.01); *C07K 2317/72* (2013.01); *C07K 2317/732* (2013.01); *C07K 2317/76* (2013.01); *C07K 2317/90* (2013.01); *C07K 2317/92* (2013.01); *C07K 2317/94* (2013.01); *C07K 2319/00* (2013.01); *C07K 2319/30* (2013.01); *C07K 2319/32* (2013.01); *C07K 2319/33* (2013.01)

(56) References Cited

U.S. PATENT DOCUMENTS

| | | | |
|---|---|---|---|
| 2003/0115614 | A1 | 6/2003 | Kanda et al. |
| 2003/0157108 | A1 | 8/2003 | Presta |
| 2004/0093621 | A1 | 5/2004 | Shitara et al. |
| 2004/0109865 | A1 | 6/2004 | Niwa et al. |
| 2004/0110282 | A1 | 6/2004 | Kanda et al. |
| 2004/0110704 | A1 | 6/2004 | Yamane et al. |
| 2004/0132140 | A1 | 7/2004 | Satoh et al. |
| 2004/0220388 | A1 | 11/2004 | Mertens et al. |

FOREIGN PATENT DOCUMENTS

| | | | | |
|---|---|---|---|---|
| WO | WO 02/31140 | A1 | 4/2002 | |
| WO | WO 03/035835 | A2 | 5/2003 | |
| WO | WO 03/084570 | A1 | 10/2003 | |
| WO | WO 03/085107 | A1 | 10/2003 | |
| WO | WO 03/085119 | A1 | 10/2003 | |
| WO | WO 2004/056312 | A2 | 7/2004 | |
| WO | WO 2005/035586 | A1 | 4/2005 | |
| WO | WO 2005/035778 | A1 | 4/2005 | |
| WO | WO 2005/053742 | A1 | 6/2005 | |
| WO | WO 2006/089232 | A2 | 8/2006 | |
| WO | WO 2008/077546 | A1 | 7/2008 | |
| WO | WO 2011/146891 | A2 | 11/2011 | |
| WO | WO 2013/026831 | A1 | 2/2013 | |
| WO | WO 2014/150748 | A2 * | 9/2014 | ......... C07K 16/1063 |

OTHER PUBLICATIONS

Bardhi et al., "In Vivo control of HIV infection by a novel engineered bio-specific anti-HIV antibody-based fusion protein" *Keystone* meeting abstract (2015).
Bardhi et al., "Potent In Vivo cell-mediated elimination of HIV-1-infected cells mobilized by a gp120-bispecific and hexavalent broadly neutralizing fusion protein" *Journal of Virology*, Accepted Manuscript (Aug. 9, 2017) (56 pages).

Bournazos et al., "Broadly neutralizing anti-HIV-1 antibodies require Fc effector functions for in vivo activity," *Cell*, 158 (6), 1243-1253 (2014).
Chen et al., "Bifunctional fusion proteins of the human engineered antibody domain m36 with human soluble CD4 are potent inhibitors of diverse HIV-1 isolates," *Antiviral Res.*, 88 (1), 107-115 (2010).
Chen et al., "Construction of a large phage-displayed human antibody domain library with a scaffold based on a newly identified highly soluble, stable heavy chain variable domain," *J. Mol. Biol.*, 382 (3), 779-789 (2008) Author Manuscript.
Chen et al., "Engineered single human CD4 domains as potent HIV-1 inhibitors and components of vaccine immunogens," *J. Virol.*, 85 (18), 9395-9405 (2011).
Chen et al., "Exceptionally potent and broadly cross-reactive, bispecific multivalent HIV-1 inhibitors based on single human CD4 and antibody domains," *J. Virol.*, 88 (2), 1125-1139 (2014).
Chen et al., "A large human domain antibody library combining heavy and light chain CDR3 diversity," *Mol. Immunol.*, 47 (4), 912-921 (2010) Author Manuscript.
Chen et al., "Human domain antibodies to conserved sterically restricted regions on gp120 as exceptionally potent cross-reactive HIV-1 neutralizers," *Proc. Natl. Acad. Sci. USA*, 105 (44), 17121-17126 (2008).
Chen et al., "Improving the CH1-CK heterodimerization and pharmacokinetics of 4Dm2m, a novel potent CD4-antibody fusion protein against HIV-1" *mAbs*, 8(4), 761-774 (2016).
Dey et al., "Neutralization of human immunodeficiency virus type 1 by sCD4-17b, a single-chain chimeric protein, based on sequential interaction of gp120 with CD4 and coreceptor," *J. Virol.*, 77 (5), 2859-2865 (2003).
Feng et al. "Design, expression and characterization of a soluble single-chain functional human neonatal Fc receptor," *Protein Expr. Purif.*, 79 (1), 66-71 (2011) Author Manuscript.
Gardner et al., "AAV-expressed eCD4-Ig provides durable protection from multiple SHIV challenges," *Nature*, 519 (7541), 87-91 (2015) Author Manuscript.
International Preliminary Report on Patentability, Application No. PCT/US2015/066131, dated Sep. 26, 2017, 12 pages.
International Search Report, Application No. PCT/US2015/066131, dated Jun. 8, 2016, 11 pages.
Kanda et al., "Comparison of cell lines for stable production of fucose-negative antibodies with enhanced ADCC," *Biotechnol. Bioeng.*, 94 (4), 680-688 (2006).
Ko et al., "Enhanced neonatal Fc receptor function improves protection against primate SHIV infection," *Nature*, 514 (7524), 642-645 (2014) Author Manuscript.
Lagenaur et al., "sCD4-17b bifunctional protein: extremely broad and potent neutralization of HIV-1 Env pseudotyped viruses from genetically diverse primary isolates," *Retrovirology*, 7 (11), 1-13 (2010).
Lewis et al., "Role of Fc-mediated antibody function in protective immunity against HIV-1," *Immunology*, 142 (1), 46-57 (2014).
Moldt et al., "A nonfucosylated variant of the anti-HIV-1 monoclonal antibody b12 has enhanced FcγRIIIa-mediated antiviral activity in vitro but does not improve protection against mucosal SHIV challenge in macaques," *J. Virol.*, 86 (11), 6189-6196 (2012).
Muller et al., "The first constant domain (C(H)1 and C(L)) of an antibody used as heterodimerization domain for bispecific miniantibodies," *FEBS Lett.*, 422 (2), 259-264 (1998).
Niwa et al., "The current status and prospects of antibody engineering for therapeutic use: focus on glycoengineering technology," *J. Pharm. Sci.*, 104 (3), 930-941 (2015).
Okazaki et al., "Fucose depletion from human IgG1 oligosaccharide enhances binding enthalpy and association rate between IgG1 and FcgammaRIIIa," *J. Mol. Biol.*, 336 (5), 1239-1249 (2004).
Ripka et al., "Two Chinese hamster ovary glycosylation mutants affected in the conversion of GDP-mannose to GDP-fucose," *Arch. Biochem. Biophys.*, 249 (2), 533-545 (1986).
Rothlisberger et al., "Domain interactions in the Fab fragment: a comparative evaluation of the single-chain Fv and Fab format engineered with variable domains of different stability," *J. Mol. Biol.*, 347 (4), 773-89 (2005).

(56) References Cited

OTHER PUBLICATIONS

Rozan et al., "Single-domain antibody-based and linker-free bispecific antibodies targeting FcγRIII induce potent antitumor activity without recruiting regulatory T cells," *Mol. Cancer Ther.*, 12 (8), 1481-1491 (2013).

Schoonjans et al., "Fab chains as an efficient heterodimerization scaffold for the production of recombinant bispecific and trispecific antibody derivatives," *J. Immunol.*, 165 (12), 7050-7057 (2000).

West et al., "Evaluation of CD4-CD4i antibody architectures yields potent, broadly cross-reactive anti-human immunodeficiency virus reagents," *J. Virol.*, 84 (1), 261-269 (2010).

Written Opinion of the International Searching Authority, Application No. PCT/US2015/066131, dated Jun. 8, 2016, 10 pages.

Yamane-Ohnuki et al., "Establishment of FUT8 knockout Chinese hamster ovary cells: an ideal host cell line for producing completely defucosylated antibodies with enhanced antibody-dependent cellular cytotoxicity," *Biotech. Bioeng.*, 87 (5), 614-622 (2004).

Ying et al., "Engineered soluble monomeric IgG1 CH3 domain: generation, mechanisms of function, and implications for design of biological therapeutics," *J. Biol. Chem.*, 288 (35), 25154-25164 (2013).

Zalevsky et al., "Enhanced antibody half-life improves in vivo activity," *Nat. Biotechnol.*, 28 (2), 157-159 (2010) Author Manuscript.

Zhu et al., "Potent neutralization of Hendra and Nipah viruses by human monoclonal antibodies," *J. Virol.*, 80 (2), 891-899 (2006).

\* cited by examiner

```
SEQUENCE LISTING

<160> NUMBER OF SEQ ID NOS: 94

<210> SEQ ID NO 1
<211> LENGTH: 99
<212> TYPE: PRT
<213> ORGANISM: Artificial Sequence
<220> FEATURE:
<223> OTHER INFORMATION: Synthetic

<400> SEQUENCE: 1

Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80
```

Thr Tyr Ile Cys Glu Val Glu Asp Gln Lys Glu Val Gln Leu Val
                    85                  90                  95

Val Val Gly

<210> SEQ ID NO 2
<211> LENGTH: 99
<212> TYPE: PRT
<213> ORGANISM: Artificial Sequence
<220> FEATURE:
<223> OTHER INFORMATION: Synthetic

<400> SEQUENCE: 2

Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asp Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
        50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Val Gln Leu Val
                    85                  90                  95

Val Val Gly

<210> SEQ ID NO 3
<211> LENGTH: 99
<212> TYPE: PRT
<213> ORGANISM: Artificial Sequence
<220> FEATURE:
<223> OTHER INFORMATION: Synthetic

<400> SEQUENCE: 3

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
        50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Val Gln Leu Leu
                    85                  90                  95

Val Phe Gly

<210> SEQ ID NO 4
<211> LENGTH: 99
<212> TYPE: PRT
<213> ORGANISM: Artificial Sequence
<220> FEATURE:
<223> OTHER INFORMATION: Synthetic

<400> SEQUENCE: 4

Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn

```
                        20                  25                  30
Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
 50                  55                  60

Gly Asn Phe Pro Leu Ile Ile Lys Asn Leu Lys Pro Glu Asp Ser Asp
 65                  70                  75                  80

Thr Tyr Ile Cys Glu Val Glu Asp Gln Lys Glu Glu Val Gln Leu Val
                85                  90                  95

Val Val Gly

<210> SEQ ID NO 5
<211> LENGTH: 227
<212> TYPE: PRT
<213> ORGANISM: Artificial Sequence
<220> FEATURE:
<223> OTHER INFORMATION: Synthetic

<400> SEQUENCE: 5

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 6
<211> LENGTH: 107
<212> TYPE: PRT
<213> ORGANISM: Artificial Sequence
<220> FEATURE:
<223> OTHER INFORMATION: Synthetic
```

<400> SEQUENCE: 6

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Gly Gly Gly Gly Ser Gly Gly Gly Gly Ser Gly Gly Gly Gly Ser
1               5                   10                  15

<210> SEQ ID NO 8
<211> LENGTH: 30
<212> TYPE: PRT
<213> ORGANISM: Artificial Sequence
<220> FEATURE:
<223> OTHER INFORMATION: Synthetic

<400> SEQUENCE: 8

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 9
<211> LENGTH: 45
<212> TYPE: PRT
<213> ORGANISM: Artificial Sequence
<220> FEATURE:
<223> OTHER INFORMATION: Synthetic

<400> SEQUENCE: 9

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Ser
        35                  40                  45

<210> SEQ ID NO 10
<211> LENGTH: 117
<212> TYPE: PRT
<213> ORGANISM: Artificial Sequence
<220> FEATURE:
<223> OTHER INFORMATION: Synthetic
<220> FEATURE:

```
<221> NAME/KEY: CDR1
<222> LOCATION: (26)..(33)
<220> FEATURE:
<221> NAME/KEY: CDR2
<222> LOCATION: (51)..(58)
<220> FEATURE:
<221> NAME/KEY: CDR3
<222> LOCATION: (96)..(106)

<400> SEQUENCE: 10

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Gln Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser
        115

<210> SEQ ID NO 11
<211> LENGTH: 117
<212> TYPE: PRT
<213> ORGANISM: Artificial Sequence
<220> FEATURE:
<223> OTHER INFORMATION: Synthetic
<220> FEATURE:
<221> NAME/KEY: CDR1
<222> LOCATION: (26)..(33)
<220> FEATURE:
<221> NAME/KEY: CDR2
<222> LOCATION: (51)..(58)
<220> FEATURE:
<221> NAME/KEY: CDR3
<222> LOCATION: (96)..(106)

<400> SEQUENCE: 11

Gln Val Gln Leu Val Gln Ser Gly Gly Gly Leu Val Gln Pro Gly Gly
1               5                   10                  15

Ser Leu Arg Leu Ser Cys Ala Ala Ser Thr Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Asn Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser
        115
```

```
<210> SEQ ID NO 12
<211> LENGTH: 117
<212> TYPE: PRT
<213> ORGANISM: Artificial Sequence
<220> FEATURE:
<223> OTHER INFORMATION: Synthetic
<220> FEATURE:
<221> NAME/KEY: CDR1
<222> LOCATION: (26)..(33)
<220> FEATURE:
<221> NAME/KEY: CDR2
<222> LOCATION: (51)..(58)
<220> FEATURE:
<221> NAME/KEY: CDR3
<222> LOCATION: (96)..(106)

<400> SEQUENCE: 12
```

Gln Val Gln Leu Val Gln Ser Gly Gly Gly Leu Ile Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Gln Asp Pro Gly Lys Gly Leu Glu Trp Ile
        35                  40                  45

Gly Glu Ile Asn Asp Arg Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser
        115

```
<210> SEQ ID NO 13
<211> LENGTH: 117
<212> TYPE: PRT
<213> ORGANISM: Artificial Sequence
<220> FEATURE:
<223> OTHER INFORMATION: Synthetic
<220> FEATURE:
<221> NAME/KEY: CDR1
<222> LOCATION: (26)..(33)
<220> FEATURE:
<221> NAME/KEY: CDR2
<222> LOCATION: (51)..(58)
<220> FEATURE:
<221> NAME/KEY: CDR3
<222> LOCATION: (96)..(106)

<400> SEQUENCE: 13
```

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

```
Ile Tyr Gly Gly Asn Ser Gly Gly Glu Tyr Trp Gly Gln Gly Thr Leu
            100                 105                 110

Val Thr Val Ser Ser
        115

<210> SEQ ID NO 14
<211> LENGTH: 117
<212> TYPE: PRT
<213> ORGANISM: Artificial Sequence
<220> FEATURE:
<223> OTHER INFORMATION: Synthetic
<220> FEATURE:
<221> NAME/KEY: CDR1
<222> LOCATION: (26)..(33)
<220> FEATURE:
<221> NAME/KEY: CDR2
<222> LOCATION: (51)..(58)
<220> FEATURE:
<221> NAME/KEY: CDR3
<222> LOCATION: (96)..(106)

<400> SEQUENCE: 14

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Ser Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser
        115

<210> SEQ ID NO 15
<211> LENGTH: 446
<212> TYPE: PRT
<213> ORGANISM: Artificial Sequence
<220> FEATURE:
<223> OTHER INFORMATION: Synthetic

<400> SEQUENCE: 15

Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly Gly Gly Gly Ser Gly Gly Gly Ser Gly Gly Gly
            100                 105                 110
```

```
Gly Ser Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 16
<211> LENGTH: 239
<212> TYPE: PRT
<213> ORGANISM: Artificial Sequence
<220> FEATURE:
<223> OTHER INFORMATION: Synthetic

<400> SEQUENCE: 16

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30
```

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
 50                  55                  60

Ser Arg Val Thr Ile Ser Arg Asp Asn Ser Lys Asn Thr Leu Tyr Leu
 65                  70                  75                  80

Gln Met Asn Thr Leu Arg Ala Glu Asp Thr Ala Ile Tyr Tyr Cys Ala
                 85                  90                  95

Ile Tyr Gly Gly Asn Ser Gly Gly Glu Tyr Trp Gly Gln Gly Thr Leu
             100                 105                 110

Val Thr Val Ser Ser Gly Gly Gly Gly Ser Gly Gly Gly Gly Ser Gly
         115                 120                 125

Gly Gly Gly Ser Arg Thr Val Ala Ala Pro Ser Val Phe Ile Phe Pro
     130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 17
<211> LENGTH: 560
<212> TYPE: PRT
<213> ORGANISM: Artificial Sequence
<220> FEATURE:
<223> OTHER INFORMATION: Synthetic

<400> SEQUENCE: 17

Lys Lys Val Val Tyr Gly Lys Gly Asp Thr Val Glu Leu Thr Cys
1               5                   10                  15

Thr Ala Ser Gln Lys Lys Asn Ile Gln Phe His Trp Lys Asn Ser Asn
             20                  25                  30

Gln Ile Lys Ile Leu Gly Asn Gln Gly Ser Phe Leu Thr Lys Gly Pro
         35                  40                  45

Ser Lys Leu Asn Asp Arg Val Asp Ser Arg Arg Ser Leu Trp Asp Gln
 50                  55                  60

Gly Asn Phe Pro Leu Ile Ile Lys Asn Leu Lys Pro Glu Asp Ser Asp
 65                  70                  75                  80

Thr Tyr Ile Cys Glu Val Glu Asp Gln Lys Glu Glu Val Gln Leu Val
                 85                  90                  95

Val Val Gly Gly Gly Gly Ser Gly Gly Gly Ser Gly Gly Gly
            100                 105                 110

Gly Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

```
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys Gly Gly
        435                 440                 445

Gly Gly Ser Gly Gly Gly Ser Gly Gly Gly Ser Lys Lys Val
    450                 455                 460

Val Tyr Gly Lys Lys Gly Asp Thr Val Glu Leu Thr Cys Thr Ala Ser
465                 470                 475                 480

Gln Lys Lys Asn Ile Gln Phe His Trp Lys Asn Ser Asn Gln Ile Lys
                485                 490                 495

Ile Leu Gly Asn Gln Gly Ser Phe Leu Thr Lys Gly Pro Ser Lys Leu
            500                 505                 510

Asn Asp Arg Val Asp Ser Arg Arg Ser Leu Trp Asp Gln Gly Asn Phe
        515                 520                 525

Pro Leu Ile Ile Lys Asn Leu Lys Pro Glu Asp Ser Asp Thr Tyr Ile
    530                 535                 540

Cys Glu Val Glu Asp Gln Lys Glu Glu Val Gln Leu Val Val Val Gly
545                 550                 555                 560

<210> SEQ ID NO 18
<211> LENGTH: 239
```

<212> TYPE: PRT
<213> ORGANISM: Artificial Sequence
<220> FEATURE:
<223> OTHER INFORMATION: Synthetic

<400> SEQUENCE: 18

```
Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser Gly Gly Gly Ser Gly Gly Gly Gly Ser Gly
        115                 120                 125

Gly Gly Gly Ser Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235
```

<210> SEQ ID NO 19
<211> LENGTH: 560
<212> TYPE: PRT
<213> ORGANISM: Artificial Sequence
<220> FEATURE:
<223> OTHER INFORMATION: Synthetic

<400> SEQUENCE: 19

```
Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95
```

```
Val Val Gly Gly Gly Gly Ser Gly Gly Gly Ser Gly Gly Gly
        100             105             110

Gly Ser Ser Ser Ala Ser Thr Lys Gly Pro Ser Val Phe Pro Leu Ala
            115             120             125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys Gly Gly
            435                 440                 445

Gly Gly Ser Gly Gly Gly Gly Ser Gly Gly Gly Gly Ser Lys Lys Val
        450                 455                 460

Val Tyr Gly Lys Lys Gly Asp Thr Val Glu Leu Thr Cys Thr Ala Ser
465                 470                 475                 480

Gln Lys Lys Asn Ile Gln Phe His Trp Lys Asn Ser Asn Gln Ile Lys
                485                 490                 495

Ile Leu Gly Asn Gln Gly Ser Phe Leu Thr Lys Gly Pro Ser Lys Leu
                500                 505                 510
```

```
Asn Asp Arg Val Asp Ser Arg Ser Leu Trp Asp Gln Gly Asn Phe
            515                 520                 525

Pro Leu Ile Ile Lys Asn Leu Lys Pro Glu Asp Ser Asp Thr Tyr Ile
    530                 535                 540

Cys Glu Val Glu Asp Gln Lys Glu Val Gln Leu Val Val Gly
545                 550                 555                 560

<210> SEQ ID NO 20
<211> LENGTH: 353
<212> TYPE: PRT
<213> ORGANISM: Artificial Sequence
<220> FEATURE:
<223> OTHER INFORMATION: Synthetic

<400> SEQUENCE: 20

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys Gly
225                 230                 235                 240

Gly Gly Gly Ser Gly Gly Gly Gly Ser Gly Gly Gly Gly Ser Lys Lys
                245                 250                 255

Val Val Tyr Gly Lys Lys Gly Asp Thr Val Glu Leu Thr Cys Thr Ala
            260                 265                 270

Ser Gln Lys Lys Asn Ile Gln Phe His Trp Lys Asn Ser Asn Gln Ile
        275                 280                 285

Lys Ile Leu Gly Asn Gln Gly Ser Phe Leu Thr Lys Gly Pro Ser Lys
    290                 295                 300

Leu Asn Asp Arg Val Asp Ser Arg Arg Ser Leu Trp Asp Gln Gly Asn
305                 310                 315                 320
```

```
Phe Pro Leu Ile Ile Lys Asn Leu Lys Pro Glu Asp Ser Asp Thr Tyr
                325                 330                 335

Ile Cys Glu Val Glu Asp Gln Lys Glu Val Gln Leu Val Val Val
            340                 345                 350

Gly

<210> SEQ ID NO 21
<211> LENGTH: 103
<212> TYPE: PRT
<213> ORGANISM: Artificial Sequence
<220> FEATURE:
<223> OTHER INFORMATION: Synthetic

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 22
<211> LENGTH: 103
<212> TYPE: PRT
<213> ORGANISM: Artificial Sequence
<220> FEATURE:
<223> OTHER INFORMATION: Synthetic

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Tyr
    50                  55                  60

Leu Leu Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 23
<211> LENGTH: 103
<212> TYPE: PRT
<213> ORGANISM: Artificial Sequence
<220> FEATURE:
<223> OTHER INFORMATION: Synthetic

<400> SEQUENCE: 23
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Asn
    50                  55                  60

Leu Tyr Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100
```

<210> SEQ ID NO 24
<211> LENGTH: 103
<212> TYPE: PRT
<213> ORGANISM: Artificial Sequence
<220> FEATURE:
<223> OTHER INFORMATION: Synthetic

<400> SEQUENCE: 24

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Glu
    50                  55                  60

Leu Val Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100
```

<210> SEQ ID NO 25
<211> LENGTH: 103
<212> TYPE: PRT
<213> ORGANISM: Artificial Sequence
<220> FEATURE:
<223> OTHER INFORMATION: Synthetic

<400> SEQUENCE: 25

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Thr
    50                  55                  60

Leu Phe Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

Lys Val Glu Pro Lys Ser Cys
            100

<210> SEQ ID NO 26
<211> LENGTH: 103
<212> TYPE: PRT
<213> ORGANISM: Artificial Sequence
<220> FEATURE:
<223> OTHER INFORMATION: Synthetic

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Lys
    50                  55                  60

Leu Val Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 27
<211> LENGTH: 103
<212> TYPE: PRT
<213> ORGANISM: Artificial Sequence
<220> FEATURE:
<223> OTHER INFORMATION: Synthetic

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Met
    50                  55                  60

Leu Phe Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 28
<211> LENGTH: 107
<212> TYPE: PRT
<213> ORGANISM: Artificial Sequence
<220> FEATURE:
<223> OTHER INFORMATION: Synthetic

<400> SEQUENCE: 28

Arg Thr Val Ala Ala Pro Ser Val Phe Ile Phe Pro Pro Ser Asp Glu
1               5                   10                  15

```
Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 29
<211> LENGTH: 107
<212> TYPE: PRT
<213> ORGANISM: Artificial Sequence
<220> FEATURE:
<223> OTHER INFORMATION: Synthetic

<400> SEQUENCE: 29

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Phe Ser Trp Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 30
<211> LENGTH: 107
<212> TYPE: PRT
<213> ORGANISM: Artificial Sequence
<220> FEATURE:
<223> OTHER INFORMATION: Synthetic

<400> SEQUENCE: 30

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ala Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
```

<210> SEQ ID NO 31
<211> LENGTH: 107
<212> TYPE: PRT
<213> ORGANISM: Artificial Sequence
<220> FEATURE:
<223> OTHER INFORMATION: Synthetic

<400> SEQUENCE: 31

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Leu Ser Ser Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 32
<211> LENGTH: 107
<212> TYPE: PRT
<213> ORGANISM: Artificial Sequence
<220> FEATURE:
<223> OTHER INFORMATION: Synthetic

<400> SEQUENCE: 32

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Val Ser Arg Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 33
<211> LENGTH: 107
<212> TYPE: PRT
<213> ORGANISM: Artificial Sequence
<220> FEATURE:
<223> OTHER INFORMATION: Synthetic

<400> SEQUENCE: 33

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Val Ser Ala Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 34
<211> LENGTH: 107
<212> TYPE: PRT
<213> ORGANISM: Artificial Sequence
<220> FEATURE:
<223> OTHER INFORMATION: Synthetic

<400> SEQUENCE: 34

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Glu Ser Val Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 35
<211> LENGTH: 5
<212> TYPE: PRT
<213> ORGANISM: Artificial Sequence
<220> FEATURE:
<223> OTHER INFORMATION: Synthetic

<400> SEQUENCE: 35

Asp Lys Thr His Thr
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic

<400> SEQUENCE: 36

Gly Gly Gly Gly Ser
1               5

<210> SEQ ID NO 37
<211> LENGTH: 107
<212> TYPE: PRT
<213> ORGANISM: Artificial Sequence
<220> FEATURE:

<223> OTHER INFORMATION: Synthetic

<400> SEQUENCE: 37

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Leu Ser Ser Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 38
<211> LENGTH: 103
<212> TYPE: PRT
<213> ORGANISM: Artificial Sequence
<220> FEATURE:
<223> OTHER INFORMATION: Synthetic

<400> SEQUENCE: 38

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Glu
    50                  55                  60

Leu Val Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100
```

<210> SEQ ID NO 39
<211> LENGTH: 560
<212> TYPE: PRT
<213> ORGANISM: Artificial Sequence
<220> FEATURE:
<223> OTHER INFORMATION: Synthetic

<400> SEQUENCE: 39

```
Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
```

-continued

```
              65                  70                  75                  80
Thr Tyr Ile Cys Glu Val Glu Asp Gln Lys Glu Val Gln Leu Val
                     85                  90                  95

Val Val Gly Gly Gly Gly Ser Gly Gly Gly Ser Gly Gly Gly
                    100                 105                 110

Gly Ser Ser Ser Ala Ser Thr Lys Gly Pro Ser Val Phe Pro Leu Ala
                    115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                    165                 170                 175

Gly Leu Tyr Glu Leu Val Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                    245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                    325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                    405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys Gly Gly
            435                 440                 445

Gly Gly Ser Gly Gly Gly Ser Gly Gly Gly Ser Lys Lys Val
            450                 455                 460

Val Tyr Gly Lys Lys Gly Asp Thr Val Glu Leu Thr Cys Thr Ala Ser
465                 470                 475                 480

Gln Lys Lys Asn Ile Gln Phe His Trp Lys Asn Ser Asn Gln Ile Lys
                    485                 490                 495
```

Ile Leu Gly Asn Gln Gly Ser Phe Leu Thr Lys Gly Pro Ser Lys Leu
                500                 505                 510

Asn Asp Arg Val Asp Ser Arg Ser Leu Trp Asp Gln Gly Asn Phe
                515                 520                 525

Pro Leu Ile Ile Lys Asn Leu Lys Pro Glu Asp Ser Asp Thr Tyr Ile
530                 535                 540

Cys Glu Val Glu Asp Gln Lys Glu Val Gln Leu Val Val Gly
545                 550                 555                 560

<210> SEQ ID NO 40
<211> LENGTH: 239
<212> TYPE: PRT
<213> ORGANISM: Artificial Sequence
<220> FEATURE:
<223> OTHER INFORMATION: Synthetic

<400> SEQUENCE: 40

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
                20                  25                  30

Glu Met Ser Trp Val Arg Glu Ala Pro Gly Lys Gly Leu Glu Trp Ile
            35                  40                  45

Gly Glu Ile Asn Asp Ser Gly Asn Thr Ile Tyr Asn Pro Ser Leu Lys
50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Leu Ser Ser Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 41
<211> LENGTH: 539
<212> TYPE: PRT
<213> ORGANISM: Artificial Sequence
<220> FEATURE:
<223> OTHER INFORMATION: Synthetic

<400> SEQUENCE: 41

Lys Lys Val Val Tyr Gly Lys Lys Gly Asp Thr Val Glu Leu Thr Cys

-continued

```
1               5                   10                  15
Thr Ala Ser Gln Lys Lys Asn Ile Gln Phe His Trp Lys Asn Ser Asn
                20                  25                  30
Gln Ile Lys Ile Leu Gly Asn Gln Gly Ser Phe Leu Thr Lys Gly Pro
                35                  40                  45
Ser Lys Leu Asn Asp Arg Val Asp Ser Arg Arg Ser Leu Trp Asp Gln
                50                  55                  60
Gly Asn Phe Pro Leu Ile Ile Lys Asn Leu Lys Pro Glu Asp Ser Asp
65                              70                  75                  80
Thr Tyr Ile Cys Glu Val Glu Asp Gln Lys Glu Glu Val Gln Leu Val
                        85                  90                  95
Val Val Gly Gly Gly Gly Ser Ser Ala Ser Thr Lys Gly Pro Ser
                    100                 105                 110
Val Phe Pro Leu Ala Pro Ser Ser Lys Ser Thr Ser Gly Gly Thr Ala
                    115                 120                 125
Ala Leu Gly Cys Leu Val Lys Asp Tyr Phe Pro Glu Pro Val Thr Val
                    130                 135                 140
Ser Trp Asn Ser Gly Ala Leu Thr Ser Gly Val His Thr Phe Pro Ala
145                             150                 155                 160
Val Leu Gln Ser Ser Gly Leu Tyr Glu Leu Val Ser Val Val Thr Val
                    165                 170                 175
Pro Ser Ser Ser Leu Gly Thr Gln Thr Tyr Ile Cys Asn Val Asn His
                180                 185                 190
Lys Pro Ser Asn Thr Lys Val Asp Lys Lys Val Glu Pro Lys Ser Cys
                195                 200                 205
Asp Lys Thr His Thr Cys Pro Pro Cys Pro Ala Pro Glu Leu Leu Gly
                210                 215                 220
Gly Pro Ser Val Phe Leu Phe Pro Pro Lys Pro Lys Asp Thr Leu Met
225                             230                 235                 240
Ile Ser Arg Thr Pro Glu Val Thr Cys Val Val Val Asp Val Ser His
                    245                 250                 255
Glu Asp Pro Glu Val Lys Phe Asn Trp Tyr Val Asp Gly Val Glu Val
                260                 265                 270
His Asn Ala Lys Thr Lys Pro Arg Glu Glu Gln Tyr Asn Ser Thr Tyr
                275                 280                 285
Arg Val Val Ser Val Leu Thr Val Leu His Gln Asp Trp Leu Asn Gly
                290                 295                 300
Lys Glu Tyr Lys Cys Lys Val Ser Asn Lys Ala Leu Pro Ala Pro Ile
305                             310                 315                 320
Glu Lys Thr Ile Ser Lys Ala Lys Gly Gln Pro Arg Glu Pro Gln Val
                        325                 330                 335
Tyr Thr Leu Pro Pro Ser Arg Asp Glu Leu Thr Lys Asn Gln Val Ser
                340                 345                 350
Leu Thr Cys Leu Val Lys Gly Phe Tyr Pro Ser Asp Ile Ala Val Glu
                    355                 360                 365
Trp Glu Ser Asn Gly Gln Pro Glu Asn Asn Tyr Lys Thr Thr Pro Pro
                    370                 375                 380
Val Leu Asp Ser Asp Gly Ser Phe Phe Leu Tyr Ser Lys Leu Thr Val
385                             390                 395                 400
Asp Lys Ser Arg Trp Gln Gln Gly Asn Val Phe Ser Cys Ser Val Met
                        405                 410                 415
His Glu Ala Leu His Asn His Tyr Thr Gln Lys Ser Leu Ser Leu Ser
                420                 425                 430
```

```
Pro Gly Lys Gly Gly Gly Ser Lys Val Val Tyr Gly Lys Lys
    435                 440                 445

Gly Asp Thr Val Glu Leu Thr Cys Thr Ala Ser Gln Lys Lys Asn Ile
450                 455                 460

Gln Phe His Trp Lys Asn Ser Asn Gln Ile Lys Ile Leu Gly Asn Gln
465                 470                 475                 480

Gly Ser Phe Leu Thr Lys Gly Pro Ser Lys Leu Asn Asp Arg Val Asp
                485                 490                 495

Ser Arg Arg Ser Leu Trp Asp Gln Gly Asn Phe Pro Leu Ile Ile Lys
            500                 505                 510

Asn Leu Lys Pro Glu Asp Ser Asp Thr Tyr Ile Cys Glu Val Glu Asp
        515                 520                 525

Gln Lys Glu Glu Val Gln Leu Val Val Val Gly
    530                 535

<210> SEQ ID NO 42
<211> LENGTH: 229
<212> TYPE: PRT
<213> ORGANISM: Artificial Sequence
<220> FEATURE:
<223> OTHER INFORMATION: Synthetic

<400> SEQUENCE: 42

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser Gly Gly Gly Gly Ser Arg Thr Val Ala Ala Pro
        115                 120                 125

Ser Val Phe Ile Phe Pro Pro Ser Asp Glu Gln Leu Lys Ser Gly Thr
    130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Leu Ser
            180                 185                 190

Ser Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220

Asn Arg Gly Glu Cys
225

<210> SEQ ID NO 43
```

<211> LENGTH: 540
<212> TYPE: PRT
<213> ORGANISM: Artificial Sequence
<220> FEATURE:
<223> OTHER INFORMATION: Synthetic

<400> SEQUENCE: 43

```
Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly Asp Lys Thr His Thr Ser Ser Ala Ser Thr Lys Gly Pro
            100                 105                 110

Ser Val Phe Pro Leu Ala Pro Ser Ser Lys Ser Thr Ser Gly Gly Thr
        115                 120                 125

Ala Ala Leu Gly Cys Leu Val Lys Asp Tyr Phe Pro Glu Pro Val Thr
    130                 135                 140

Val Ser Trp Asn Ser Gly Ala Leu Thr Ser Gly Val His Thr Phe Pro
145                 150                 155                 160

Ala Val Leu Gln Ser Ser Gly Leu Tyr Glu Leu Val Ser Val Val Thr
                165                 170                 175

Val Pro Ser Ser Ser Leu Gly Thr Gln Thr Tyr Ile Cys Asn Val Asn
            180                 185                 190

His Lys Pro Ser Asn Thr Lys Val Asp Lys Lys Val Glu Pro Lys Ser
        195                 200                 205

Cys Asp Lys Thr His Thr Cys Pro Pro Cys Pro Ala Pro Glu Leu Leu
    210                 215                 220

Gly Gly Pro Ser Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

His Glu Asp Pro Glu Val Lys Phe Asn Trp Tyr Val Asp Gly Val Glu
            260                 265                 270

Val His Asn Ala Lys Thr Lys Pro Arg Glu Glu Gln Tyr Asn Ser Thr
        275                 280                 285

Tyr Arg Val Val Ser Val Leu Thr Val Leu His Gln Asp Trp Leu Asn
    290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Arg Asp Glu Leu Thr Lys Asn Gln Val
            340                 345                 350

Ser Leu Thr Cys Leu Val Lys Gly Phe Tyr Pro Ser Asp Ile Ala Val
        355                 360                 365

Glu Trp Glu Ser Asn Gly Gln Pro Glu Asn Asn Tyr Lys Thr Thr Pro
    370                 375                 380
```

Pro Val Leu Asp Ser Asp Gly Ser Phe Phe Leu Tyr Ser Lys Leu Thr
385                 390                 395                 400

Val Asp Lys Ser Arg Trp Gln Gln Gly Asn Val Phe Ser Cys Ser Val
            405                 410                 415

Met His Glu Ala Leu His Asn His Tyr Thr Gln Lys Ser Leu Ser Leu
        420                 425                 430

Ser Pro Gly Lys Asp Lys Thr His Thr Lys Lys Val Val Tyr Gly Lys
    435                 440                 445

Lys Gly Asp Thr Val Glu Leu Thr Cys Thr Ala Ser Gln Lys Lys Asn
    450                 455                 460

Ile Gln Phe His Trp Lys Asn Ser Asn Gln Ile Lys Ile Leu Gly Asn
465                 470                 475                 480

Gln Gly Ser Phe Leu Thr Lys Gly Pro Ser Lys Leu Asn Asp Arg Val
            485                 490                 495

Asp Ser Arg Arg Ser Leu Trp Asp Gln Gly Asn Phe Pro Leu Ile Ile
            500                 505                 510

Lys Asn Leu Lys Pro Glu Asp Ser Asp Thr Tyr Ile Cys Glu Val Glu
            515                 520                 525

Asp Gln Lys Glu Glu Val Gln Leu Val Val Val Gly
            530                 535                 540

<210> SEQ ID NO 44
<211> LENGTH: 229
<212> TYPE: PRT
<213> ORGANISM: Artificial Sequence
<220> FEATURE:
<223> OTHER INFORMATION: Synthetic

<400> SEQUENCE: 44

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
            85                  90                  95

Ile Tyr Gly Gly Asn Ser Gly Gly Glu Tyr Trp Gly Gln Gly Thr Leu
            100                 105                 110

Val Thr Val Ser Ser Asp Lys Thr His Thr Arg Thr Val Ala Ala Pro
        115                 120                 125

Ser Val Phe Ile Phe Pro Pro Ser Asp Glu Gln Leu Lys Ser Gly Thr
    130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
            165                 170                 175

Ser Val Thr Glu Gln Asp Ser Lys Asp Ser Thr Tyr Ser Leu Leu Ser
            180                 185                 190

Ser Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
210                 215                 220

Asn Arg Gly Glu Cys
225

<210> SEQ ID NO 45
<211> LENGTH: 560
<212> TYPE: PRT
<213> ORGANISM: Artificial Sequence
<220> FEATURE:
<223> OTHER INFORMATION: Synthetic

<400> SEQUENCE: 45

Lys Lys Val Val Tyr Gly Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly Gly Gly Gly Ser Gly Gly Gly Ser Gly Gly Gly
            100                 105                 110

Gly Ser Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Glu Leu Val Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Leu His Glu Ala Leu His
            420                 425                 430

Ser His Tyr Thr Gln Lys Ser Leu Ser Leu Ser Pro Gly Lys Gly Gly
            435                 440                 445

Gly Gly Ser Gly Gly Gly Ser Gly Gly Gly Ser Lys Lys Val
            450                 455                 460

Val Tyr Gly Lys Lys Gly Asp Thr Val Glu Leu Thr Cys Thr Ala Ser
465                 470                 475                 480

Gln Lys Lys Asn Ile Gln Phe His Trp Lys Asn Ser Asn Gln Ile Lys
                485                 490                 495

Ile Leu Gly Asn Gln Gly Ser Phe Leu Thr Lys Gly Pro Ser Lys Leu
            500                 505                 510

Asn Asp Arg Val Asp Ser Arg Arg Ser Leu Trp Asp Gln Gly Asn Phe
            515                 520                 525

Pro Leu Ile Ile Lys Asn Leu Lys Pro Glu Asp Ser Asp Thr Tyr Ile
            530                 535                 540

Cys Glu Val Glu Asp Gln Lys Glu Glu Val Gln Leu Val Val Val Gly
545                 550                 555                 560

<210> SEQ ID NO 46
<211> LENGTH: 239
<212> TYPE: PRT
<213> ORGANISM: Artificial Sequence
<220> FEATURE:
<223> OTHER INFORMATION: Synthetic

<400> SEQUENCE: 46

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
            35                  40                  45

Gly Glu Ile Asn Asp Ser Gly Asn Thr Ile Tyr Asn Pro Ser Leu Lys
        50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser Gly Gly Gly Ser Gly Gly Gly Gly Ser Gly
            115                 120                 125

Gly Gly Gly Ser Arg Thr Val Ala Ala Pro Ser Val Phe Ile Phe Pro
            130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Leu Ser Ser Leu Thr Leu Ser Lys
            195                 200                 205

Ala Asp Tyr Glu Lys His Lys Val Tyr Ala Cys Glu Val Thr His Gln
        210                 215                 220

Gly Leu Ser Ser Pro Val Thr Lys Ser Phe Asn Arg Gly Glu Cys
225                 230                 235

<210> SEQ ID NO 47
<211> LENGTH: 539
<212> TYPE: PRT
<213> ORGANISM: Artificial Sequence
<220> FEATURE:
<223> OTHER INFORMATION: Synthetic

<400> SEQUENCE: 47

Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Val Asp Ser Arg Arg Ser Leu Trp Asp Gln
50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly Gly Gly Gly Ser Ser Ala Ser Thr Lys Gly Pro Ser
            100                 105                 110

Val Phe Pro Leu Ala Pro Ser Ser Lys Ser Thr Ser Gly Gly Thr Ala
        115                 120                 125

Ala Leu Gly Cys Leu Val Lys Asp Tyr Phe Pro Glu Pro Val Thr Val
    130                 135                 140

Ser Trp Asn Ser Gly Ala Leu Thr Ser Gly Val His Thr Phe Pro Ala
145                 150                 155                 160

Val Leu Gln Ser Ser Gly Leu Tyr Glu Leu Val Ser Val Val Thr Val
                165                 170                 175

Pro Ser Ser Ser Leu Gly Thr Gln Thr Tyr Ile Cys Asn Val Asn His
            180                 185                 190

Lys Pro Ser Asn Thr Lys Val Asp Lys Lys Val Glu Pro Lys Ser Cys
        195                 200                 205

Asp Lys Thr His Thr Cys Pro Pro Cys Pro Ala Pro Glu Leu Leu Gly
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Ser His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Gln Tyr Asn Ser Thr Tyr
            275                 280                 285

Arg Val Val Ser Val Leu Thr Val Leu His Gln Asp Trp Leu Asn Gly
        290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Asp Glu Leu Thr Lys Asn Gln Val Ser
            340                 345                 350

Leu Thr Cys Leu Val Lys Gly Phe Tyr Pro Ser Asp Ile Ala Val Glu
        355                 360                 365

Trp Glu Ser Asn Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
385                 390                 395                 400

Asp Lys Ser Arg Trp Gln Gln Gly Asn Val Phe Ser Cys Ser Val Leu
                405                 410                 415

His Glu Ala Leu His Ser His Tyr Thr Gln Lys Ser Leu Ser Leu Ser
            420                 425                 430

Pro Gly Lys Gly Gly Gly Gly Ser Lys Lys Val Val Tyr Gly Lys Lys
        435                 440                 445

Gly Asp Thr Val Glu Leu Thr Cys Thr Ala Ser Gln Lys Lys Asn Ile
    450                 455                 460

Gln Phe His Trp Lys Asn Ser Asn Gln Ile Lys Ile Leu Gly Asn Gln
465                 470                 475                 480

Gly Ser Phe Leu Thr Lys Gly Pro Ser Lys Leu Asn Asp Arg Val Asp
                485                 490                 495

Ser Arg Arg Ser Leu Trp Asp Gln Gly Asn Phe Pro Leu Ile Ile Lys
            500                 505                 510

Asn Leu Lys Pro Glu Asp Ser Asp Thr Tyr Ile Cys Glu Val Glu Asp
        515                 520                 525

Gln Lys Glu Glu Val Gln Leu Val Val Val Gly
    530                 535

<210> SEQ ID NO 48
<211> LENGTH: 229
<212> TYPE: PRT
<213> ORGANISM: Artificial Sequence
<220> FEATURE:
<223> OTHER INFORMATION: Synthetic

<400> SEQUENCE: 48

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

```
Ile Tyr Gly Gly Asn Ser Gly Glu Tyr Trp Gln Gly Thr Leu
            100                 105                 110
Val Thr Val Ser Ser Gly Gly Gly Ser Arg Thr Val Ala Ala Pro
        115                 120                 125
Ser Val Phe Ile Phe Pro Pro Ser Asp Glu Gln Leu Lys Ser Gly Thr
    130                 135                 140
Ala Ser Val Val Cys Leu Leu Asn Asn Phe Tyr Pro Arg Glu Ala Lys
145                 150                 155                 160
Val Gln Trp Lys Val Asp Asn Ala Leu Gln Ser Gly Asn Ser Gln Glu
                165                 170                 175
Ser Val Thr Glu Gln Asp Ser Lys Asp Ser Thr Tyr Ser Leu Leu Ser
            180                 185                 190
Ser Leu Thr Leu Ser Lys Ala Asp Tyr Glu Lys His Lys Val Tyr Ala
        195                 200                 205
Cys Glu Val Thr His Gln Gly Leu Ser Ser Pro Val Thr Lys Ser Phe
    210                 215                 220
Asn Arg Gly Glu Cys
225

<210> SEQ ID NO 49
<211> LENGTH: 540
<212> TYPE: PRT
<213> ORGANISM: Artificial Sequence
<220> FEATURE:
<223> OTHER INFORMATION: Synthetic

<400> SEQUENCE: 49

Lys Lys Val Val Tyr Gly Lys Lys Gly Asp Thr Val Glu Leu Thr Cys
1               5                   10                  15
Thr Ala Ser Gln Lys Lys Asn Ile Gln Phe His Trp Lys Asn Ser Asn
            20                  25                  30
Gln Ile Lys Ile Leu Gly Asn Gln Gly Ser Phe Leu Thr Lys Gly Pro
        35                  40                  45
Ser Lys Leu Asn Asp Arg Val Asp Ser Arg Arg Ser Leu Trp Asp Gln
    50                  55                  60
Gly Asn Phe Pro Leu Ile Ile Lys Asn Leu Lys Pro Glu Asp Ser Asp
65                  70                  75                  80
Thr Tyr Ile Cys Glu Val Glu Asp Gln Lys Glu Glu Val Gln Leu Val
                85                  90                  95
Val Val Gly Asp Lys Thr His Thr Ser Ser Ala Ser Thr Lys Gly Pro
            100                 105                 110
Ser Val Phe Pro Leu Ala Pro Ser Ser Lys Ser Thr Ser Gly Gly Thr
        115                 120                 125
Ala Ala Leu Gly Cys Leu Val Lys Asp Tyr Phe Pro Glu Pro Val Thr
    130                 135                 140
Val Ser Trp Asn Ser Gly Ala Leu Thr Ser Gly Val His Thr Phe Pro
145                 150                 155                 160
Ala Val Leu Gln Ser Ser Gly Leu Tyr Glu Leu Val Ser Val Val Thr
                165                 170                 175
Val Pro Ser Ser Ser Leu Gly Thr Gln Thr Tyr Ile Cys Asn Val Asn
            180                 185                 190
His Lys Pro Ser Asn Thr Lys Val Asp Lys Lys Val Glu Pro Lys Ser
        195                 200                 205
Cys Asp Lys Thr His Thr Cys Pro Pro Cys Pro Ala Pro Glu Leu Leu
    210                 215                 220
```

Gly Gly Pro Ser Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
            245                 250                 255

His Glu Asp Pro Glu Val Lys Phe Asn Trp Tyr Val Asp Gly Val Glu
        260                 265                 270

Val His Asn Ala Lys Thr Lys Pro Arg Glu Glu Gln Tyr Asn Ser Thr
    275                 280                 285

Tyr Arg Val Val Ser Val Leu Thr Val Leu His Gln Asp Trp Leu Asn
290                 295                 300

Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
            325                 330                 335

Val Tyr Thr Leu Pro Pro Ser Arg Asp Glu Leu Thr Lys Asn Gln Val
        340                 345                 350

Ser Leu Thr Cys Leu Val Lys Gly Phe Tyr Pro Ser Asp Ile Ala Val
    355                 360                 365

Glu Trp Glu Ser Asn Gly Gln Pro Glu Asn Asn Tyr Lys Thr Thr Pro
370                 375                 380

Pro Val Leu Asp Ser Asp Gly Ser Phe Phe Leu Tyr Ser Lys Leu Thr
385                 390                 395                 400

Val Asp Lys Ser Arg Trp Gln Gln Gly Asn Val Phe Ser Cys Ser Val
            405                 410                 415

Leu His Glu Ala Leu His Ser His Tyr Thr Gln Lys Ser Leu Ser Leu
        420                 425                 430

Ser Pro Gly Lys Asp Lys Thr His Thr Lys Val Val Tyr Gly Lys
    435                 440                 445

Lys Gly Asp Thr Val Glu Leu Thr Cys Thr Ala Ser Gln Lys Lys Asn
450                 455                 460

Ile Gln Phe His Trp Lys Asn Ser Asn Gln Ile Lys Ile Leu Gly Asn
465                 470                 475                 480

Gln Gly Ser Phe Leu Thr Lys Gly Pro Ser Lys Leu Asn Asp Arg Val
            485                 490                 495

Asp Ser Arg Arg Ser Leu Trp Asp Gln Gly Asn Phe Pro Leu Ile Ile
        500                 505                 510

Lys Asn Leu Lys Pro Glu Asp Ser Asp Thr Tyr Ile Cys Glu Val Glu
    515                 520                 525

Asp Gln Lys Glu Glu Val Gln Leu Val Val Val Gly
530                 535                 540

<210> SEQ ID NO 50
<211> LENGTH: 229
<212> TYPE: PRT
<213> ORGANISM: Artificial Sequence
<220> FEATURE:
<223> OTHER INFORMATION: Synthetic

<400> SEQUENCE: 50

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

```
Gly Glu Ile Asn Asp Ser Gly Asn Thr Ile Tyr Asn Pro Ser Leu Lys
 50                  55                  60

Ser Arg Val Thr Ile Ser Arg Asp Asn Ser Lys Asn Thr Leu Tyr Leu
 65                  70                  75                  80

Gln Met Asn Thr Leu Arg Ala Glu Asp Thr Ala Ile Tyr Tyr Cys Ala
                 85                  90                  95

Ile Tyr Gly Gly Asn Ser Gly Gly Glu Tyr Trp Gly Gln Gly Thr Leu
                100                 105                 110

Val Thr Val Ser Ser Asp Lys Thr His Thr Arg Thr Val Ala Ala Pro
            115                 120                 125

Ser Val Phe Ile Phe Pro Pro Ser Asp Glu Gln Leu Lys Ser Gly Thr
130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Leu Ser
            180                 185                 190

Ser Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
210                 215                 220

Asn Arg Gly Glu Cys
225

<210> SEQ ID NO 51
<211> LENGTH: 227
<212> TYPE: PRT
<213> ORGANISM: Artificial Sequence
<220> FEATURE:
<223> OTHER INFORMATION: Synthetic

<400> SEQUENCE: 51

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
             35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

Val Leu Asp Ser Asp Gly Ser Phe Phe Leu Tyr Ser Lys Leu Thr Val
        180                 185                 190

Asp Lys Ser Arg Trp Gln Gln Gly Asn Val Phe Ser Cys Ser Val Leu
        195                 200                 205

His Glu Ala Leu His Ser His Tyr Thr Gln Lys Ser Leu Ser Leu Ser
        210                 215                 220

Pro Gly Lys
225

<210> SEQ ID NO 52
<211> LENGTH: 36
<212> TYPE: DNA
<213> ORGANISM: Artificial Sequence
<220> FEATURE:
<223> OTHER INFORMATION: Synthetic

<400> SEQUENCE: 52
accgtggccc aggcggccca ggtgcagctg gtgcag                                36

<210> SEQ ID NO 53
<211> LENGTH: 75
<212> TYPE: DNA
<213> ORGANISM: Artificial Sequence
<220> FEATURE:
<223> OTHER INFORMATION: Synthetic

<400> SEQUENCE: 53
ctaattaatt atctagaatt actcgagttt agctgccggt gcgggtgtag ctgcaggaca    60
ctctcccctg ttgaa                                                     75

<210> SEQ ID NO 54
<211> LENGTH: 33
<212> TYPE: DNA
<213> ORGANISM: Artificial Sequence
<220> FEATURE:
<223> OTHER INFORMATION: Synthetic

<400> SEQUENCE: 54
caaccagcca tggccaagaa ggtggtgtac ggc                                  33

<210> SEQ ID NO 55
<211> LENGTH: 89
<212> TYPE: DNA
<213> ORGANISM: Artificial Sequence
<220> FEATURE:
<223> OTHER INFORMATION: Synthetic

<400> SEQUENCE: 55
tggaggccgg cctggcctta ctcgagttta gctgccggtg cgggtgtagc tgcaggacaa    60
gatttgggct caactttctt gtccacctt                                      89

<210> SEQ ID NO 56
<211> LENGTH: 51
<212> TYPE: DNA
<213> ORGANISM: Artificial Sequence
<220> FEATURE:
<223> OTHER INFORMATION: Synthetic

<400> SEQUENCE: 56
gcctacggca gccgctggat tgttattact tgctgcccaa ccagccatgg c              51

<210> SEQ ID NO 57

```
<211> LENGTH: 60
<212> TYPE: DNA
<213> ORGANISM: Artificial Sequence
<220> FEATURE:
<223> OTHER INFORMATION: Synthetic

<400> SEQUENCE: 57
ccagcggctg ccgtaggcaa taggtatttc attttaaatt cctcctaatt aattatctag    60

<210> SEQ ID NO 58
<211> LENGTH: 18
<212> TYPE: DNA
<213> ORGANISM: Artificial Sequence
<220> FEATURE:
<223> OTHER INFORMATION: Synthetic

<400> SEQUENCE: 58
gtgtggaatt gtgagcgg                                                  18

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
gaggctgtag gtgctgtc                                                  18

<210> SEQ ID NO 60
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t

<400> SEQUENCE: 60
gacagcacct acagcctcnn sagcnnsctg acgctgagca aagc                     44

<210> SEQ ID NO 61
<211> LENGTH: 18
<212> TYPE: DNA
<213> ORGANISM: Artificial Sequence
<220> FEATURE:
<223> OTHER INFORMATION: Synthetic

<400> SEQUENCE: 61
gtagagtcct gaggactg                                                  18

<210> SEQ ID NO 62
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
```

```
<222> LOCATION: (25)..(26)
<223> OTHER INFORMATION: n is a, c, g, or t

<400> SEQUENCE: 62
cagtcctcag gactctacnn sctcnnsagc gtggtgaccg tgccc          45

<210> SEQ ID NO 63
<211> LENGTH: 35
<212> TYPE: DNA
<213> ORGANISM: Artificial Sequence
<220> FEATURE:
<223> OTHER INFORMATION: Synthetic

<400> SEQUENCE: 63
tggtggccgg cctggccaca agatttgggc tcaac                    35

<210> SEQ ID NO 64
<211> LENGTH: 46
<212> TYPE: DNA
<213> ORGANISM: Artificial Sequence
<220> FEATURE:
<223> OTHER INFORMATION: Synthetic

<400> SEQUENCE: 64
gtgtaagctt accatgggtg tgcccactca ggtcctgggg ttgctg        46

<210> SEQ ID NO 65
<211> LENGTH: 18
<212> TYPE: DNA
<213> ORGANISM: Artificial Sequence
<220> FEATURE:
<223> OTHER INFORMATION: Synthetic

<400> SEQUENCE: 65
gaggctgtag gtgctgtc                                       18

<210> SEQ ID NO 66
<211> LENGTH: 41
<212> TYPE: DNA
<213> ORGANISM: Artificial Sequence
<220> FEATURE:
<223> OTHER INFORMATION: Synthetic

<400> SEQUENCE: 66
agcacctaca gcctcctgag ctcgctgacg ctgagcaaag c             41

<210> SEQ ID NO 67
<211> LENGTH: 27
<212> TYPE: DNA
<213> ORGANISM: Artificial Sequence
<220> FEATURE:
<223> OTHER INFORMATION: Synthetic

<400> SEQUENCE: 67
caatgaattc attaacactc tcccctg                             27

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
gatcgagctc agcttccacc                                     20
```

```
<210> SEQ ID NO 69
<211> LENGTH: 42
<212> TYPE: DNA
<213> ORGANISM: Artificial Sequence
<220> FEATURE:
<223> OTHER INFORMATION: Synthetic

<400> SEQUENCE: 69
cacggtcacc acgctcacga gctcgtagag tcctgaggac tg                          42

<210> SEQ ID NO 70
<211> LENGTH: 18
<212> TYPE: DNA
<213> ORGANISM: Artificial Sequence
<220> FEATURE:
<223> OTHER INFORMATION: Synthetic

<400> SEQUENCE: 70
agcgtggtga ccgtgccc                                                     18

<210> SEQ ID NO 71
<211> LENGTH: 18
<212> TYPE: DNA
<213> ORGANISM: Artificial Sequence
<220> FEATURE:
<223> OTHER INFORMATION: Synthetic

<400> SEQUENCE: 71
cccgaggtcg acgctctc                                                     18

<210> SEQ ID NO 72
<211> LENGTH: 33
<212> TYPE: DNA
<213> ORGANISM: Artificial Sequence
<220> FEATURE:
<223> OTHER INFORMATION: Synthetic

<400> SEQUENCE: 72
tgacccgcct ccacctgagg agacggtgac cag                                    33

<210> SEQ ID NO 73
<211> LENGTH: 33
<212> TYPE: DNA
<213> ORGANISM: Artificial Sequence
<220> FEATURE:
<223> OTHER INFORMATION: Synthetic

<400> SEQUENCE: 73
ggtggaggcg ggtcacgaac tgtggctgca cca                                    33

<210> SEQ ID NO 74
<211> LENGTH: 46
<212> TYPE: DNA
<213> ORGANISM: Artificial Sequence
<220> FEATURE:
<223> OTHER INFORMATION: Synthetic

<400> SEQUENCE: 74
gtgttctaga gccgccacca tggaatggag ctgggtcttt ctcttc                      46

<210> SEQ ID NO 75
<211> LENGTH: 38
<212> TYPE: DNA
<213> ORGANISM: Artificial Sequence
<220> FEATURE:
<223> OTHER INFORMATION: Synthetic
```

<400> SEQUENCE: 75
gctgagctcc cgcctccacc gcctaccact accagctg        38

<210> SEQ ID NO 76
<211> LENGTH: 33
<212> TYPE: DNA
<213> ORGANISM: Artificial Sequence
<220> FEATURE:
<223> OTHER INFORMATION: Synthetic

<400> SEQUENCE: 76
tgacccgcct ccacctttac ccggagacag gga        33

<210> SEQ ID NO 77
<211> LENGTH: 33
<212> TYPE: DNA
<213> ORGANISM: Artificial Sequence
<220> FEATURE:
<223> OTHER INFORMATION: Synthetic

<400> SEQUENCE: 77
ggtggaggcg ggtcaaagaa ggtggtgtac ggc        33

<210> SEQ ID NO 78
<211> LENGTH: 33
<212> TYPE: DNA
<213> ORGANISM: Artificial Sequence
<220> FEATURE:
<223> OTHER INFORMATION: Synthetic

<400> SEQUENCE: 78
tgtgtgagtt ttgtctgagg agacggtgac cag        33

<210> SEQ ID NO 79
<211> LENGTH: 33
<212> TYPE: DNA
<213> ORGANISM: Artificial Sequence
<220> FEATURE:
<223> OTHER INFORMATION: Synthetic

<400> SEQUENCE: 79
gacaaaactc acacacgaac tgtggctgca cca        33

<210> SEQ ID NO 80
<211> LENGTH: 41
<212> TYPE: DNA
<213> ORGANISM: Artificial Sequence
<220> FEATURE:
<223> OTHER INFORMATION: Synthetic

<400> SEQUENCE: 80
gctgagctcg tgtgagtttt gtcgcctacc actaccagct g        41

<210> SEQ ID NO 81
<211> LENGTH: 33
<212> TYPE: DNA
<213> ORGANISM: Artificial Sequence
<220> FEATURE:
<223> OTHER INFORMATION: Synthetic

<400> SEQUENCE: 81
ggtatgcgtc ttatctttac ccggagacag gga        33

<210> SEQ ID NO 82
<211> LENGTH: 33
<212> TYPE: DNA
<213> ORGANISM: Artificial Sequence
<220> FEATURE:
<223> OTHER INFORMATION: Synthetic

<400> SEQUENCE: 82
gataagacgc ataccaagaa ggtggtgtac ggc    33

<210> SEQ ID NO 83
<211> LENGTH: 18
<212> TYPE: DNA
<213> ORGANISM: Artificial Sequence
<220> FEATURE:
<223> OTHER INFORMATION: Synthetic

<400> SEQUENCE: 83
gacaaaactc acacatgc    18

<210> SEQ ID NO 84
<211> LENGTH: 52
<212> TYPE: DNA
<213> ORGANISM: Artificial Sequence
<220> FEATURE:
<223> OTHER INFORMATION: Synthetic

<400> SEQUENCE: 84
cttctgcgtg tagtggctgt gcagagcctc atgcagcacg gagcatgaga ag    52

<210> SEQ ID NO 85
<211> LENGTH: 52
<212> TYPE: DNA
<213> ORGANISM: Artificial Sequence
<220> FEATURE:
<223> OTHER INFORMATION: Synthetic

<400> SEQUENCE: 85
cttctcatgc tccgtgctgc atgaggctct gcacagccac tacacgcaga ag    52

<210> SEQ ID NO 86
<211> LENGTH: 19
<212> TYPE: DNA
<213> ORGANISM: Artificial Sequence
<220> FEATURE:
<223> OTHER INFORMATION: Synthetic

<400> SEQUENCE: 86
tttacccgga gacagggag    19

<210> SEQ ID NO 87
<211> LENGTH: 49
<212> TYPE: DNA
<213> ORGANISM: Artificial Sequence
<220> FEATURE:
<223> OTHER INFORMATION: Synthetic

<400> SEQUENCE: 87
tgtgtgagtt ttgtcacaag atttgggctc aactttcttg tccaccttg    49

<210> SEQ ID NO 88
<211> LENGTH: 19
<212> TYPE: DNA
<213> ORGANISM: Artificial Sequence
<220> FEATURE:
<223> OTHER INFORMATION: Synthetic

```
<400> SEQUENCE: 88
ctccctgtct ccgggtaaa                                              19

<210> SEQ ID NO 89
<211> LENGTH: 35
<212> TYPE: DNA
<213> ORGANISM: Artificial Sequence
<220> FEATURE:
<223> OTHER INFORMATION: Synthetic

<400> SEQUENCE: 89
acgcggccca gccggccaag aaggtggtgc tgggc                             35

<210> SEQ ID NO 90
<211> LENGTH: 34
<212> TYPE: DNA
<213> ORGANISM: Artificial Sequence
<220> FEATURE:
<223> OTHER INFORMATION: Synthetic

<400> SEQUENCE: 90
ggtcaggaag ctgcccgcgt tgcccaggat cttg                              34

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
ggcagcttcc tgaccaag                                               18

<210> SEQ ID NO 92
<211> LENGTH: 60
<212> TYPE: DNA
<213> ORGANISM: Artificial Sequence
<220> FEATURE:
<223> OTHER INFORMATION: Synthetic

<400> SEQUENCE: 92
tgtgtgagtt ttgtcacaag atttgggctc cgggtctgcc gcggccagca ccacgatgtc  60

<210> SEQ ID NO 93
<211> LENGTH: 18
<212> TYPE: DNA
<213> ORGANISM: Artificial Sequence
<220> FEATURE:
<223> OTHER INFORMATION: Synthetic

<400> SEQUENCE: 93
gacaaaactc acacatgc                                               18

<210> SEQ ID NO 94
<211> LENGTH: 93
<212> TYPE: DNA
<213> ORGANISM: Artificial Sequence
<220> FEATURE:
<223> OTHER INFORMATION: Synthetic

<400> SEQUENCE: 94
gcgggtttaa actcaatcca tatcgtagta gtagccccca tcgtagtcgt agtagtctcc  60
accgcctcca cctttacccg gagacaggga gag                               93
```

BISPECIFIC MULTIVALENT FUSION PROTEINS

CROSS-REFERENCE TO RELATED APPLICATIONS

This patent application is a U.S. National Phase of International Patent Application No. PCT/US2015/066131, filed Dec. 16, 2015, which claims the benefit of U.S. Provisional Patent Application No. 62/138,003, filed Mar. 25, 2015, each of which is incorporated herein by reference in its entirety.

STATEMENT REGARDING FEDERALLY SPONSORED RESEARCH AND DEVELOPMENT

This invention was made with Government support under project number ZIA BC 010701 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 103,224 Byte ASCII (Text) file named "730340 ST25.TXT," created Sep. 22, 2017.

BACKGROUND OF THE INVENTION

The desire exists for highly effective compositions and methods to prophylactically or therapeutically inhibit viral infections, such as an HIV-1 infection.

BRIEF SUMMARY OF THE INVENTION

The invention provides a construct comprising two fusion proteins of A-(optional linker)-C (Formula III), and two fusion proteins of B-(optional linker)-D-(optional linker)-E (Formula IV), wherein A is an antibody or antibody fragment, B is a single domain CD4, C is an immunoglobulin light chain constant region, D is an immunoglobulin heavy chain constant region, and E is a defucosylated Fc region or portion thereof.

The invention provides a construct comprising two fusion proteins of A-(optional linker)-C (Formula III), and two fusion proteins of B-(optional linker)-D-(optional linker)-E-(optional linker)-B (Formula II), wherein A is an antibody or antibody fragment, B is a single domain CD4, C is an immunoglobulin light chain constant region, D is an immunoglobulin heavy chain constant region, and E is a defucosylated Fc region or portion thereof.

The invention provides a construct comprising two fusion proteins of A-(optional linker)-C-(optional linker)-B (Formula I), and two fusion proteins of B-(optional linker)-D-(optional linker)-E-(optional linker)-B (Formula II), wherein A is an antibody or antibody fragment, B is a single domain CD4, C is an immunoglobulin light chain constant region, D is an immunoglobulin heavy chain constant region, and E is a defucosylated Fc region or portion thereof.

The invention provides a construct having a structure depicted in FIG. 1, wherein A is an antibody or antibody fragment, B is a single domain CD4, C is an immunoglobulin light chain constant region, D is an immunoglobulin heavy chain constant region, and E is a defucosylated Fc region or portion thereof, and straight lines are optional linker sequences; and wherein C and D are optionally joined via disulfide bonds, and the two Fc regions are optionally joined via disulfide bonds.

The invention provides a construct comprising two fusion proteins of A-(optional linker)-C (Formula III), and two fusion proteins of B-(optional linker)-D-(optional linker)-E-(optional linker)-B (Formula II), wherein A is an antibody or antibody fragment and B is a single domain CD4, wherein C is a modified immunoglobulin light chain constant region comprising one of SEQ ID NOs: 29-34, wherein D is modified immunoglobulin heavy chain constant region comprising one of SEQ ID NOs: 22-27, and wherein E is an Fc region or portion thereof.

Additionally, the invention provides a composition comprising the inventive construct and a carrier; a conjugate comprising the construct and a cytotoxic agent; and a composition comprising the conjugate. Also provided is a method of prophylactically or therapeutically inhibiting a viral infection in a cell or host comprising administering to the cell or host the construct, the conjugate, or a composition thereof, as well as a method of eradicating viral-infected cells in a subject comprising administering the conjugate or the composition thereof to the subject.

BRIEF DESCRIPTION OF THE SEVERAL VIEWS OF THE DRAWINGS

FIGS. 4A-B demonstrate that binding of Env-positive cells (293T-SC gp160) and Env-negative cells (293T). FIG. 4C demonstrates the results of an ADCC reporter assay (Jurkat T cells engineered to express human FcγRIIIa).

FIG. 4D demonstrates the results a PBMC-based ADCC assay at construct concentration of 100 nM.

DETAILED DESCRIPTION OF THE INVENTION

Figure 1:
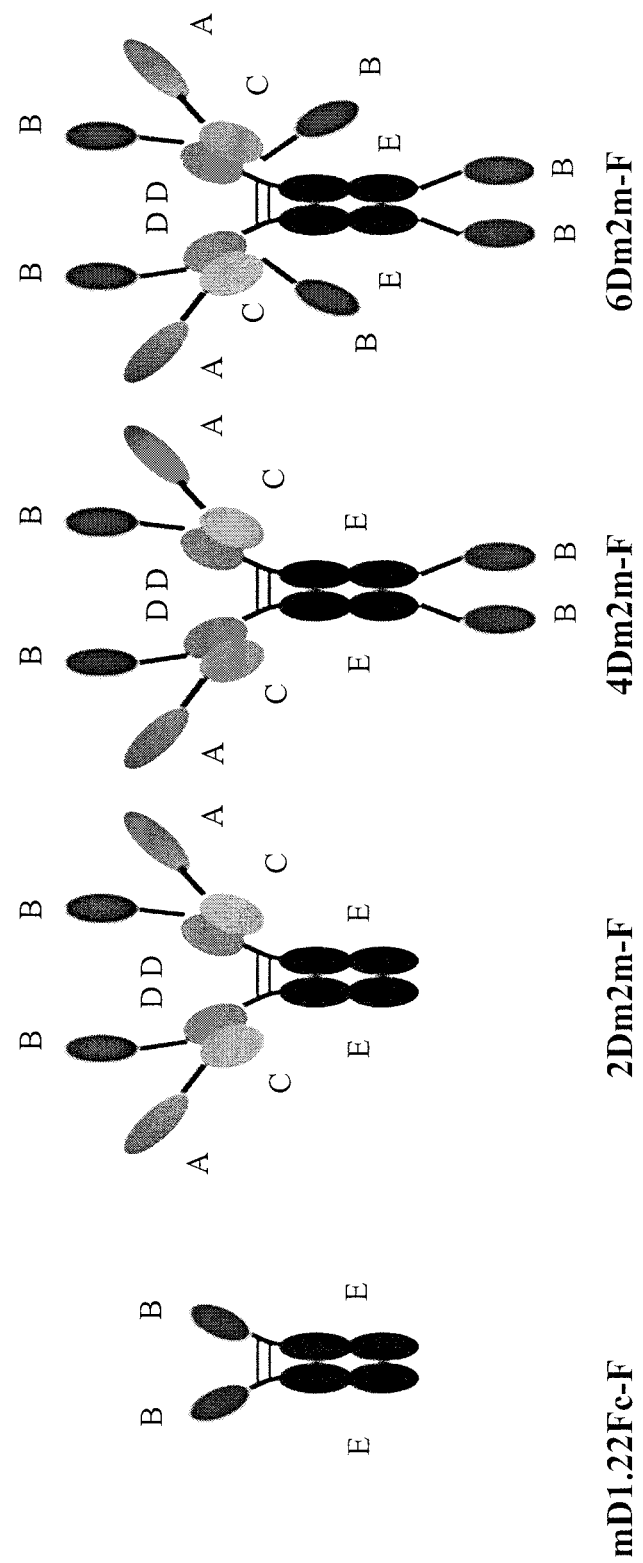
FIG. 1 is a depiction of constructs containing multiple fusion proteins, wherein A denotes an antibody or antibody fragment (e.g., m36.4), B denotes a single domain CD4, C denotes a light chain constant region, D denotes a heavy chain constant region, and E denotes a defucosylated Fc region or portion thereof. Straight lines connecting the regions denote linker sequences. The line represents optional bonds.

The invention provides a construct comprising two or more fusion proteins of Formulas (I)-(IV):

| | |
|---|---|
| A-(optional linker)-C-(optional linker)-B | (Formula I) |
| B-(optional linker)-D-(optional linker)-E-(optional linker)-B | (Formula II) |
| A-(optional linker)-C | (Formula III) |
| B-(optional linker)-D-(optional linker)-E | (Formula IV), | wherein A denotes an antibody or antibody fragment (e.g., Fab, scFv, eAd, etc.), B denotes a single domain CD4 (referred to as mD1), C denotes an immunoglobulin light chain constant region (e.g., human IgG1 kappa light chain constant region), D denotes an immunoglobulin heavy chain constant region (e.g., human IgG1 heavy chain constant region), and E denotes an Fc region or a portion thereof (e.g., the Fc region from human IgG1 which can be defucoyslated).

The antibody or antibody fragment can be any suitable antibody or antibody fragment. The antibody or antibody fragment can bind to an HIV envelope glycoprotein. In one embodiment, the antibody or antibody fragment is a Fab, scFv, or dAb. Preferably, the antibody is a single-domain antibody (a.k.a. "domain antibody ("dAb") or "engineered antibody domain" ("eAd")), which is an antibody fragment consisting of a single monomeric variable antibody domain from the heavy or light chains. For example, the eAd can comprise SEQ ID NO: 10, SEQ ID NO: 11, SEQ ID NO: 12, SEQ ID NO: 13, or SEQ ID NO: 14, also referenced herein as the m36, m36.1, m36.2, m36.4, or m36.5 antibodies, respectively. Suitable antibody or antibody fragments are described in International Patent Application Publication WO 2014/150748.

The single domain CD4 can be any suitable single domain CD4. In one embodiment, the single domain CD4 comprises, consists essentially of, or consists of the amino acid sequence of SEQ ID NO: 1, SEQ ID NO: 2, or variants of SEQ ID NO: 1 or SEQ ID NO: 2 with up to 20 (e.g., 0, 1, 2, 3, 4, 5, 6, 7, 8, 9, 10, 11, 12, 13, 14, 15, 16, 17, 18, 19, or 20) additions, deletions, substitutions, or insertions. In another embodiment, the single domain D4 comprises SEQ ID NO: 1 or SEQ ID NO: 2 with up to 10 additions, deletions, substitutions, or insertions, wherein the polypeptide does not comprise SEQ ID NO: 4. Alternatively, the single domain CD4 can comprise SEQ ID NO: 3. Suitable single domain CD4 are described in International Patent Application Publication WO 2014/150748.

The immunoglobulin light chain constant region can be any suitable immunoglobulin light chain constant region (CL). In one embodiment, the immunoglobulin light chain constant region is a human IgG1 kappa light chain constant region (CK). Preferably, the CL has been modified to stabilize interaction with CH1. Suitable modifications include one or two substitutions at position 69 and/or position 71 of the CK sequence (e.g., SEQ ID NO: 28). For example, the Ser at position 69 of SEQ ID NO: 28 can be substituted with Phe, Ala, Leu, Val, or Glu (or remain unchanged) and/or the Thr at position 71 of SEQ ID NO: 28 can be substituted with Trp, Ser, Arg, Ala, or Val (or remain unchanged). Exemplary modified CK includes, but is not limited to, the amino acid sequences of SEQ ID NOs: 29-34. Preferably, the modified CK comprises the amino acid sequence of SEQ ID NO: 31.

The immunoglobulin heavy chain constant region can be any suitable immunoglobulin heavy chain constant region. In one embodiment, the immunoglobulin heavy chain constant region is a human IgG1 heavy chain constant region, such as a human IgG1 heavy chain constant domain 1 (CH1) (e.g., the CH1 of SEQ ID NO: 21). Preferably, the CH1 has been modified to stabilize interaction with CL (e.g., CK). Suitable modifications include one or two substitutions at position 64 and/or position 66 of the CH1 sequence (e.g., SEQ ID NO: 21). For example, the Ser at position 64 of SEQ ID NO: 21 can be substituted with Tyr, Asn, Glu, Thr, Lys, or Met (or remain unchanged) and/or the Ser at position 66 of SEQ ID NO: 21 can be substituted with Leu, Tyr, Val, or Phe (or remain unchanged). Exemplary modified CH1 includes, but is not limited to, the amino acid sequences of SEQ ID NOs: 22-27. Preferably, the modified CH1 comprises the amino acid sequence of SEQ ID NO: 24.

The Fc region or portion thereof can be any suitable Fc region or portion thereof. In one embodiment, the Fc region or portion thereof is an immunoglobulin Fc region or portion thereof (e.g., the CH2 or CH3 region), especially the Fc region of a human immunoglobulin, such as a human IgG1 Fc region. Examples of an Fc region or portion thereof for use in the invention include, but are not limited to, the amino acid sequence of SEQ ID NO: 5 and SEQ ID NO: 6. The Fc region or portion thereof also can include modifications to increase antibody binding to FcRn and half-life in vivo. Suitable modifications include one or two substitutions at positions 208 and/or position 214 of SEQ ID NO: 5. For example, the Met at position 208 of SEQ ID NO: 5 can be substituted with Leu (or remain unchanged) and/or the Asn at position 215 SEQ ID NO: 5 can be substituted with Leu (or remain unchanged). An exemplary Fc region with the Met208Leu and Asn214Leu substitutions corresponds to SEQ ID NO: 51.

Preferably, the Fc region has been defucosylated. Defucosylation refers to the removal of one or more fucose residues, e.g., from N-glycans, O-glycans, and glycolipids. For example, the amount of fucose in the defucosylated Fc region or portion thereof can be from about 0% to about 80% (e.g., about 5%, about 10%, about 15%, about 20%, about 25%, about 30%, about 35%, about 40%, about 45%, about 50%, about 55%, about 60%, about 65%, about 70%, about 75%, or any range of values thereof). The amount of fucose is determined by calculating the average amount of fucose within the sugar chain at Asn297, relative to the sum of all glycostructures attached to Asn297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues). However, Asn297 may also be located about +/−3 amino acids upstream or downstream of position 297, i.e., between positions 294 and 300, due to minor sequence variations. See, e.g., U.S. Patent Publication Nos. 2003/0157108, 2004/0093621, 2003/0115614, 2002/0164328, 2004/0093621, 2004/0132140, 2004/0110704, 2004/0110282, and 2004/0109865; International Patent Application Publication Nos. WO 2000/61739, WO 2001/29246, WO 2003/085119, WO 2003/084570, WO 2005/035586, WO 2005/035778, WO2005/053742, WO2002/031140, Okazaki et al., *J. Mol. Biol.*, 336: 1239-1249 (2004); and Yamane-Ohnuki et al., *Biotech. Bioeng.*, 87: 614 (2004).

The fucose residues can be removed from the Fc region or portion thereof by any suitable means. For example, the defucosylated Fc region or portion thereof can be produced in a cell line such as Lec13 CHO cells deficient in protein fucosylation (see Ripka et al., *Arch. Biochem. Biophys.* 249: 533-545 (1986); U.S. Patent Application No. 2003/0157108; and International Patent Application Publication No. WO 2004/056312), knockout cell lines, such as alpha-1,6-fucosyltransferase gene, FUT8, knockout CHO cells (see, e.g., Yamane-Ohnuki et al. *Biotech. Bioeng.*, 87: 614 (2004); Kanda et al., *Biotechnol. Bioeng.*, 94(4): 680-688 (2006); and International Patent Application Publication No. WO 2003/085107), or by adding an α-mannosidase inhibitor (e.g., kifunensine) to cell culture as described in the Examples.

The optional linker refers to a flexible molecular connection, such as a flexible polypeptide chain. The linker can be any suitable linker of any length, but is preferably at least about 15 (e.g., at least about 20, at least about 25, at least about 30, at least about 35, at least about 40, at least about 45, at least about 50, or ranges thereof) amino acids in length. In one embodiment, the linker is an amino acid sequence that is naturally present in immunoglobulin molecules of the host, such that the presence of the linker would not result in an immune response against the linker sequence by the mammal. Examples of suitable linkers include, but are not limited to, linkers that comprise one or more (e.g., two, three, four, five, six, seven, eight, nine, or ten) $G_4S$ motifs, such as the linkers of SEQ ID NOs: 9-11 and 36. Alternatively, the linker can be derived from the human IgG1 hinge (e.g., SEQ ID NO: 35). Suitable linkers are described in International Patent Application Publication WO 2014/150748.

In one embodiment, two fusion proteins of Formula I above and two fusion proteins of Formula II above can be assembled into a single construct, as depicted in FIG. 1 (6Dm2m). In such a construct, the fusion protein of Formula I can comprise SEQ ID NO: 20 and the fusion protein of Formula II can comprise SEQ ID NO: 19.

In another embodiment, two fusion proteins of Formula III above and two fusion proteins of B-(optional linker)-D-(optional linker)-E (Formula IV) can be assembled into a single construct, as depicted in FIG. 1 (2Dm2m). In such a construct, the fusion protein of Formula III can comprise SEQ ID NO: 16 and the fusion protein of Formula IV can comprise SEQ ID NO: 15.

Figure 7:
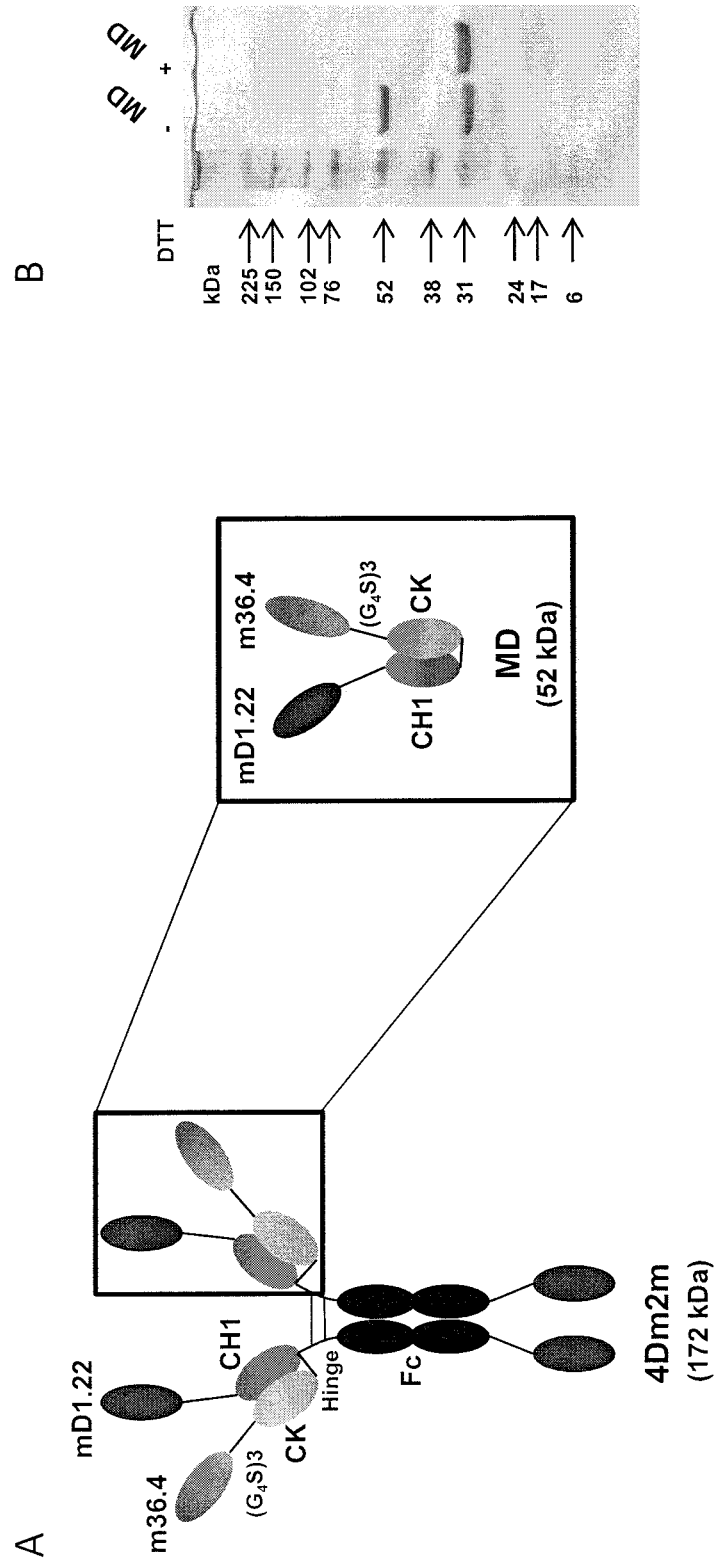
FIGS. 7A-D are images demonstrating inefficient CH1-CK heterodimerization. (A) Schematic representation of 4Dm2m and MD (an mD1.22-CH1/m36.4-CK heterodimer). The short line connecting the C termini of CH1 and CK denotes the inter-chain disulfide bridge. Calculated molecular masses are shown in parentheses. (B) Nonreducing and reducing SDS-PAGE of MD. Molecular masses of standards are shown on the left. (C) Size-exclusion chromatography of MD. The arrows at the top indicate the elution volumes of the molecular mass standards in PBS (pH 7.4): carbonic anhydrase (29 kDa), ovalbumin (44 kDa), and conalbumin (75 kDa). (D) High-resolution mass spectrometry. Mass spectra were shown with deconvoluted mass for each peak indicated at the top.
Figure 7:
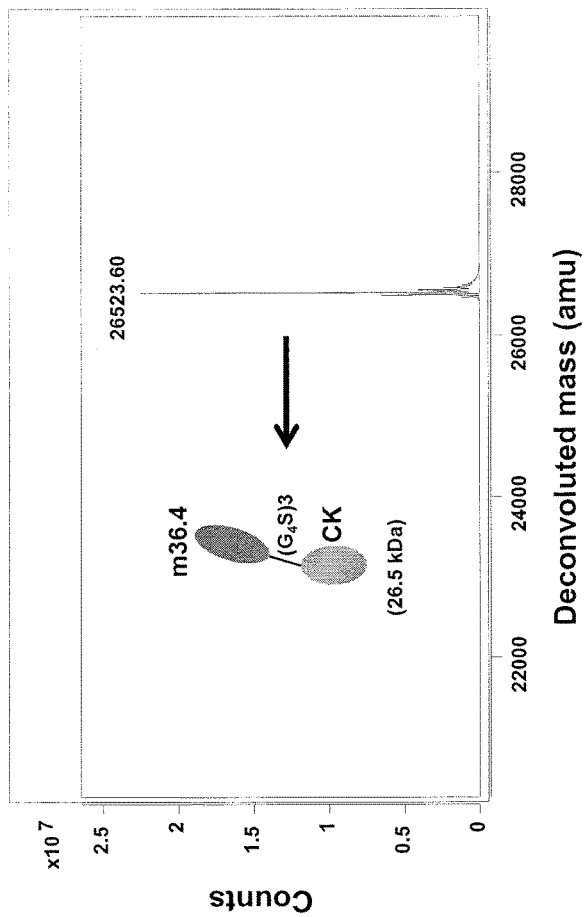
Figure 7:
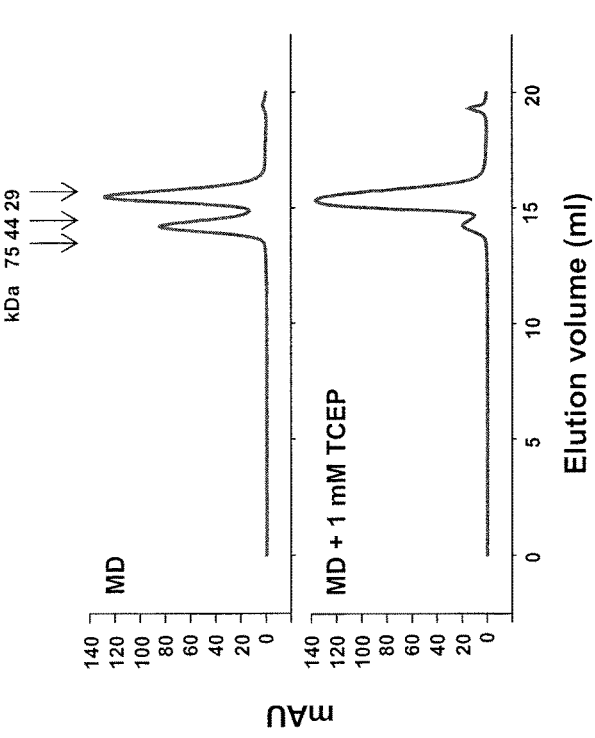

In another embodiment, two fusion proteins of Formula II above and two fusion proteins of A-(optional linker)-C (Formula III) can be assembled into a single construct, as depicted in FIGS. 1 and 7A (4Dm2m). Exemplary constructs include those listed in the table below:

| Construct | Formula II | Formula III |
|---|---|---|
| 4Dm2m | SEQ ID NO: 17 | SEQ ID NO: 18 |
| LSEV | SEQ ID NO: 39 | SEQ ID NO: 40 |
| LSEVs | SEQ ID NO: 41 | SEQ ID NO: 42 |
| LSEVh | SEQ ID NO: 43 | SEQ ID NO: 44 |
| LSEV-LS | SEQ ID NO: 45 | SEQ ID NO: 46 |
| LSEVs-LS | SEQ ID NO: 47 | SEQ ID NO: 48 |
| LSEVh-LS | SEQ ID NO: 49 | SEQ ID NO: 50 |

As described in the Examples, the LSEV constructs (i.e., LSEV, LSEVs, LSEVh, LSEV-LS, LSEVs-LS, and LSEVh-LS) are variants of 4Dm2m that have a stabilized CH1-CL region. Each of the LSEV constructs contains a modified immunoglobulin light chain constant region (corresponding to C in Formula III) comprising SEQ ID NO: 31, and a modified immunoglobulin heavy chain constant region (corresponding to D in Formula II) comprising SEQ ID NO: 24.

The LSEVs, LSEVh, LSEVs-LS, and LSEVh-LS constructs have shorter polypeptide linkers than 4Dm2m. In particular, the linkers of the LSEVs and LSEVs-LS constructs are a single copy of GGGGS (SEQ ID NO: 36). The linkers of the LSEVh and LSEVh-LS constructs are the human IgG1 hinge sequence DKTHT (SEQ ID NO: 35).

The LSEV-LS, LSEVs-LS, and LSEVh-LS constructs contain a modified Fc region with Met280Leu and Asn214Leu substitutions corresponding to SEQ ID NO: 51. These amino acid mutations result in enhanced antibody binding to Fc neonatal receptor (FcRn) and increased half-lives of the LSEV-LS constructs in vivo.

The individual fusion proteins can be joined in the manner typical of IgG type constructs, such as by disulfide bridges between the constant heavy and constant light regions and between the Fc regions. Two or more fusion proteins joined as a single construct desirably can provide a multivalent (bivalent, tetravalent, or even octavalent) molecule.

Thus, constructs comprising two or more (e.g., two, three, four, five, six, seven, eight, nine, ten, or more) of the fusion proteins also are encompassed by the invention.

In one embodiment, the fusion proteins are assembled (e.g., self-assembled) to form one of the constructs depicted in FIG. 1, wherein A denotes an antibody or antibody fragment (e.g., m36.4 eAd), B denotes a single CD4 domain (e.g., mD1.22), C denotes an immunoglobulin light chain constant region (e.g., CK), D denotes an immunoglobulin heavy chain constant region (e.g., human IgG1 heavy chain constant region), and E denotes an Fc region (e.g., a defucosylated Fc region from human IgG1). An exemplary 4Dm2m construct is depicted in FIG. 7A.

The construct can be PEGylated, or coupled to polymers of similar structure, function and purpose, to confer enhanced stability and half-life. PEGylation can provide increased half-life and resistance to degradation without a loss in activity (e.g., binding affinity) relative to non-PEGylated (e.g., antibody) constructs. Since PEGylation may not be advantageous with respect to some targets, in particular, those epitopes which are sterically-obstructed, the construct should be minimally PEGylated so as not to negatively impact the accessibility to the size-restricted antigen. The construct can be coupled to PEG or PEG-like polymers by any suitable means known in the art. Suitable PEG or PEG-like moieties can be synthetic or naturally occurring and include, but are not limited to, straight or branched chain polyalkylene, polyalkenylene or polyoxyalkylene polymers, or a branched or unbranched polysaccharide, such as a homo- or heteropolysaccharide. Preferred examples of synthetic polymers include straight or branched chain poly (ethylene glycol) (PEG), poly(propylene glycol), or poly (vinyl alcohol) and derivatives or substituted forms thereof. Substituted polymers for linkage to the domain antibodies also include substituted PEG, including methoxy(polyethylene glycol). Naturally occurring polymer moieties which can be used in addition to or in place of PEG include, for example, lactose, amylose, dextran, or glycogen, as well as derivatives thereof.

The fusion proteins of the construct can be multimerized, as for example, hetero- or homodimers, hetero- or homotrimers, hetero- or homotetramers, or higher order hetero- or homomultimers. Multimerization can increase the strength of antigen binding, wherein the strength of binding is related to the sum of the binding affinities of the multiple binding sites. In particular, cysteine residue(s) can be introduced in the amino acid sequence of the fusion proteins, thereby allowing interchain disulfide bond formation in a multimerized form. The homodimeric or heterodimeric (or multimeric) fusion proteins can include combinations of the same or different fusion partners (e.g., eAds), such that more than one epitope can be targeted at a time by the same construct. Such epitopes can be proximally located in the target (e.g., on the HIV target) such that the binding of one epitope facilitates the binding of the multimeric fusion proteins to the second or more epitopes. The epitopes targeted by multimeric fusion proteins also can be distally situated.

Additional peptide sequences can be added to the construct, which act to promote stability, purification, and/or detection. For example, a reporter peptide portion (e.g., green fluorescent protein (GFP), j-galactosidase, or a detectable domain thereof) can be used. Purification-facilitating peptide sequences include those derived or obtained from maltose binding protein (MBP), glutathione-S-transferase (GST), or thioredoxin (TRX). The construct containing the fusion protein also or alternatively can be tagged with an epitope which can be antibody purified (e.g., the Flag epitope, which is commercially available from Kodak (New Haven, Conn.)), a hexa-histidine peptide, such as the tag provided in a pQE vector available from QIAGEN, Inc. (Chatsworth, Calif.), or an HA tag (as described in, e.g., Wilson et al., *Cell,* 37, 767 (1984)).

Conjugates comprising the construct conjugated to cytotoxic agents, such as chemotherapeutic agents, toxin (e.g., an enzymatically active toxin of bacterial, fungal, plant or animal origin, or fragments thereof; a small molecule toxin), radioactive isotopes (i.e., a radioconjugate), or antiviral compounds (e.g., anti-HIV compounds), also are encompassed by the invention. Alternatively, or construct can be co-administered with the cytotoxic agents, antiviral compounds, and the like.

The conjugates comprising cytotoxic agents (e.g., toxins) can be used to target viral (e.g., HIV, such as HIV-1) infected cells and eradicate (destroy) such cells. For example, with a conjugate comprising a cytotoxic agent and a construct, the antibody or antibody fragment portion of the conjugate targets (detects) surface proteins of viral infected cells and the cytotoxic agent portion of the conjugate eradicates (destroys) the targeted viral infected cells. Preferably, the cells to be targeted are HIV (e.g., HIV-1) infected cells and the conjugate detects/targets the HIV (e.g., HIV-1) envelope glycoprotein expressed on the HIV infected cells. Administration of the conjugates can be used to destroy viral (e.g., HIV, such as HIV-1) infected cells in a subject, thereby leading to successful treatment (cure) of the viral (e.g., HIV) infection in the subject. Accordingly, the invention provides a method for treating a viral infection in a subject comprising administering the conjugate to the subject, thereby treating (curing) the viral infection in the subject by destroying the viral-infected cells in the subject.

Methods for conjugating the construct to the cytotoxic agents, chemotherapeutic agents, toxins, antibacterial compounds, and antiviral compounds, and the like are well known in the art. For example, conjugates can be made using a variety of bifunctional protein coupling agents such as N-succinimidyl-3-(2-pyridyidithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Detectable agents, such as fluorescent compounds, also can be added to the construct. Exemplary fluorescent detectable agents include fluorescein, fluorescein isothiocyanate, rhodamine, 5-dimethylamine-1-napthalenesulfonyl chloride, phycoerythrin and the like. The construct also can be derivatized with detectable enzymes, such as alkaline phosphatase, horseradish peroxidase, glucose oxidase and the like. When the construct is derivatized with a detectable enzyme, it is detected by adding additional reagents that the enzyme uses to produce a detectable reaction product. The construct also can be derivatized with biotin, and detected through indirect measurement of avidin or streptavidin binding.

The invention also provides a nucleic acid encoding one or more of the fusion proteins of the construct. The nucleic acid can comprise DNA or RNA, and can be single or double stranded. Furthermore, the nucleic acid can comprise nucleotide analogues or derivatives (e.g., inosine or phophorothioate nucleotides and the like).

The nucleic acid can be provided as part of a construct comprising the nucleic acid and elements that enable delivery of the nucleic acid to a cell, and/or expression of the nucleic acid in a cell. Such elements include, for example, expression vectors, promoters, and transcription and/or translation sequences. Suitable vectors, promoters, transcription/translation sequences, and other elements, as well as methods of preparing such nucleic acids and constructs, are known in the art (e.g., Sambrook et al., supra; and Ausubel et al., supra). The nucleic acid can be naturally-occurring or synthetic (i.e., non-naturally occurring, such as a recombinant nucleic acid or cDNA).

The invention further provides a recombinant vector comprising the nucleic acid. Examples of suitable vectors include plasmids (e.g., DNA plasmids), yeast (e.g., *Saccharomyces*), and viral vectors, such as poxvirus, retrovirus, adenovirus, adeno-associated virus, herpes virus, polio virus, alphavirus, baculorvirus, and Sindbis virus. When the vector is a plasmid (e.g. DNA plasmid), the plasmid can be complexed with chitosan.

When the vector is for administration to a host (e.g., human), the vector preferably has a low replicative efficiency in a target cell (e.g., no more than about 1 progeny per cell or, more preferably, no more than 0.1 progeny per cell are produced). Replication efficiency can readily be determined empirically by determining the virus titer after infection of the target cell.

The conjugate or construct can be administered to a mammal in the form of a cell comprising a nucleic acid encoding the one or more fusion proteins of the construct, optionally in the form of a vector. Thus, the invention also provides a cell comprising a vector or nucleic acid encoding the one or more fusion proteins from which the one or more fusion proteins of the construct desirably is secreted. Any suitable cell can be used. Examples include host cells, such as *E. coli* (e.g., *E. coli* Tb-1, TG-2, DH5a, XL-Blue MRF' (Stratagene), SA2821, and Y1090), *Bacillus subtilis, Salmonella typhimurium, Serratia marcescens, Pseudomonas* (e.g., *P. aerugenosa*), *N. grassa*, insect cells (e.g., Sf9, Ea4), yeast (*S. cerevisiae*) cells, and cells derived from a mammal, including human cell lines. Specific examples of suitable eukaryotic cells include VERO, HeLa, 3T3, Chinese hamster ovary (CHO) cells, W138 BHK, COS-7, and MDCK cells. Alternatively and preferably, cells from a mammal, such as a human, to be treated in accordance with the methods described herein can be used as host cells. In one embodiment, the cell is a human B cell.

Methods of introducing vectors into isolated host cells and the culture and selection of transformed host cells in vitro are known in the art and include the use of calcium chloride-mediated transformation, transduction, conjugation, triparental mating, DEAE, dextran-mediated transfection, infection, membrane fusion with liposomes, high velocity bombardment with DNA-coated microprojectiles, direct microinjection into single cells, and electroporation (see, e.g., Sambrook et al., supra, Davis et al., *Basic Methods in Molecular Biology* (1986), and Neumann et al., *EMBO J.* 1, 841 (1982)). Desirably, the cell comprising the vector or nucleic acid expresses the nucleic acid encoding the construct or fusion proteins thereof such that the nucleic acid sequence is transcribed and translated efficiently by the cell.

The construct, conjugate, nucleic acid, vector, or cell can be isolated. The term "isolated" as used herein encompasses compounds or compositions that have been removed from a biological environment (e.g., a cell, tissue, culture medium, body fluid, etc.) or otherwise increased in purity to any degree (e.g., isolated from a synthesis medium). Isolated compounds and compositions, thus, can be synthetic or naturally produced.

The construct, conjugate, nucleic acid, vector, or cell can be administered to any host (e.g., mammal, preferably a human) in need thereof. As a result of administration of the conjugate, nucleic acid, vector, or cell to the mammal, viral infection (e.g., HIV infection) of the mammal is inhibited. The inventive method can prophylactically or therapeutically inhibit infection by any type of HIV, but preferably inhibits HIV-1 and/or HIV-2 infection. The inventive method can be used to inhibit infection by any HIV group (e.g., groups M and/or O), and subtype (e.g., clades A, B, C, D, E, EA, F, and/or G).

Additionally, the construct, conjugate, nucleic acid, vector, or cell can be used to inhibit a broad range of viruses (see, e.g., Principles of Virology: Molecular Biology, Pathogenesis, and Control, Flint et al., eds., ASM Press: Washington, D.C. (2000), particularly Chapter 19). Examples of viruses that may be treated in accordance with the invention include, but are not limited to, Type C and Type D retroviruses, HTLV-1, HTLV-2, FIV, FLV, SIV, MLV, BLV, BIV, equine infectious virus, anemia virus, avian sarcoma viruses, such as Rous sarcoma virus (RSV), hepatitis type A, B, C, non-A and non-B viruses, arboviruses, varicella viruses, human herpes virus (e.g., HHV-6), measles, mumps, filovirus (e.g., Ebola, such as Ebola strains Sudan, Zaire, Cote d'Ivoire, and Reston), SARS, influenza, and rubella viruses.

When provided therapeutically, construct, conjugate, nucleic acid, vector, cell, or composition thereof is provided at or after the diagnosis of viral (e.g., HIV) infection.

When provided prophylactically, the construct, conjugate, nucleic acid, vector, cell, or composition thereof is provided in advance of viral (e.g., HIV) infection, such as to patients or subjects who are at risk for being exposed to a virus (e.g., HIV) or who have been newly exposed to a virus (e.g., HIV). Examples of such patients and subjects include, for example, healthcare workers, fetuses, neonates, or infants (e.g., nursing infants) whose mothers are infected or at risk for being infected, intravenous drug users, recipients of blood transfusions, blood products, or transplantation tissue, and other individuals who have been exposed to a body fluid that contains or may contain HIV. The prophylactic administration of the construct, conjugate, nucleic acid, vector, cell, or composition thereof prevents, ameliorates, or delays viral (e.g., HIV) infection. In subjects who have been newly exposed to a virus (e.g., HIV) but who have not yet displayed the presence of the virus (as measured by PCR or other assays for detecting the virus) in blood or other body fluid, efficacious treatment with the construct, conjugate, nucleic acid, vector, cell, or composition thereof partially or completely inhibits or delays the appearance of the virus or minimizes the level of the virus in the blood or other body fluid of the exposed individual.

The efficacy of the construct, conjugate, nucleic acid, vector, cell, or composition thereof can be assessed in various ways well known to the skilled practitioner. For instance, one of ordinary skill in the art will understand that a construct or conjugate of the invention is efficacious in treating or inhibiting a viral (e.g., HIV) infection in a subject by observing that the construct or conjugate reduces viral load or delays or prevents a further increase in viral load. Viral loads can be measured by methods that are known in the art, for example, using PCR assays to detect the presence of viral (e.g., HIV) nucleic acid or antibody assays to detect the presence of viral (e.g., HIV) protein in a sample (e.g., blood or another body fluid) from a subject or patient, or by measuring the level of circulating anti-viral (e.g., anti-HIV) antibodies in the patient. Efficacy of the construct or conjugate treatment also can be determined by measuring the number of CD4+ T cells in the HIV-infected subject. A treatment that delays or inhibits an initial or further decrease in CD4+ T cells in an HIV-positive subject or patient, or that results in an increase in the number of CD4+ T cells in the HIV-positive subject, can be considered efficacious.

The construct, conjugate, nucleic acid, vector, or cell can be formulated as a composition (e.g., pharmaceutical composition) comprising construct, conjugate, nucleic acid, vector, or cell and a carrier (e.g., a pharmaceutically or physiologically acceptable carrier). Furthermore, the construct, conjugate, nucleic acid, vector, or cell of the invention can be used in the methods described herein alone or as part of a pharmaceutical formulation (composition).

Compositions (e.g., pharmaceutical compositions) comprising the construct, conjugate, nucleic acid, vector, or cell can include carriers, thickeners, diluents, buffers, preservatives, surface active agents and the like.

Suitable carriers and their formulations are described in A. R. Gennaro, ed., *Remington: The Science and Practice of Pharmacy* (19th ed.), Mack Publishing Company, Easton, Pa. (1995). Pharmaceutical carriers, include sterile water, saline, Ringer's solution, dextrose solution, and buffered solutions at physiological pH. Typically, an appropriate amount of a pharmaceutically acceptable salt is used in the formulation to render the formulation isotonic. The pH of the formulation is preferably from about 5 to about 8 (e.g., about 5.5, about 6, about 6.5, about 7, about 7.5, and ranges thereof). More preferably, the pH is about 7 to about 7.5. Further carriers include sustained-release preparations, such as semipermeable matrices of solid hydrophobic polymers containing the fusion protein, which matrices are in the form of shaped articles (e.g., films, liposomes, or microparticles). It will be apparent to those persons skilled in the art that certain carriers may be more preferable depending upon, for instance, the route of administration and concentration of composition being administered.

The composition (e.g., pharmaceutical composition) can comprise more than one construct, conjugate, nucleic acid, vector, or cell of the invention. Alternatively, or in addition, the composition can comprise one or more other pharmaceutically active agents or drugs. Examples of such other pharmaceutically active agents or drugs that may be suitable for use in the pharmaceutical composition include anticancer agents (e.g., chemotherapeutic drugs), antibiotics, antiviral drugs, antifungal drugs, cyclophosphamide, and combinations thereof. Suitable antiviral agents (e.g., anti-HIV agents) include, but are not limited to, nucleoside/nucleotide reverse transcriptase inhibitors (e.g., lamivudine, abacavir, zidovudine, stavudine, didanosine, emtricitabine, and tenofovir), non-nucleoside reverse transcriptase inhibitors (e.g., delavirdine, efavirenz, etravirine, and nevirapine), protease inhibitors (e.g., amprenavir, fosamprenavir, atazanavir, darunavir, indinavir, lopinavir, ritonavir, nelfinavir, saquinavir, and tipranavir), fusion or entry inhibitors (e.g., enfuvirtide and maraviroc), integrase inhibitors (e.g., raltegravir), and combination therapies thereof.

Suitable methods of administering a construct, conjugate, nucleic acid, vector, cell, or composition thereof to hosts are known in the art. The host can be any suitable host, such as a mammal (e.g., a rodent, such as a mouse, rat, hamster, or guinea pig, rabbit, cat, dog, pig, goat, cow, horse, primate, or human).

Administration can be topical (including ophthalmical, vaginal, rectal, intranasal, transdermal, and the like), oral, by inhalation, or parenteral (including by intravenous drip or subcutaneous, intracavity, intraperitoneal, or intramuscular injection). Topical intranasal administration refers to the delivery of the compositions into the nose and nasal passages through one or both of the nares and can comprise delivery by a spraying mechanism or droplet mechanism, or through aerosolization of the nucleic acid, vector, or fusion protein. Administration of the compositions by inhalant can be through the nose or mouth via delivery by a spraying or droplet mechanism. Delivery can also be directly to any area of the respiratory system (e.g., lungs) via intubation.

Formulations for topical administration include ointments, lotions, creams, gels, drops, suppositories, sprays, liquids, and powders. Conventional pharmaceutical carriers, aqueous, powder, or oily bases, thickeners, and the like may be necessary or desirable.

If the composition is to be administered parenterally, the administration is generally by injection. Injectables can be prepared in conventional forms, either as liquid solutions or suspensions, solid forms suitable for suspension in liquid prior to injection, or as emulsions. Additionally, parental administration can involve the preparation of a slow-release or sustained-release system, such that a constant dosage is maintained. Preparations for parenteral administration include sterile aqueous or non-aqueous solutions, suspensions, and emulsions. Examples of non-aqueous solvents are propylene glycol, polyethylene glycol, vegetable oils, such as olive oil, and injectable organic esters, such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives also can be present such as, for example, antimicrobials, anti-oxidants, chelating agents, and inert gases, and the like.

Compositions for oral administration include powders or granules, suspensions or solutions in water or non-aqueous media, capsules, sachets, or tablets. Thickeners, flavorings, diluents, emulsifiers, dispersing aids, or binders may be desirable.

Some of the compositions can potentially be administered as a pharmaceutically acceptable acid- or base-addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines.

The construct, conjugate, nucleic acid, vector, or cell can be administered with a pharmaceutically acceptable carrier and can be delivered to the mammal's cells in vivo and/or ex vivo by a variety of mechanisms well-known in the art (e.g., uptake of naked DNA, liposome fusion, intramuscular injection of DNA via a gene gun, endocytosis, and the like).

Additionally, probiotic therapies are envisioned by the present invention. Viable host cells containing the nucleic acid or vector of the invention and expressing the construct or conjugate can be used directly as the delivery vehicle to the desired site(s) in vivo. Preferred host cells for the delivery of the construct or conjugate directly to desired site(s), such as, for example, to a selected body cavity, can comprise bacteria. More specifically, such host cells can comprise suitably engineered strain(s) of lactobacilli, enterococci, or other common bacteria, such as $E.$ $coli$, normal strains of which are known to commonly populate body cavities. More specifically yet, such host cells can comprise one or more selected nonpathogenic strains of lactobacilli, such as those described by Andreu et al., $J.$ $Infect.$ $Dis.$, 171(5), 1237-43 (1995), especially those having high adherence properties to epithelial cells (e.g., vaginal epithelial cells) and suitably transformed using the nucleic acid or vector of the invention.

If ex vivo methods are employed, cells or tissues can be removed and maintained outside the body according to standard protocols known in the art. The compositions can be introduced into the cells via any gene transfer mechanism, such as calcium phosphate mediated gene delivery, electroporation, microinjection, or proteoliposomes. The transduced cells then can be infused (e.g., with a pharmaceutically acceptable carrier) or homotopically transplanted back into the mammal per standard methods for the cell or tissue type. Standard methods are known for transplantation or infusion of various cells into a mammal.

The exact amount of the composition required to treat a viral infection (e.g., HIV infection) will vary from mammal to mammal, depending on the species, age, gender, weight, and general condition of the mammal, the nature of the virus, the existence and extent of viral infection, the particular construct, conjugate, nucleic acid, vector, or cell used, the route of administration, and whether other drugs are included in the regimen. Thus, it is not possible to specify an exact amount for every composition. However, an appropriate amount can be determined by one of ordinary skill in the art using only routine experimentation given the teachings herein. Effective dosages and schedules for administering the nucleic acid molecules, vectors, cells, constructs, or conjugates of the invention can be determined empirically, and making such determinations is within the skill in the art. The dosage ranges for the administration of the compositions are those large enough to produce the desired effect; however, the dosage should not be so large as to cause adverse side effects, such as unwanted cross-reactions, anaphylactic reactions, and the like. Dosage can vary, and can be administered in one or more (e.g., two or more, three or more, four or more, or five or more) doses daily, for one or more days. The composition can be administered before viral (e.g., HIV) infection or immediately upon determination of viral (e.g., HIV) infection and continuously administered until the virus is undetectable.

The construct, conjugate, nucleic acid, vector, cell, or composition thereof is administered to a host (e.g., mammal, such as a human) in an amount effective to prophylactically or therapeutically inhibit an HIV infection. The efficacy of the construct, conjugate, nucleic acid, vector, cell, or composition thereof as an HIV infection inhibitor may be determined by in vivo or in vitro parameters known in the art.

Any suitable dose of the construct, conjugate, nucleic acid, vector, cell, or composition thereof can be administered to a host. The appropriate dose will vary depending upon such factors as the host's age, weight, height, sex, general medical condition, previous medical history, and viral (e.g., HIV) infection progression and can be determined by a clinician. For example, the construct or conjugate can be administered in a dose of about 1 μg/kg to up to 100 mg/kg of body weight or more per day (e.g., 5 μg/kg, 10 μg/kg, 50 μg/kg, 100 μg/kg, 200 μg/kg, 300 μg/kg, 400 μg/kg, 500 μg/kg, 600 μg/kg, 700 μg/kg, 800 μg/kg, 900 μg/kg, 1 mg/kg, 2 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, and ranges thereof) to the host (e.g., mammal, such as a human). Several doses (e.g., 1, 2, 3, 4, 5, 6, or more) can be provided (e.g., over a period of weeks or months).

When the vector is a viral vector, a suitable dose can include about $1 \times 10^5$ to about $1 \times 10^{12}$ (e.g., $1 \times 10^6$, $1 \times 10^7$, $1 \times 10^8$, $1 \times 10^9$, $1 \times 10^{10}$, $1 \times 10^{11}$, and ranges thereof) plaque forming units (pfus), although a lower or higher dose can be administered to a host. For example, about $2 \times 10^8$ pfus can be administered (e.g., in a volume of about 0.5 mL).

The inventive cells can be administered to a host in a dose of between about $1 \times 10^5$ and $2 \times 10^{11}$ (e.g., $1 \times 10^6$, $1 \times 10^7$, $1 \times 10^8$, $1 \times 10^9$, $1 \times 10^{10}$, and ranges thereof) cells per infusion. The cells can be administered in, for example, one to three (e.g., two) infusions. In addition to the administration of the cells, the host can be administered a biological response modifier, such as interleukin 2 (IL-2).

The construct or conjugate can be used in combination with other well-known viral (e.g., HIV) therapies and prophylactic vaccines already in use. The combination of the fusion protein of the invention can generate an additive or a synergistic effect with current treatments. The construct of the invention can be combined with other HIV and AIDS therapies and vaccines, such as highly active antiretroviral therapy (HAART), which comprises a combination of protease inhibitors and reverse transcriptase inhibitors, azidothymidine (AZT), structured treatment interruptions of HAART, cytokine immune enhancement therapy (e.g., interleukin (IL)-2, IL-12, CD40L+IL-12, IL-7, HIV protease inhibitors (e.g., ritonavir, indinavir, and nelfinavir, etc.), and interferons (IFNs)), cell replacement therapy, recombinant viral vector vaccines, DNA vaccines, inactivated virus preparations, immunosuppressive agents, such as Cyclosporin A, cyanovirin therapy (see, e.g., U.S. Pat. No. 6,015,876), scytovirin therapy (see, e.g., U.S. Pat. No. 7,491,798), and griffithsin therapy (see, e.g., U.S. Patent Application Publication 2009-0092557). Such therapies can be administered in the manner already in use for the known treatment providing a therapeutic or prophylactic effect (see, e.g., Silvestri et al. Immune Intervention in AIDS. In: *Immunology of Infectious Disease*, H. E. Kauffman, A. Sher, and R. Ahmed eds., ASM Press, Washington D.C. (2002)).

The following examples further illustrate the invention but, of course, should not be construed as in any way limiting its scope.

Example 1

This example demonstrates the generation of a defucosylated construct of the invention.

A defucosylated bispecific multivalent fusion protein of mD1.22 (SEQ ID NO: 1) and m36.4 (SEQ ID NO: 13, which is an engineered single human antibody domain targeting a CD4i epitope on HIV-1 gp120) as exemplified in FIG. 1 (4Dm2m-F) was prepared by adding the α-mannosidase inhibitor kifunensine to cell culture.

A corresponds to m36.4, B corresponds to mD1.22, C corresponds to a light chain constant region, D corresponds to a heavy chain constant region, and E corresponds to a defucosylated Fc region. 4Dm2m comprises two fusion proteins comprising SEQ ID NO: 17 and two fusion proteins comprising SEQ ID NO: 18.

Figure 2:
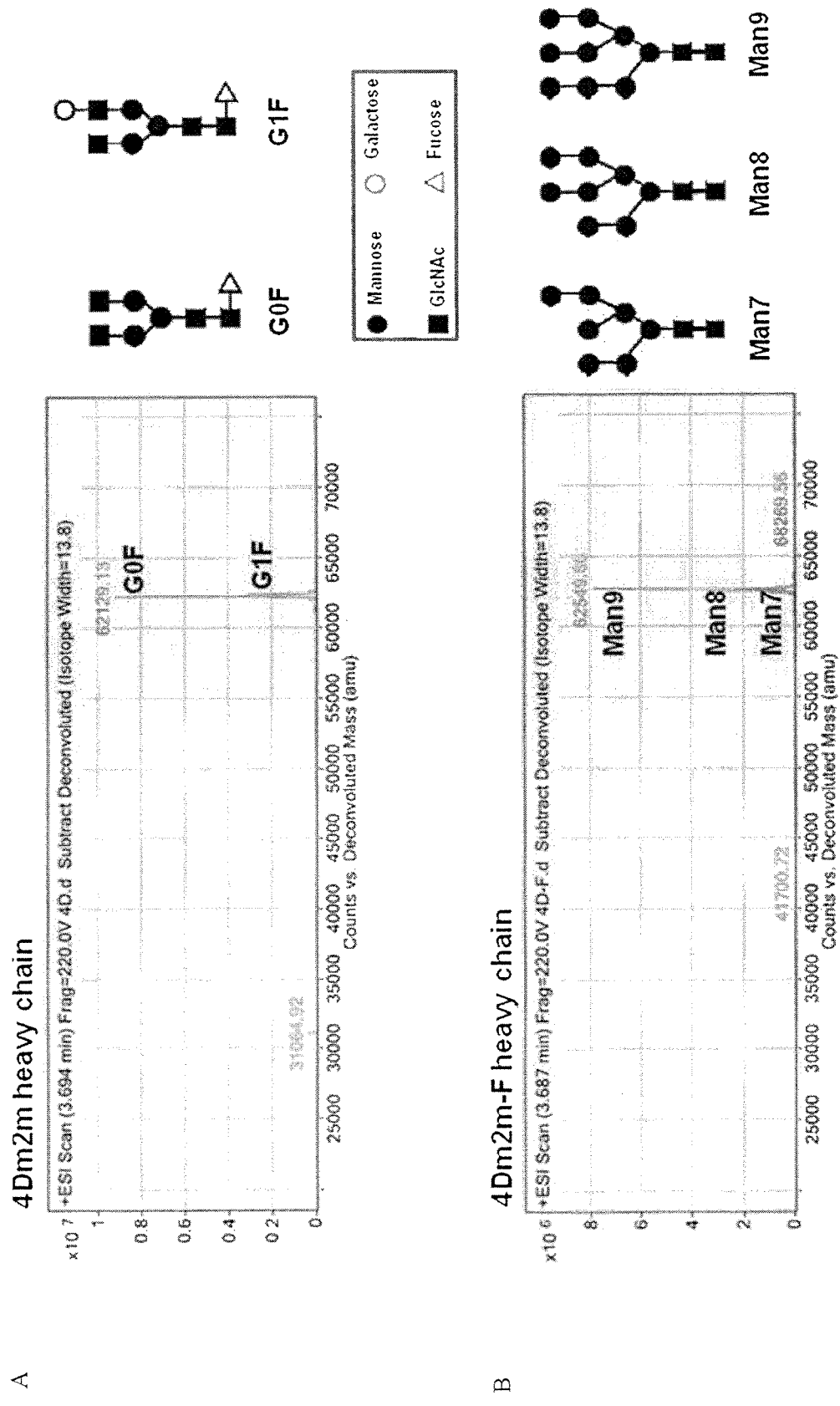
FIGS. 2A-2B are graphs depicting mass spectrometry analysis of sugars in the Fc region of the fully fucosylated 4Dm2m construct (A) and the Fc region of the defucosylated 4Dm2m-F construct (B).

Mass spectrometry analysis confirmed the absence of fucose in 4Dm2m-F (see FIG. 2B) as compared to the fully fucosylated 4Dm2m construct (see FIG. 2A).

Figure 3:
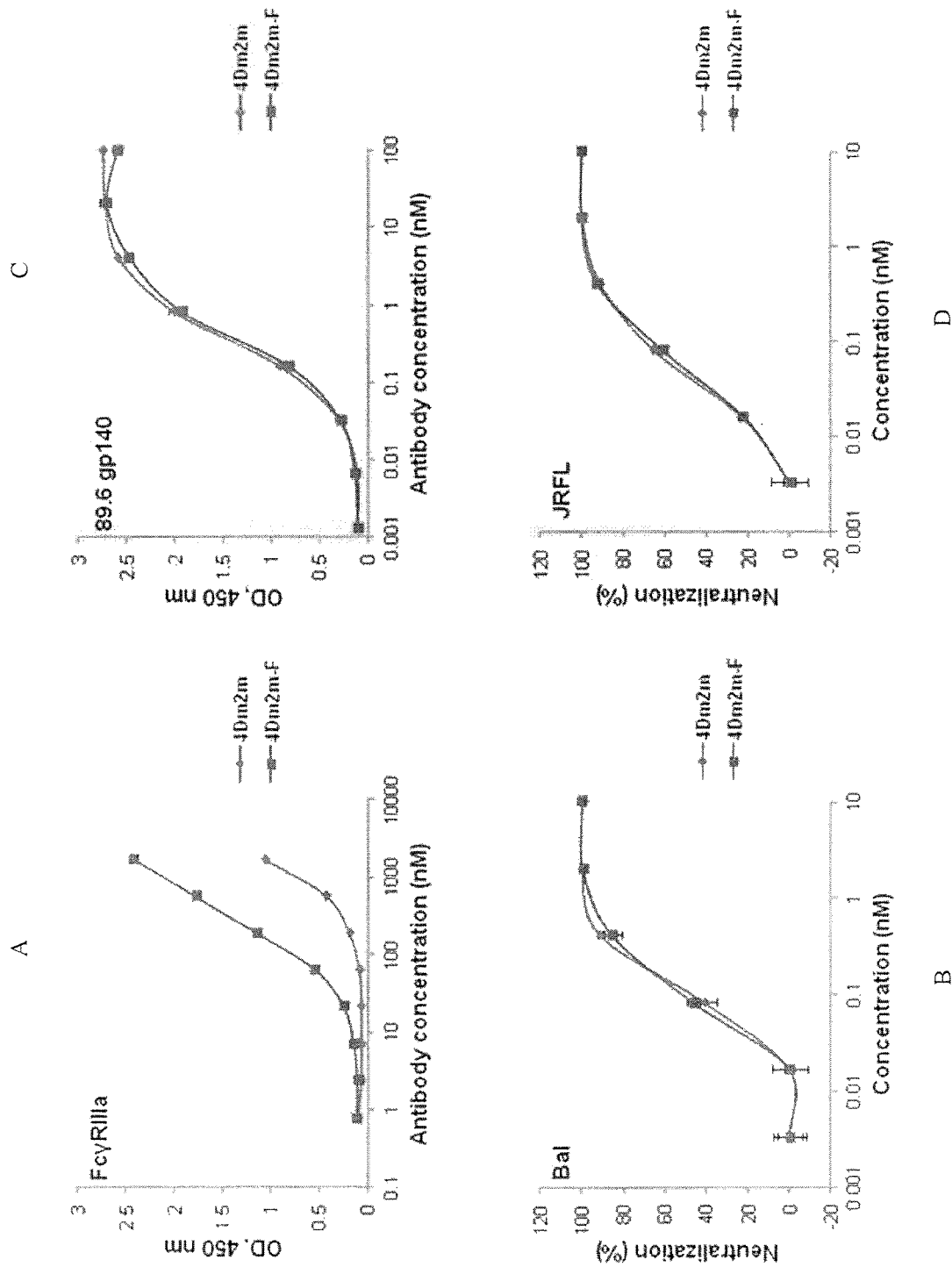
FIGS. 3A-D are graphs demonstrating that the defucosylated 4Dm2m-F construct has increased FcγRIIIa binding relative to the fully fucosylated 4Dm2m construct (A), and that binding and neutralization of HIV-1 Env for the defucosylated 4Dm2m-F construct and fully fucosylated 4Dm2m construct were the same (B-D).
Figure 4:
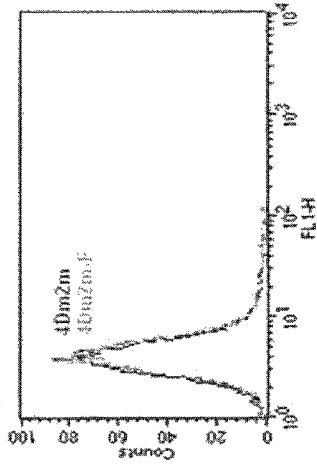
FIGS. 4A-D are graphs demonstrating that the defucosylated 4Dm2m-F construct mediated stronger antibody-dependent cell-mediated cytotoxicity (ADCC) in vitro than the fully fucosylated 4Dm2m construct.
Figure 4:
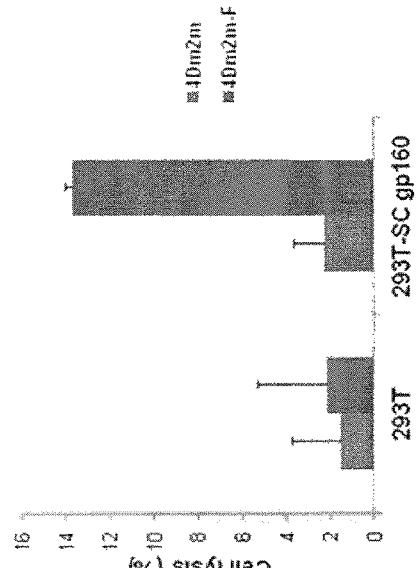
Figure 4:
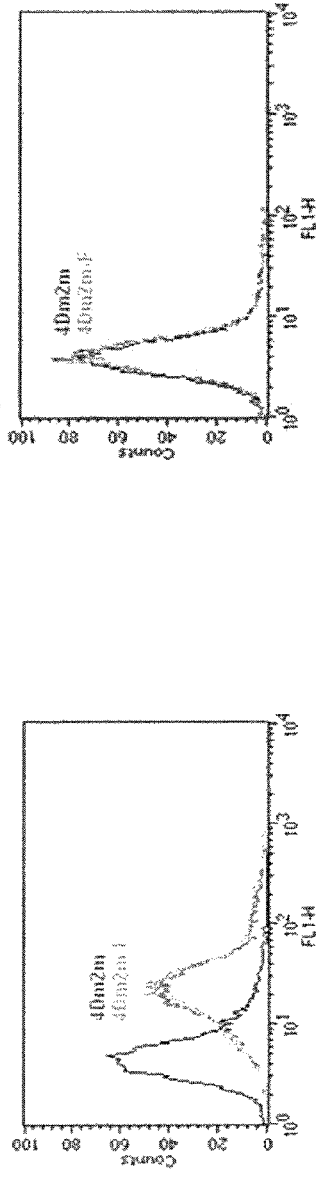
Figure 4:
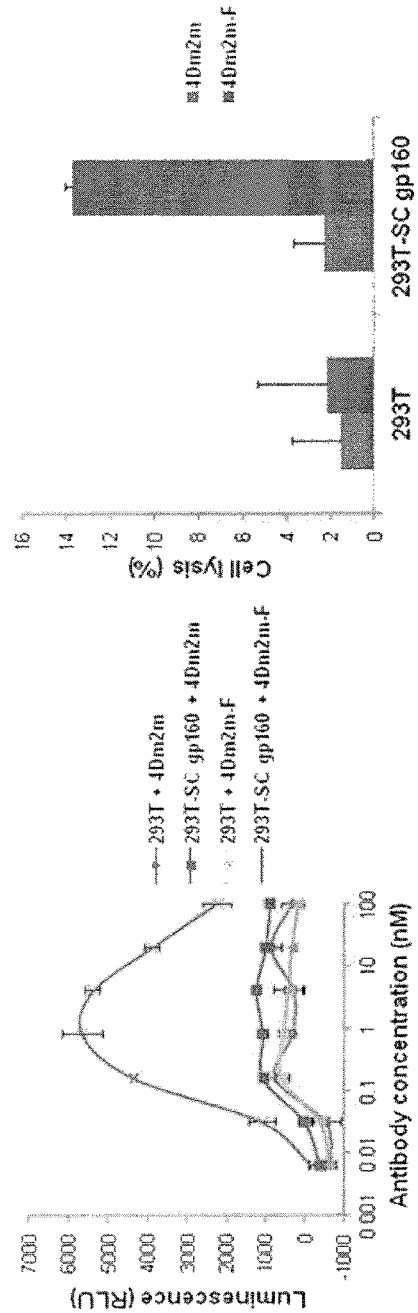

The defucosylated 4Dm2m-F construct had increased FcγRIIIa binding relative to the fully fucosylated 4Dm2m construct (see FIG. 3A). However, the binding and neutralization of HIV-1 Envs (89.6 gp140, Bal, and JRFL) was comparable between the defucosylated 4Dm2m-F construct and the fully fucosylated 4Dm2m construct (see FIGS. 3B-D).

Example 2

This example demonstrates that the defucosylated construct of the invention is more effective than the corresponding fully fucosylated construct in mediating antibody-dependent cell-mediated cytotoxicity (ADCC) in vitro and inhibiting HIV-1 infection in vivo.

In particular, in vitro ADCC assays demonstrated that the defucosylated 4Dm2m-F construct elicited stronger ADCC in HIV envelope positive cells (293T-SC gp160) relative to the fully fucosylated 4Dm2m construct (see FIGS. 4A-D).

Figure 5:
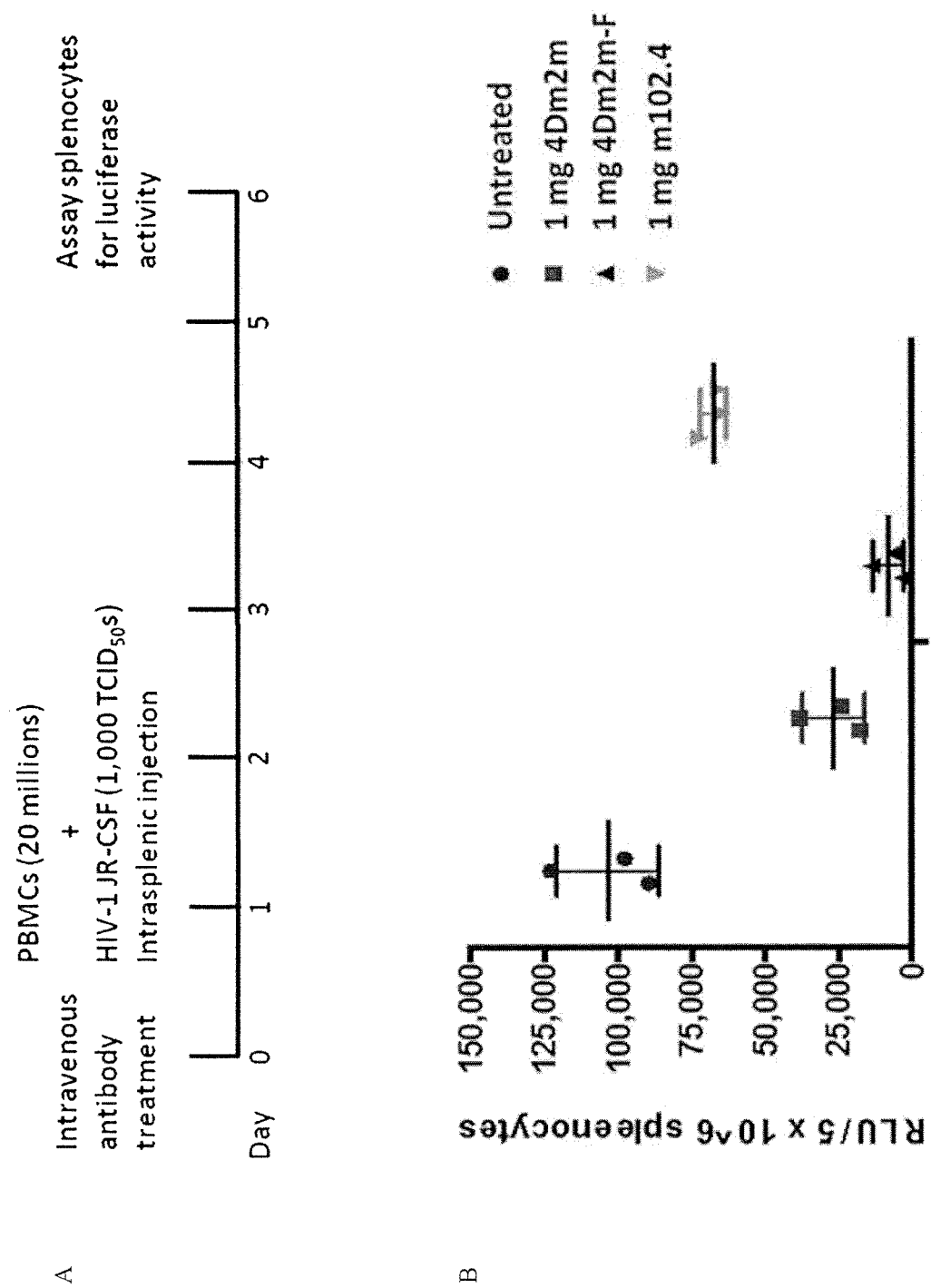
FIGS. 5A-B are images demonstrating that the defucosylated 4Dm2m-F construct was more effective than the fucosylated 4Dm2m in suppressing HIV-1 infection in humanized NSG mice.

To determine the efficacy of the inventive constructs in suppressing HIV-1 infection, humanized NOD scid gamma (NSG) mice were intravenously administered the defucosylated 4Dm2m-F construct or the fucosylated 4Dm2m construct and challenged with HIV-1 JR-CSF by intrasplenic injection (see FIG. 5A). As is clear from FIG. 5B, administration of the defucosylated 4Dm2m-F was more effective than the fucosylated 4Dm2m construct in suppressing HIV-1 infection in humanized NSG mice.

Figure 6:
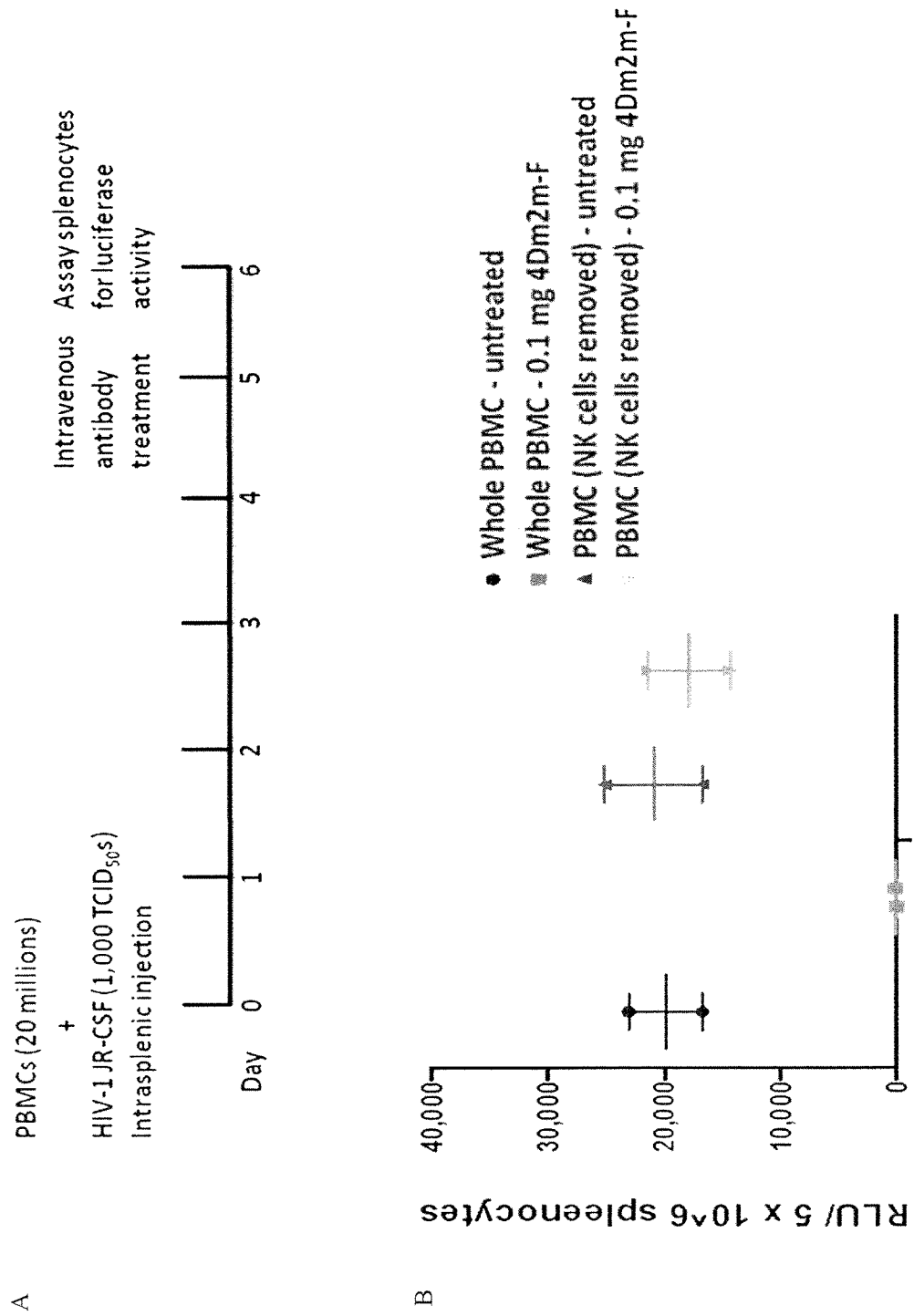
FIGS. 6A-B are images demonstrating that the defucosylated 4Dm2m-F construct eliminated HIV-1-infected cells in humanized NSG mice through NK cell-Mediated ADCC.

Furthermore, as demonstrated in FIGS. 6A-B, a single small dose of the defucosylated 4Dm2m-F construct almost completely eliminated HIV-1-infected cells through NK cell-mediated ADCC in humanized NSG mice.

Example 3

This example provides the materials and methods for Examples 4-9.

Cells, Viruses, Plasmids, Proteins and Other Reagents 293T cells were purchased from ATCC and 293 free style (293FS) cells were purchased from Invitrogen. A plasmid encoding human tyrosylprotein sulfotransferase 2 (TPST2) was purchased from OriGene. Other cell lines and plasmids used for production of pseudotyped HIV-1 and neutralization assays were obtained from the National Institutes of Health AIDS Research and Reference Reagent Program. Gp140$_{89.6}$ was a gift from Barton F. Haynes (Duke University Medical Center, Durham, N.C.), while Gp140$_{SC}$ (see Chen et al., *J. Virol.*, 85: 9395-405 (2011)), CD4-Ig (see Chen et al., *J. Virol.*, 88: 1125-39 (2014); and Chen et al., *J. Virol.*, 85: 9395-405 (2011)), and soluble human FcRn (see Feng et al., *Protein Expr. Purif.*, 79: 66-71 (2011)) were produced in the laboratory. Recombinant human Fc gamma receptor IIIa (FcγRIIIa) was purchased from R&D Systems. Horseradish peroxidase (HRP)-conjugated goat anti-human IgG (Fc-specific) antibody, HRP-conjugated goat anti-human IgG (Fab-specific) antibody, and Tris (2-carboxyethyl) phosphine (TCEP) were purchased from Sigma-Aldrich.

Computational Analysis for Identification of Amino Acid Residues at the CH1-CK Interface for Mutagenesis The atomic coordinates of CH1-CK were extracted from the crystal structure of the HIV-1 bnAb b12 (Protein Data Bank entry 1HZH). All hydrophobic residues at the CH1-CK interface were represented by using the PyMOL molecular graphics system (version 1.5.0.4; Schrödinger, LLC). Void structures at the CH1-CK interface were located by concomitantly visualizing the dummy atoms and the amino acid residues at the interface. Single point mutations were modeled using the PyMOL mutagenesis wizard with an appropriate side-chain rotamer.

Cloning of MD, an mD1.22-CH1/m36.4-CK Heterodimer

The following primers were used:

MLF,
(sense; SEQ ID NO: 52)
5'-ACCGTGGCCCAGGCGGCCCAGGTGCAGCTGGTGCAG-3';

MLR,
(antisense; SEQ ID NO: 53)
5'-CTAATTAATTATCTAGAATTACTCGAGTTTAGCTGCCGGTGCGGGTG
TAGCTGCAGGACACTCTCCCCTGTTGAA-3';

DHF,
(sense; SEQ ID NO: 54)
5'-CAACCAGCCATGGCCAAGAAGGTGGTGTACGGC-3';

DHR,
(antisense; SEQ ID NO: 55)
5'-TGGAGGCCGGCCTGGCCTTACTCGAGTTTAGCTGCCGGTGCGGGTGTA
GCTGCAGGACAAGATTTGGGCTCAACTTTCTTGTCCACCTT-3';

```
HeavyF,
                                       (sense; SEQ ID NO: 56)
5'-GCCTACGGCAGCCGCTGGATTGTTATTACTTGCTGCCCAACCAGCCAT
GGC-3';

LightR,
                                   (antisense; SEQ ID NO: 57)
5'-CCAGCGGCTGCCGTAGGCAATAGGTATTTCATTTTAAATTCCTCCTAA
TTAATTATCTAG-3'.
```

The mD1.22-CH1 and m36.4-CK gene fragments were PCR amplified with 4Dm2m-encoding plasmid as a template and primer pairs DHF/DHR and MLF/MLR, respectively. An extension of the gene fragments then was performed with primer pairs HeavyF/DHR and MLF/LightR, respectively, to add the pelB signal sequence. To obtain the full-length MD gene fragment, m36.4-CK was joined to mD1.22-CH1 by overlapping PCR with both templates in the same molarities for 7 cycles in the absence of primers and 15 additional cycles in the presence of primers MHF and DHR. The PCR product appended with SfiI restriction site on both sides was digested and cloned into pComb3X.

Construction, Panning and Screening of a Phage-Display Library of MD Mutants

The phage-display library of MD mutants was constructed by site-directed random mutagenesis. The following primers were used:

```
Bomp,
                                       (sense; SEQ ID NO: 58)
5'-GTGTGGAATTGTGAGCGG-3';

STR,
                                   (antisense; SEQ ID NO: 59)
5'-GAGGCTGTAGGTGCTGTC-3';

STF,
                                       (sense; SEQ ID NO: 60)
5'-GACAGCACCTACAGCCTCNNSAGCNNSCTGACGCTGAGCAAAGC-
3';

SSR,
                                   (antisense; SEQ ID NO: 61)
5'-GTAGAGTCCTGAGGACTG-3';

SSF,
                                       (sense; SEQ ID NO: 62)
5'-CAGTCCTCAGGACTCTACNNSCTCNNSAGCGTGGTGACCGTGCCC-
3';

mDOR,
                                   (antisense; SEQ ID NO: 63)
5'-TGGTGGCCGGCCTGGCCACAAGATTTGGGCTCAAC-3'.
```

To randomize the S69 and T71 residues of CK, a gene fragment containing the C-terminal sequence of CK, pelB signal sequence, mD1.22, and the N-terminal sequence of CH1 was amplified by PCR with MD-encoding plasmid as a template and primers STF and SSR. To mutate the S64 and S66 residues of CH1, the C-terminal sequence of CH1 was PCR amplified with primers SSF and mDoR. The two PCR products were joined together by overlapping PCR with both templates in the same molarities for 7 cycles in the absence of primers and 15 additional cycles in the presence of primers STF and mDoR. For assembly of the full-length fragments of MD mutants, a gene fragment containing m36.4 and the N-terminal sequence of CK was PCR amplified with primers Bomp and STR, and then linked to the fragment having all the mutations in CH1 and CK by overlapping PCR with primers Bomp and mDoR. The final product was digested with SfiI and cloned into the phagemid pComb3X. A phage library was prepared by electroporation of E. coli strain TG1 electroporation-competent cells (Lucigen) with desalted and concentrated ligation, as described previously (see Chen et al., J. Mol. Biol., 382: 779-89 (2008)).

To select MD mutants with preserved binding to HIV-1 Env and increased CH1-CK heterodimerization, the library was cycled through three rounds of panning against gp140$_{SC}$ followed by two additional rounds of panning against TCEP. Panning with gp140$_{SC}$ was performed according to protocols described in Zhu et al. (J. Virol. 80: 891-9 (2006)) except that 1, 0.1 and 0.1 μg of the antigen was used in the first, second, and third rounds of panning, respectively.

For panning with TCEP, the phage library generated from the third round of panning with gp140$_{SC}$ was incubated with 1 mM TCEP at room temperature for 1 h. TCEP and the m36.4-CK chain dissociated from the mD1.22-CH1 chain, which was fused to the filamentous phage coat protein III, were removed by passing the phage library through the Millipore 4-ml centrifugal filter with a cut-off of 100 kDa. The library was dialyzed against 4-ml PBS (pH 7.4) three times and then passed through the GE Healthcare HiTrap KappaSelect resin. The resin was washed with 10-ml PBS (pH 7.4) twice. Bound phage was eluted by 0.1 mM acetic acid buffer (pH 3.0) and neutralized by 1 M Tris-HCl buffer (pH 9.0) at a volume 1/10 that of elution buffer. Recovered phage was used to prepare a new library for the second round of panning, which was performed in the same way except the use of 10 mM TCEP for selection.

To identify individual mutants that preserved binding to the Env and survived the incubation with TCEP, clones were randomly picked from the last round of panning, inoculated into 96-well plates, and induced for protein expression with 1 mM isopropyl 3-D-1-thiogalactopyranoside. After overnight incubation, the supernatants of individual clones were screened for binding to gp140$_{SC}$ by using soluble expression-based monoclonal ELISA (semELISA) as described previously by Chen et al. (Mol. Immunol. 47: 912-21 (2010))

Cloning of 4Dm2m Variants (LSEV Constructs) with Stabilizing Mutations in CH1 and CK, Shortened Linkers and Enhanced Binding to FcRn The following primers were used:

```
bnIgG20L1,
                                       (sense; SEQ ID NO: 64)
5'-GTGTAAGCTTACCATGGGTGTGCCCACTCAGGTCCTGGGGTTGCTG-
3';

LSR,
                                   (antisense; SEQ ID NO: 65)
5'-GAGGCTGTAGGTGCTGTC-3';

LSF,
                                       (sense; SEQ ID NO: 66)
5'-AGCACCTACAGCCTCCTGAGCTCGCTGACGCTGAGCAAAGC-3';

CKR3,
                                   (antisense; SEQ ID NO: 67)
5'-CAATGAATTCATTAACACTCTCCCCTG-3';

SacF,
                                       (sense; SEQ ID NO: 68)
5'-GATCGAGCTCAGCTTCCACC-3';

EVR,
                                   (antisense; SEQ ID NO: 69)
5'-CACGGTCACCACGCTCACGAGCTCGTAGAGTCCTGAGGACTG-3';

EVF,
                                       (sense; SEQ ID NO: 70)
5'-AGCGTGGTGACCGTGCCC-3';
```

-continued

AAAR,
(antisense; SEQ ID NO: 71)
5'-CCCGAGGTCGACGCTCTC-3';

G4SR1,
(antisense; SEQ ID NO: 72)
5'-TGACCCGCCTCCACCTGAGGAGACGGTGACCAG-3';

G4SF2,
(sense; SEQ ID NO: 73)
5'-GGTGGAGGCGGGTCACGAACTGTGGCTGCACCA-3';

bnIgG20H1,
(sense; SEQ ID NO: 74)
5'-GTGTTCTAGAGCCGCCACCATGGAATGGAGCTGGGTCTTTCTCTTC-3';

mD1.22R21,
(SEQ ID NO: 75)
5'-GCTGAGCTCCCGCCTCCACCGCCTACCACTACCAGCTG-3';

CH3R5,
(antisense; SEQ ID NO: 76)
5'-TGACCCGCCTCCACCTTTACCCGGAGACAGGGA-3';

mD1.22F16,
(sense; SEQ ID NO: 77)
5'-GGTGGAGGCGGGTCAAAGAAGGTGGTGTACGGC-3';

DKR1,
(antisense; SEQ ID NO: 78)
5'-TGTGTGAGTTTTGTCTGAGGAGACGGTGACCAG-3';

DKF1
(sense; SEQ ID NO: 79)
5'-GACAAAACTCACACACGAACTGTGGCTGCACCA-3';

mD1.22R22,
(antisense; SEQ ID NO: 80)
5'-GCTGAGCTCGTGTGAGTTTTGTCGCCTACCACTACCAGCTG-3';

CH3R6,
(antisense; SEQ ID NO: 81)
5'-GGTATGCGTCTTATCTTTACCCGGAGACAGGGA-3';

mD1.22F17,
(sense; SEQ ID NO: 82)
5'-GATAAGACGCATACCAAGAAGGTGGTGTACGGC-3';

FcF6,
(sense; SEQ ID NO: 83)
5'-GACAAAACTCACACATGC-3';

LSR1,
(antisense; SEQ ID NO: 84)
5'-CTTCTGCGTGTAGTGGCTGTGCAGAGCCTCATGCAGCACGGAGCATGAGAAG-3';

LSF1,
(sense; SEQ ID NO: 85)
5'-CTTCTCATGCTCCGTGCTGCATGAGGCTCTGCACAGCCACTACACGCAGAAG-3';

FcR8,
(antisense; SEQ ID NO: 86)
5'-TTTACCCGGAGACAGGGAG-3';

CH1R4,
(antisense; SEQ ID NO: 87)
5'-TGTGTGAGTTTTGTCACAAGATTTGGGCTCAACTTTCTTGTCCACCTTG-3';

DAF,
(sense; SEQ ID NO: 88)
5'-CTCCCTGTCTCCGGGTAAA-3'.

For cloning of the 4Dm2m variant (designated LSEV) with stabilizing mutations in CH1 and CK, the S69L and T71S mutations first were introduced into CK with pDR12 vector-based 4Dm2m-encoding plasmid (see Chen et al., *J. Virol.*, 88: 1125-39 (2014)) as a template. A gene fragment encoding the light chain leader peptide (Lleader), m36.4 and the N-terminal sequence of CK was PCR amplified with 4Dm2m-encoding plasmid as a template and primers bnIgG20L1 and LSR. The C-terminal portion of CK was amplified with primers LSF and CKR3. The two gene fragments were fused to each other by overlapping PCR with primers bnIgG20L1 and CKR3. The product was digested with HindIII and EcoRI, and cloned into the 4Dm2m-encoding plasmid lineared by the same restriction enzymes.

To introduce the S64E and S66V mutations into CH1, the N-terminal sequence of CH1 was PCR amplified with 4Dm2m-encoding plasmid as a template and primers SacF and EVR. A long fragment containing the C-terminal portion of CH1, Fc, mD1.22 and polyA signal sequence was amplified with 4Dm2m-encoding plasmid as a template and primers EVF and AAAR. The two fragments were linked to each other by overlapping PCR with primers SacF and AAAR. The product was digested with SacI and SalI, and cloned into the construct containing the S69L and T71S mutations in CK.

To clone the 4Dm2m variant (designated LSEVs) with both the CH1-CK stabilizing mutations and a single copy of the G4S sequence as linkers, a 4Dm2m variant (designated 4Dm2 ms) first was generated containing only the G4S linker as an intermediate construct. To shorten the linker between m36.4 and CK in the light chain, the Lleader-m36.4 and CK gene fragments were PCR amplified with 4Dm2m-encoding plasmid as a template and primer pairs bnIgG20L1/G4SR1 and G4SF2/CKR3, respectively. They were linked together by overlapping PCR with primers bnIgG20L1 and CKR3. The product was digested with HindIII and EcoRI, and cloned into the 4Dm2m-encoding plasmid lineared by the same restriction enzymes. To shorten the linker between mD1.22 and CH1 in the heavy chain, a gene fragment containing the heavy chain leader peptide (Hleader) and mD1.22 was PCR amplified with 4Dm2m-encoding plasmid as a template and primers bnIgG20H1 and mD1.22R21. The product was digested with XbaI and SacI, and cloned into the construct with shortened G4S linker in the light chain. To shorten the linker between Fc and mD1.22 at its C terminus, the two gene fragments encoding the heavy chain constant region and mD1.22-polyA signal sequence were amplified with 4Dm2m-encoding plasmid as a template and primer pairs SacF/CH3R5 and mD1.22F16/AAAR, respectively. They were fused to each other by overlapping PCR with primers SacF and AAAR. The product was digested with SacI and SalII, and cloned into the previous construct containing shortened G4S linkers in the light chain and between mD1.22 and CH1 in the heavy chain. The 4Dm2 ms-encoding plasmid was then used as a template to generate LSEVs by using the same protocols for cloning LSEV.

The 4Dm2m variant (designated LSEVh) with both the CH1-CK stabilizing mutations and the human IgG1 hinge sequence DKTHT (SEQ ID NO: 35) as linkers was constructed in the same way as LSEVs was generated. The primer pairs bnIgG20L1/DKR1 and DKF1/CKR3 were used to PCR amplify the Lleader-m36.4 and CK gene fragments, respectively, to replace the (G4S)3 linker between m36.4 and CK with DKTHT (SEQ ID NO: 35). The primers bnIgG20H1 and mD1.22R22 were used to amplify the Hleader-mD1.22 gene fragment to replace the (G4S)3 linker between mD1.22 and CH1 with DKTHT (SEQ ID NO: 35). The primer pairs SacF/CH3R6 and mD1.22F17/AAAR were used to amplify the gene fragments encoding the heavy chain constant region and mD1.22-polyA signal, respectively, to replace the (G4S)3 linker between Fc and mD1.22 at its C terminus with DKTHT (SEQ ID NO: 35).

To generate the LSEVh variant (LSEVh-LS) with M428L and N434S mutations in Fc, the N- and C-terminal sequences of Fc were PCR amplified with an Fc-encoding plasmid as a template and primer pairs FcF6/LSR1 and LSF1/FcR8, respectively. Full-length Fc gene fragment bearing the two mutations was obtained by overlapping PCR with primers FcF6 and FcR8. The CH1 and mD1.22-polyA signal sequences were PCR amplified with primer pairs SacF/CH1R4 and DAF/AAAR, respectively, and fused to the N and C terminus, respectively, of Fc by overlapping PCR with primers SacF and AAAR. The product was digested with SacI and SalI, and cloned into the LSEVh-encoding plasmid lineared by the same restriction enzymes.

Cloning of eCD4-Ig$^{Q40A,mim2}$

The following primers were used:

```
D1D2F1,
                       (sense; SEQ ID NO: 89)
5'-ACGCGGCCCAGCCGGCCAAGAAGGTGGTGCTGGGC-3';

D1D2R1,
                       (antisense; SEQ ID NO: 90)
5'-GGTCAGGAAGCTGCCCGCGTTGCCCAGGATCTTG-3';

D1D2F2,
                       (sense; SEQ ID NO: 91)
5'-GGCAGCTTCCTGACCAAG-3';

D1D2R2,
                       (antisense; SEQ ID NO: 92)
5'-TGTGTGAGTTTTGTCACAAGATTTGGGCTCCGGGTCTGCCGCGGCCA
GCACCACGATGTC-3';

FcF5,
                       (sense; SEQ ID NO: 93)
5'-GACAAAACTCACACATGC-3';

Min2R,
                       (antisense; SEQ ID NO: 94)
5'-GCGGGTTTAAACTCAATCCATATCGTAGTAGTAGCCCCCATCGTAGT
CGTAGTAGTCTCCACCGCCTCCACCTTTACCCGGAGACAGGGAGAG-3'.
``` eCD4-Ig$^{Q40A,mim2}$ was cloned according to the sequence reported by Gardner et al. (Nature, 519: 87-91 (2015)). To introduce the Q40A mutation into the human CD4 D1D2 domains, the gene fragments encoding the N- and C-terminal sequence of D1D2 were PCR amplified with D1D2-encoding plasmid as a template and primer pairs D1D2F1/D1D2R1 and D1D2F2/D1D2R2, respectively. They were linked to each other by overlapping PCR with primers D1D2F1 and D1D2R2. The gene fragment containing the human IgG1 Fc and the CCR5 mimetic mim2 at its C terminus was PCR amplified with Fc-encoding plasmid as a template and primers FcF5 and Min2R, and then fused to the D1D2 gene fragment by overlapping PCR with primers D1D2F1 and Min2R. The final product was digested with SfiI and PmeI, and cloned into pSecTagB.

Protein Expression and Purification

MD variants were expressed in *E. coli* HB2151 cells and all 4Dm2m variants (LSEV constructs) were expressed in 293FS cells as described in Chen et al. (*Proc. Natl. Acad. Sci. USA*, 105: 17121-6 (2008)). To boost tyrosine sulfation, 293FS cells were cotransfected with antibody-encoding and TPST2-encoding plasmid at a 1:1 ratio. MD variants were purified from the soluble fraction of *E. coli* periplasm by using the GE Healthcare HiTrap KappaSelect resin according to the manufacturer's instructions. 4Dm2m variants (LSEV constructs) were purified from the 293FS cell culture supernatants by Protein A Sepharose 4 Fast Flow column chromatography (GE Healthcare) according to the manufacturer's protocols.

Size-Exclusion Chromatography

A Superdex200 10/300 GL column (GE Healthcare) was calibrated with protein molecular mass standards of carbonic anhydrase (29 kDa), ovalbumin (44 kDa), conalbumin (75 kDa), aldolase (158 kDa) and ferritin (440 kDa). Purified proteins at a concentration of 1 mg ml$^{-1}$ in PBS (pH7.4) were loaded onto the pre-equilibrated column and eluted with PBS (pH7.4) at 0.5 ml/min.

High-Resolution Mass Spectrometry

High-resolution mass spectrometry was performed according to Zhu et al. (MAbs 6: 1190-200 (2014)).

Enzyme-Linked Immunosorbent Assay (ELISA)

ELISA was performed as described in Chen et al. (Proc. Natl. Acad. Sci. USA, 105: 17121-6 (2008)). Briefly, antigens were coated on 96-well plates at a concentration of 2 µg ml$^{-1}$. Bound MD variants were detected by HRP-conjugated goat anti-human IgG (Fab-specific) antibody. Bound 4Dm2m variants (LSEV constructs) were detected by HRP-conjugated goat anti-human IgG (Fc-specific) antibody. Half-maximal binding ($EC_{50}$) was calculated by fitting data to the Langmuir adsorption isotherm.

Surface Plasmon Resonance (SPR)

Binding kinetics of MD variants with gp140$_{89.6}$ were assessed by SPR on Biacore X100 (GE Healthcare) using a single-cycle approach as described in Chen et al. (*J. Virol.*, 85: 9395-405 (2011)). Analytes were tested at 1,000, 100, 10, 1, and 0.1 nM concentrations. Binding kinetics of 4Dm2m variants (LSEV constructs) with FcRn and FcγRIIIa were assessed by using a multi-cycle and single-cycle approach, respectively, according to the protocols described in Chen et al. (*J. Virol.*, 85: 9395-405 (2011)) and Feng et al. (*Protein Expr. Purif.* 79: 66-71 (2011)). Analytes were tested at 2,400, 1,200, 600, 300, and 150 nM concentrations. Kinetic constants were calculated from the sensorgrams fitted with bivalent (for gp140$_{896}$ and FcRn) or monovalent (for FcγRIIIa) binding model of the BiacoreX100 evaluation software 2.0.

Pseudovirus Neutralization Assay

HIV-1 pseudoviruses were generated and neutralization assays were performed as described in Chen et al. (*Proc. Natl. Acad. Sci. USA*, 105: 17121-6 (2008)).

Dynamic Light Scattering (DLS)

Proteins concentrated to 1 (for eCD4-Ig) or 5 (for all other samples) mg ml$^{-1}$ were stored at −80° C. and slowly thawed on ice before measurement. Samples then were incubated at 4 or 37'C. On day 0, 1, 3, and 7, samples were collected and centrifuged at 18,000×g for 10 min to remove precipitates. The supernatants were diluted to 0.5 mg/mL and used for DLS measurement (Zetasizer Nano ZS 3600, Malvern Instruments Limited, MA) according to the manufacturer's instructions.

Pharmacokinetic Measurement in Mice

Human FcRn transgenic mice mFcRn$^{-/-}$hFcRn(267)$^{Tg/Tg}$ (stock number 004919) were purchased from Jackson Laboratory. Animals were intravenously injected with either 0.1 (for eCD4-Ig) or 1 mg (for all others) proteins on day 0. Plasma samples were collected by submandibular bleeding daily for 7 days after injection. Serum concentrations of proteins were determined by ELISA with standard curves generated using the original protein stocks and the HIV-1 Env gp140$_{89.6}$.

Generation of CHO Stable Cell Lines Producing Defucosylated LSEVh-LS

CHO-K1 cells with the GDP-fucose transporter (GFT) gene knockout (CHOF6) were generated (Zhu et al., unpublished). CHOF6 cells were used to establish stable cell lines producing defucosylated LSEVh-LS by using the standard glutamine synthetase-based selection system.

Example 4

This example demonstrates the improvement of CH1-CK heterdimerization through structure-guided rational design and phage-display library technology.

CH1-CK heterodimerization previously had been shown to be inefficient and unstable (see Schoonjan et al., *J. Immunol.*, 165: 7050-7057 (2000); Muller et al., *FEBS Lett.*, 422: 259-264 (1998); and Rozan et al., *Mol. Cancer Ther.*, 12: 1481-1491 (2013)). CH1-CK had been used as a heterodimerization scaffold to generate bispecific antibodies (see Muller et al., *FEBS Lett.*, 422: 259-264 (1998) or multivalent fusion proteins (see Allaway et al., *AIDS Res. Hum. Retroviruses*, 11: 533-9 (1995)). However, it also had been demonstrated that cooperation between the VH-VL and CH1-CK interface was required for mutual stabilization (see Rothlisberger et al., *J. Mol. Biol.*, 347: 773-89 (2005)) and in the absence of VH-VL, CH1-CK failed to yield heterodimeric products (see Schoonjan et al., *J. Immunol.*, 165: 7050-7057 (2000)).

To evaluate CH1-CK heterodimerization strength in the context of 4Dm2m, the N-terminal region of 4Dm2m was subcloned, resulting in a heterodimeric construct (designated MD) composed of mD1.22-CH1 and m36.4-CK with total calculated molecular weight (cMW) of 52 kDa (see FIG. 7A). MD was expressed and affinity purified from the soluble fraction of *E. coli* periplasm by using a CK-specific ligand. On a non-reducing SDS-PAGE, approximately 60% of the purified protein migrated as dissociated mD1.22-CH1 and/or m36.4-CK monomer with an apparent molecular weight (aMW) of 30 kDa, which is larger than their cMWs (25.2 and 26.5 kDa, respectively) (see FIG. 7B). Size-exclusion chromatography revealed that similarly about 40% of the protein eluted at an aMW comparable to the cMW (52 kDa) of an mD1.22-CH1/m36.4-CK heterodimer, which could be further reduced by 1 mM TCEP (see FIG. 7C). However, high-resolution mass spectrometry revealed that the purified protein contained m36.4-CK only with undetectable mD1.22-CH1 (see FIG. 7D). These results confirmed the previous finding that CH1-CK heterodimerization is inefficient (see Schoonjan et al., *J. Immunol.*, 165: 7050-7057 (2000)). Furthermore, these results suggest that in bacteria, CH1-CK interaction is not sufficiently strong to ensure formation of stable heterodimers.

Figure 8A:
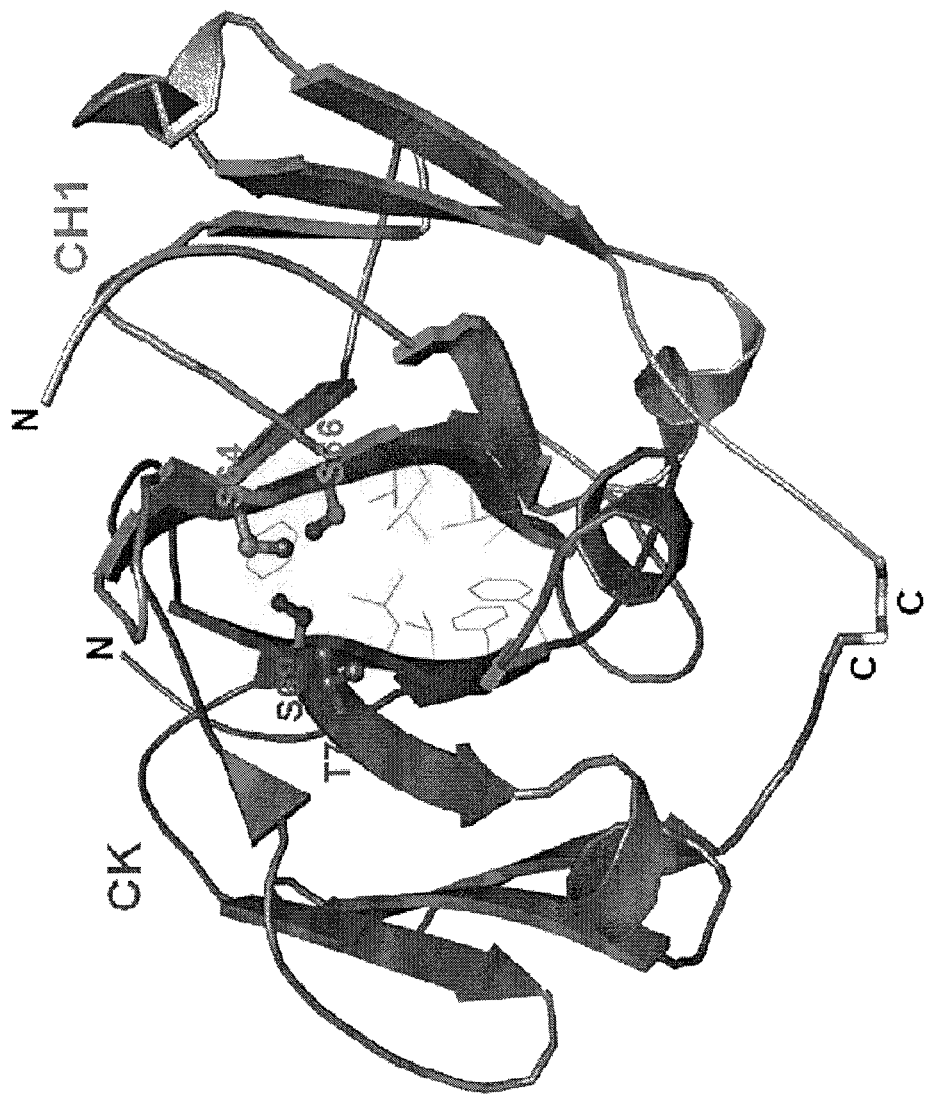
FIGS. 8A-C are images showing rational design and identification of stabilized CH1-CK. (A) Structural analysis of CH1-CK interface. The side chains of hydrophobic residues at the interface are shown in slim stick representation. The four amino acid residues lining a void structure are indicated with their side chains shown in bold ball-and-stick representation. N and C denote the N and C terminus, respectively, of CH1 and CK. (B) Phage-display library panning for enrichment of stabilized CH1-CK. The triangle on the right represents a centrifugal filter with a cut-off of 100 kDa. All other figure elements are defined in the legend (centered rectangle). (C) Selection of stabilized CH1-CK. The amino acid sequences of selected CH1 and CK variants are aligned and numbered. Mutations from the wild-type sequences are highlighted with gray shading. The amino acid sequences of the CH1 of MD, MD6, MD12, MD13, MD27, MD34, and MD35 correspond to SEQ ID NOs: 21-27, respectively. The amino acid sequence of the CK of MD, MD6, MD12, MD13, MD27, MD34, and MD35 correspond to SEQ ID NOs: 28-34, respectively.

In an effort to improve CH1-CK heterodimerization, the CH1-CK crystal structure was analyzed. The analysis revealed that hydrophobic interaction at the N-terminal half of the CH1-CK interface is weak while the C-terminal half contains many hydrophobic residues (see FIG. 8A). To test whether substitution of some amino acid residues at the N-terminal half of the interface with hydrophobic residues might enhance the interaction leading to more stable CH1-CK heterodimerization, a void structure at the CH1-CK interface was identified that could accommodate bulky amino acid side chains without causing steric clashes. The void is lined by the S64/S66 residues of CH1 and the S69/T71 residues of CK.

Figure 8B:
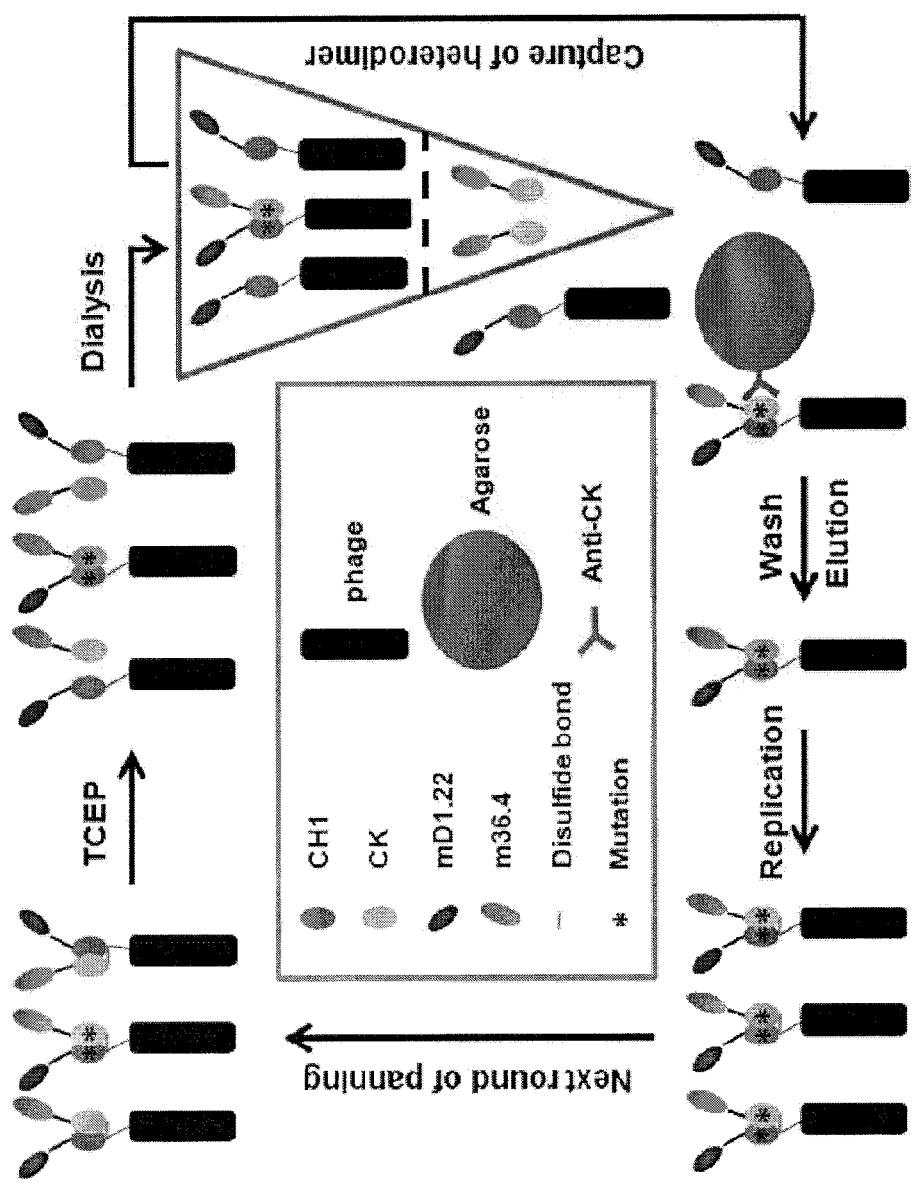

Accordingly, a phage-display library of MD mutants was generated by randomizing the four residues with the degenerate codon NNS, which encodes the complete set of standard amino acids. The library was first cycled through three rounds of panning against gp140$_{SC}$ to enrich clones with preserved binding to the HIV-1 Env. To enrich clones with stable CH1-CK heterodimerization even if the inter-chain disulfide bridge does not form or is interrupted, two additional rounds of selection with a CK-specific ligand were then performed after the resulting phage library was treated with the reducing reagent TCEP (1 and 10 mM for the first and second round, respectively) (see FIG. 8B).

Figure 8C:
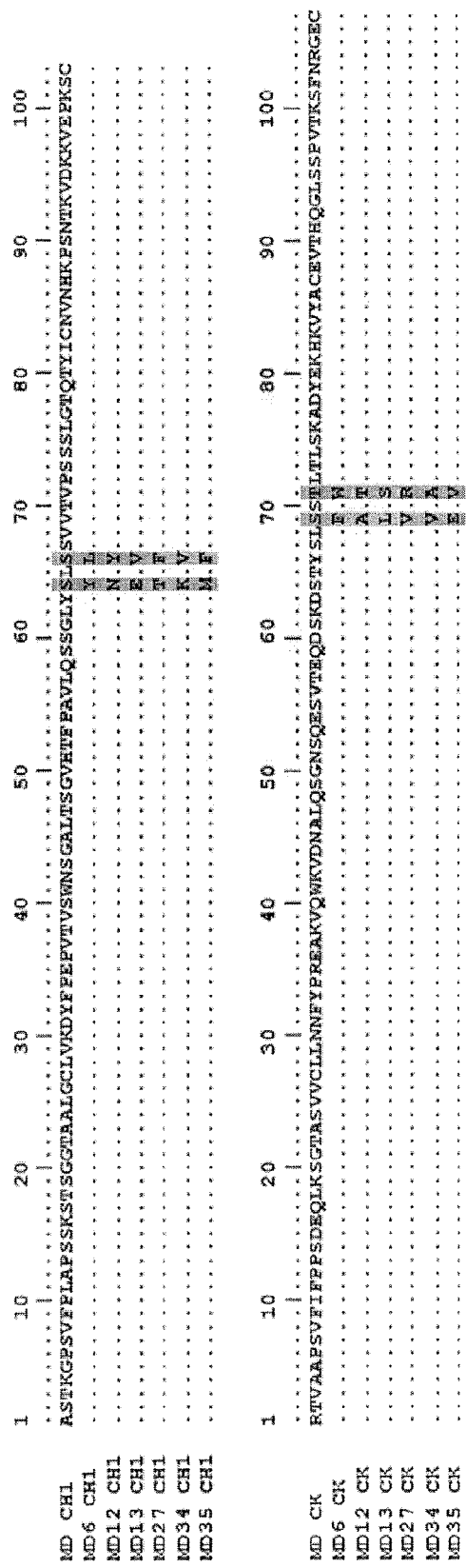
Figure 9A:
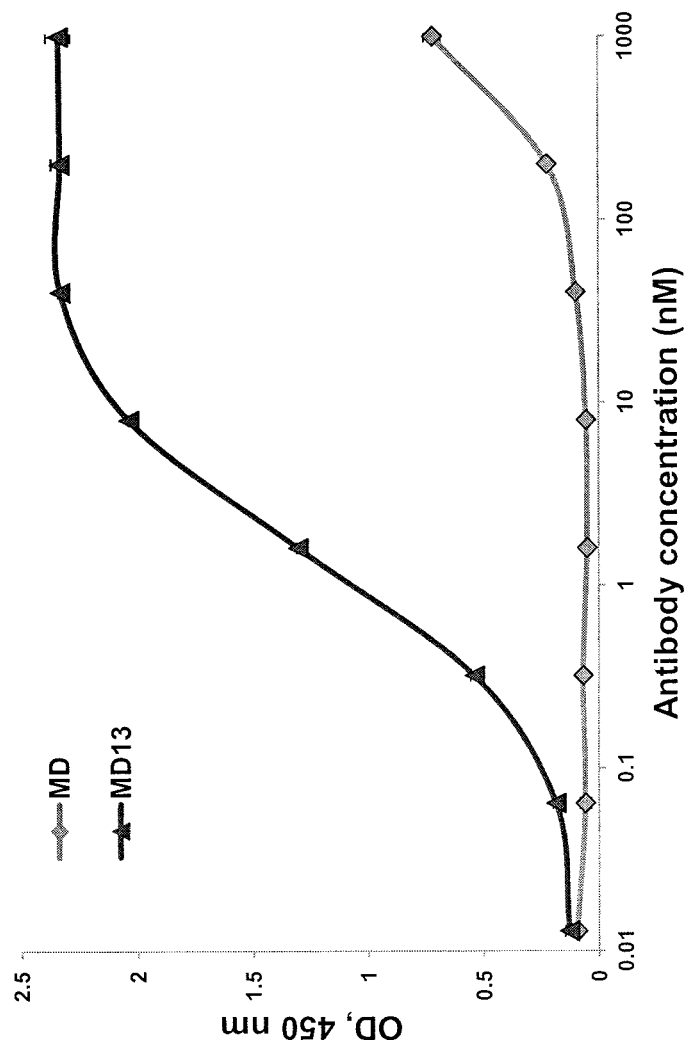
FIGS. 9A-D are images showing the characterization of MD13. (A) ELISA binding to the HIV-1 Env gp140$_{89.6}$. Gp140$_{89.6}$ was coated on 96-well plates at a concentration of 2 μg ml$^{-1}$. Bound MD and MD13 were detected by HRP-conjugated goat anti-human IgG (Fab-specific) antibody. (B) Binding kinetics of MD and MD13 with gp140$_{89.6}$ as measured by SPR. SPR analysis was performed on Biacore X100 by using a single-cycle approach according to the manufacturer's instructions. Analytes were tested at 1,000, 100, 10, 1, and 0.1 nM concentrations. Kinetic constants shown on the right were calculated from the sensorgrams fitted with bivalent binding model of the BiacoreX100 evaluation software 2.0. $K_a$, association rate constant; $K_d$, dissociation rate constant; $K_D$, equilibrium dissociation constant. (C) High-resolution mass spectrometry. Mass spectra were shown with deconvoluted mass for each peak indicated at the top. (D) Structural modeling of the CH1-CK interface in MD13. The side chains of hydrophobic residues at the interface are shown in slim stick representation. The four amino acid substitutions are indicated with their side chains shown in bold stick repress entation. The black dashed line indicates possible formation of a hydrogen bond between the residues. N and C denote the N and C terminus, respectively, of CH1 and CK.
Figure 9B:
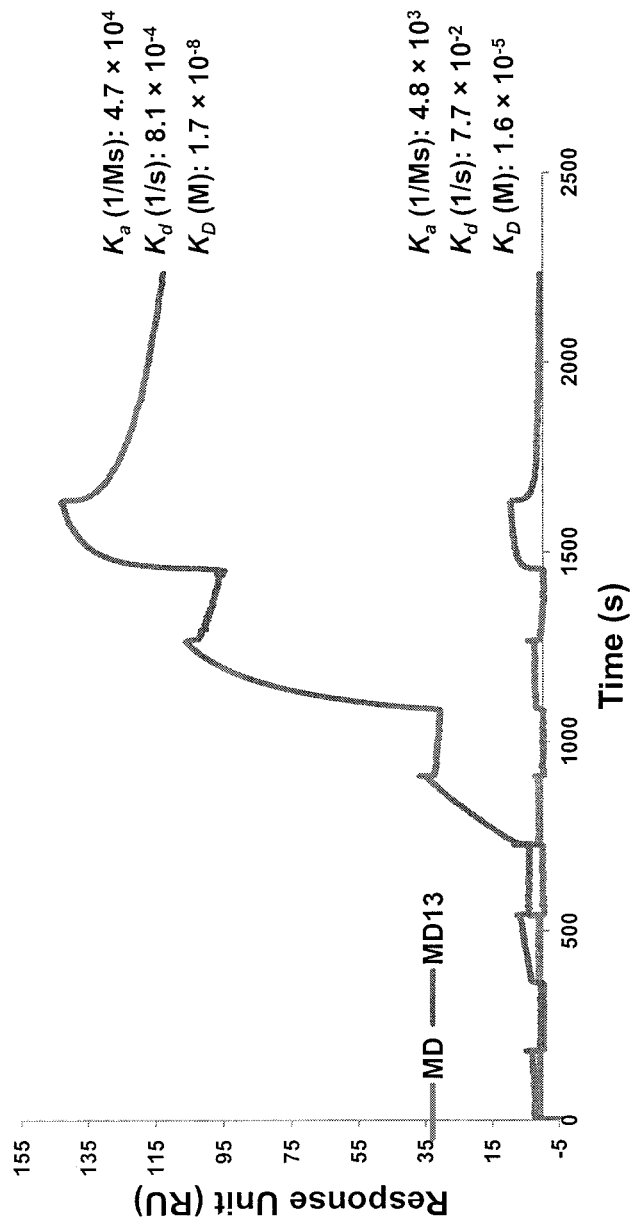
Figure 9C:
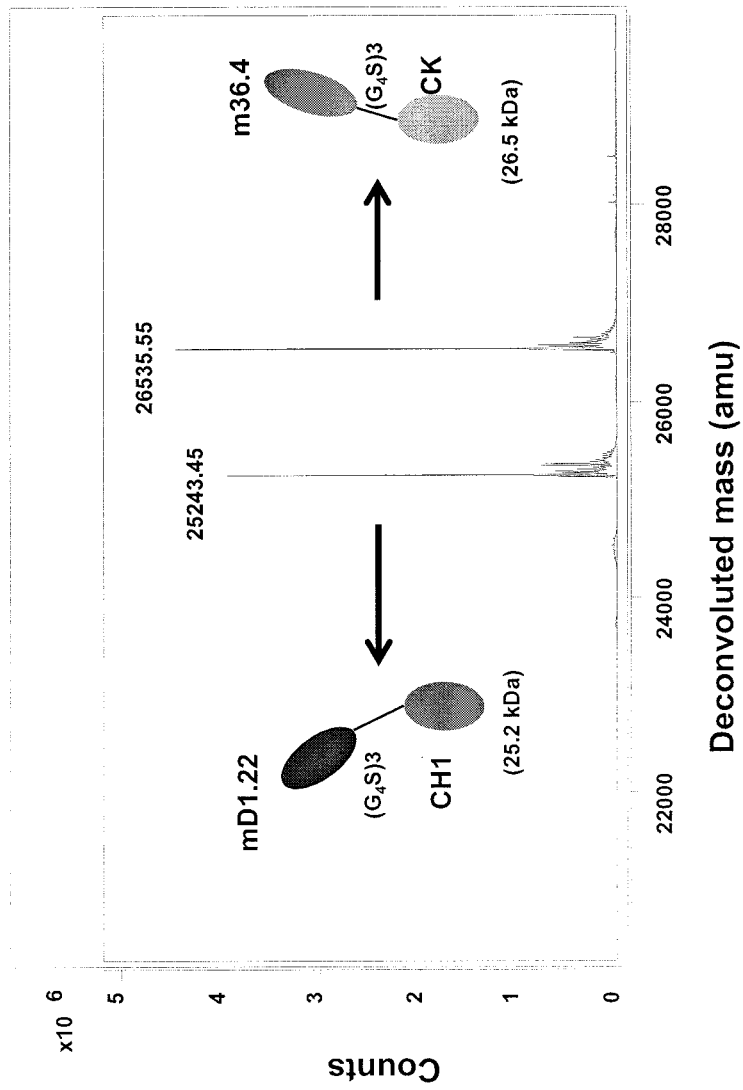
Figure 9D:
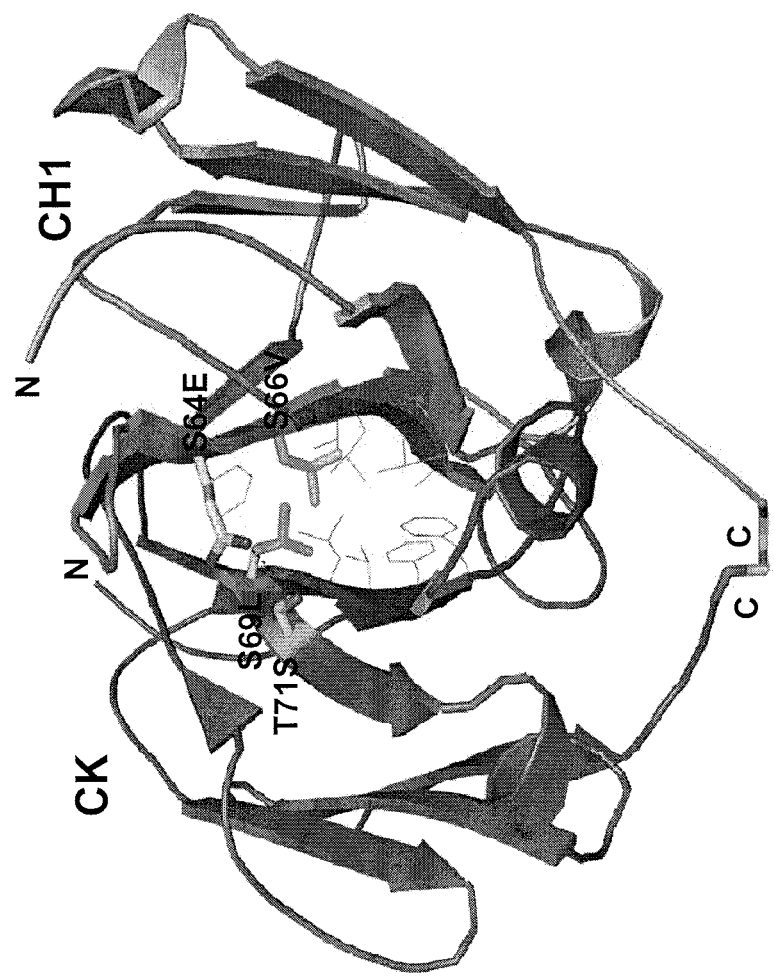

Screening the final library led to the identification of six dominant MD mutants (see FIG. 8C). They all have hydrophobic residues in the position 66 of CH1 and position 69 of CK (except MD35). In contrast, there is no preferential use of types of amino acid residues in the other two positions. MD12 and MD27 were poorly expressed as soluble proteins in *E. coli* and therefore were not further characterized. The other four MD mutants all contained a larger portion of proteins than the wild type that eluted at an aMW comparable to the cMW (52 kDa) of an mD1.22-CH1/m36.4-CK heterodimer, as demonstrated by size-exclusion chromatography. However, only MD13 was not reduced by 1 mM TCEP. In ELISA (see FIG. 9A) and SPR (see FIG. 9B), MD13 showed nanomolar affinities for the HIV-1 Env gp140$_{89.6}$, approximately 1,000-fold higher than those of MD. Other MD mutants also showed much higher binding activity than MD. Given that mD1.22 has nanomolar affinities for HIV-1 Env while m36.4 barely binds without sCD4 as demonstrated in Chen et al., J. Virol., 88: 1125-39 (2014); Chen et al., Antiviral Res., 88: 107-15 (2010); and Chen et al., Proc. Natl. Acad. Sci. USA, 105: 17121-6 (2008), the results suggest that the purified MD13 protein should contain mD1.22-CH1 at a certain level. As expected, mass spectrometry confirmed the presence of mD1.22-CH1 with abundance comparable to that of m36.4-CK (see FIG. 9C). Structural modeling indicated that the S66V mutation of CH1 and the S69L mutation of CK in MD13 could create hydrophobic packing interaction in between or with other hydrophobic residues at the interface and a hydrogen bond could form between the other two substitutions (S64E of CH1 and T71 S of CK) (see FIG. 9D).

These results demonstrate the identification of six CH1-CK mutants that resulted in formation of more stable heterodimers of the MD variants than the wild-type MD. They preferentially used hydrophobic amino acid residues in position 66 of CH1 and position 69 of CK, suggesting increased hydrophobic interactions as a major mechanism for enhanced heterodimerization. The heterodimerization in MDI 3 was not affected by 1 mM TCEP, suggesting strong interactions between CH1 and CK in the absence of the inter-chain disulfide bridge. These stabilized CH1-CK mutants are useful as new scaffolds for generation of bispecific and multispecific antibodies or proteins.

Example 5

This example demonstrates the design, generation and initial characterization of 4Dm2m variants (LSEV constructs) with stabilized CH1-CK and shortened polypeptide linkers.

Figure 10A:
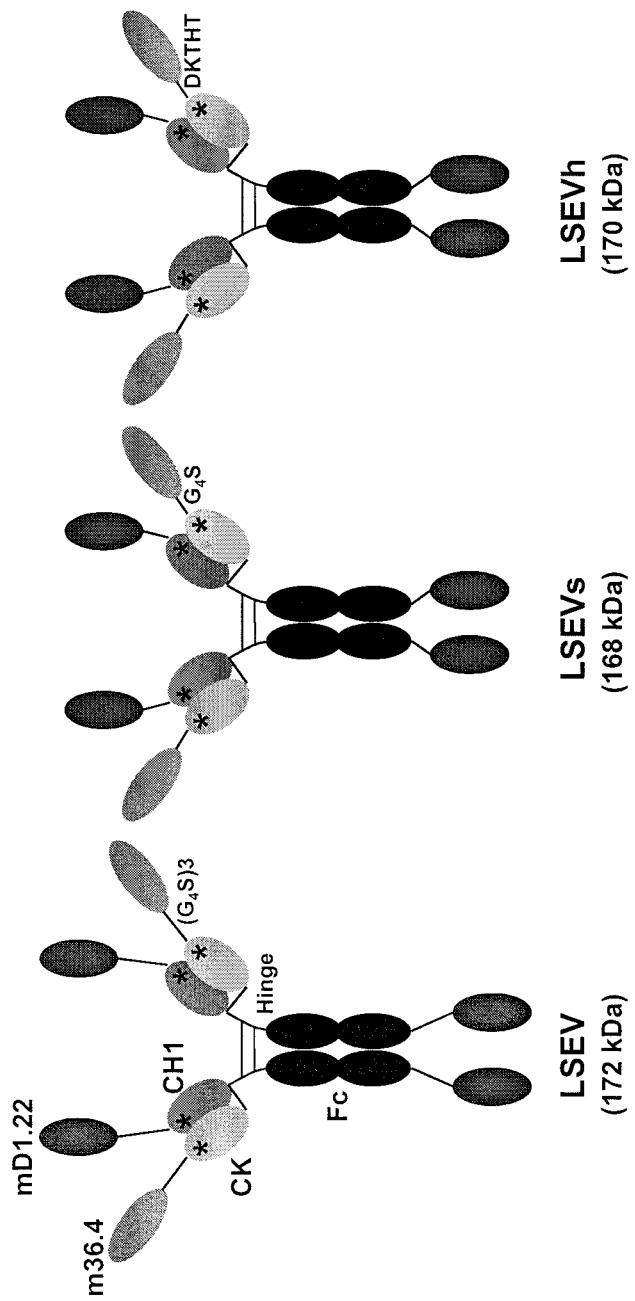
FIGS. 10A-C are images showing the design, generation, and initial characterization of 4Dm2m variants (LSEV constructs). (A) Schematic representation of 4Dm2m variants (LSEV constructs). The line connecting the C termini of CH1 and CK denotes the inter-chain disulfide bridge. The stars represent the S64E/S66V substitutions in CH1 and S69/T71S substitutions in CK. Calculated molecular masses are shown in parentheses. DKTHT (SEQ ID NO: 35) is a linker derived from human IgG1 hinge. (B) Nonreducing and reducing SDS-PAGE of 4Dm2m variants (LSEV constructs). Molecular masses of standards are shown on the left. (C) Size-exclusion chromatography of 4Dm2m variants (LSEV constructs). The arrows at the top indicate the elution volumes of the molecular mass standards in PBS (pH 7.4): carbonic anhydrase (29 kDa), conalbumin (75 kDa), aldolase (158 kDa), and ferritin (440 kDa). The arrows in the "4Dm2m+1 mM TCEP" panel indicate the elution of heavy and light chains of 4Dm2m devoid of each other.

The stabilizing mutations in the CH1-CK of MDI 3 were introduced into 4Dm2m resulting in the first variant, LSEV (see FIG. 10A). Shortening the (G4S)3 linkers used in 4Dm2m or replacing them with human sequences naturally designed for both flexibility and stability might render the fusion protein less susceptible to proteolysis. To test this hypothesis, two LSEV variants were generated: one (LSEVs) with a single copy of the G4S motif (SEQ ID NO: 36) and the other (LSEVh) with a sequence (DKTHT; SEQ ID NO: 35) derived from the human IgG1 hinge as linkers (see FIG. 10A).

Figure 10B:
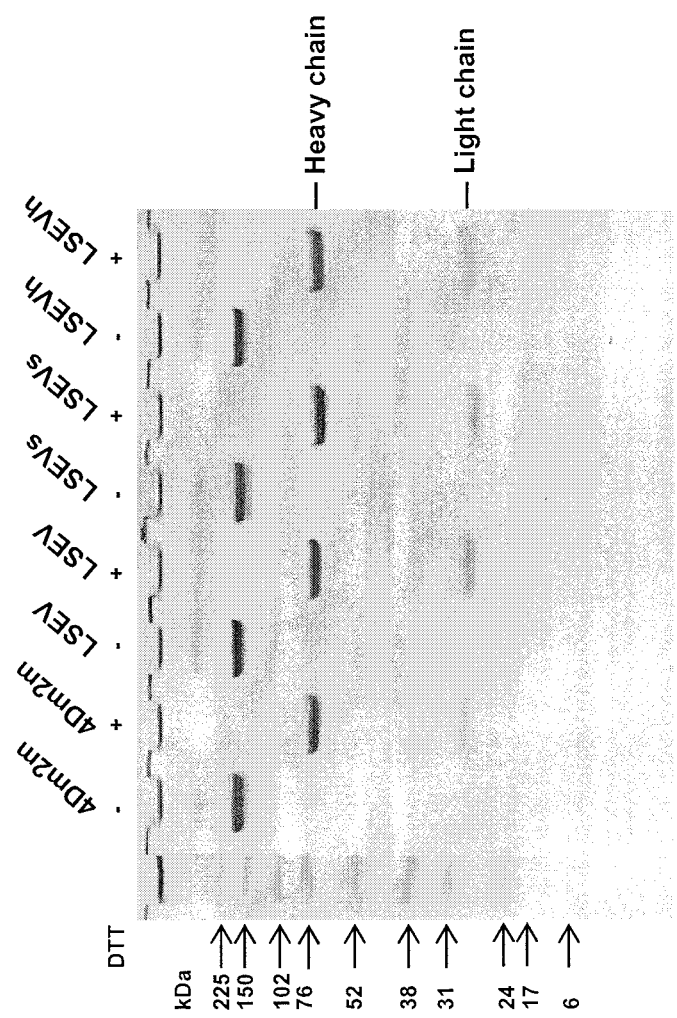
Figure 10C:
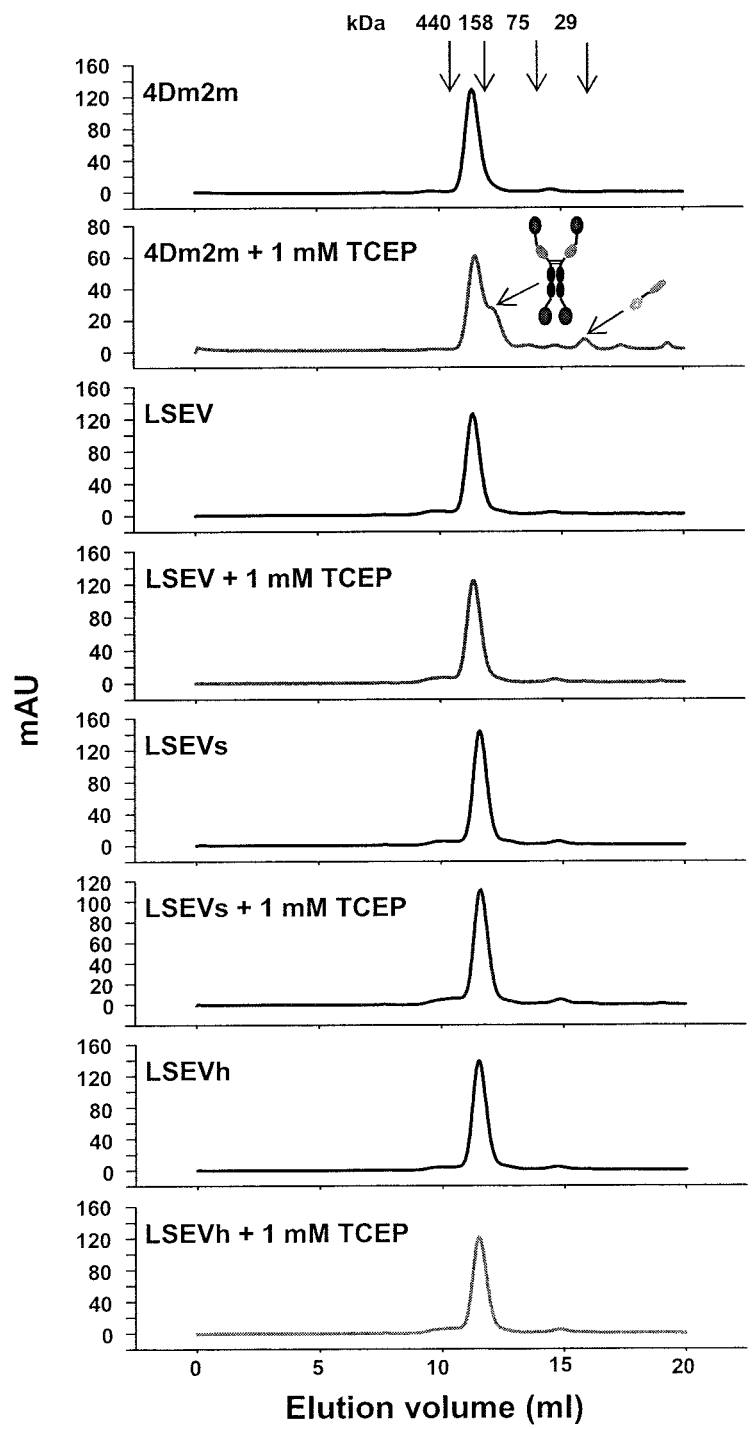

The 4Dm2m variants (LSEV constructs) were well expressed in transiently transfected 293FS cells and secreted into the culture supernatants. Interestingly, the engineering gradually increased the expression levels of the variants with LSEVh having the highest yield (10-15 mg liter$^{-1}$), which is approximately two-three-fold higher than that (5-6 mg liter$^{-1}$) of 4Dm2m and comparable to that (10-20 mg liter-) of typical human IgG is. Unlike the bacterially expressed MD protein (see FIG. 7B), 4Dm2m migrated almost as a single band with aMW (approximately 180 kDa) comparable to its cMW (172 kDa) on an SDS-PAGE under non-reducing condition (see FIG. 10B), suggesting that CH1-CK heterodimerization is much more efficient in the mammalian expression system likely due to more efficient protein folding machinery and/or more favorable cellular environment. As expected, incubation with 1 mM TCEP led to partial dissociation between the heavy and light chains of 4Dm2m while all the variants with stabilizing mutations in CH1-CK maintained integrity, as demonstrated by size-exclusion chromatography (see FIG. 10C).

Example 6

This example demonstrates the preserved biological activities and drug-related properties of 4Dm2m variants (LSEV constructs).

To find out whether the engineering would affect biological activities and drug-related properties, the 4Dm2m variants (LSEV constructs) were tested for their ability to neutralize HIV-1 and aggregation propensities during prolonged incubation. CD4-Ig and the enhanced CD4-Ig (eCD4-Ig, the eCD4-Ig$^{Q40A,mim2}$ variant) (see Gardner et al., Nature, 519: 87-91 (2015)) were included for comparison. eCD4-Ig is a sCD4-Fc fusion protein with a CCR5-mimicking sulfopeptide fused to the C terminus of Fc. Efficient tyrosine sulfation of the peptide is required for potent HIV-1 neutralization so eCD4-Ig was produced by co-transfection of 293T cells with a plasmid encoding human TPST2 to promote addition of the sulfate moiety onto tyrosine residues in Gardner et al., Nature, 519: 87-91 (2015)). eCD4-Ig was produced in the same way (the modified protein designated eCD4-Ig-TPST2) and the 4Dm2m variants (LSEV constructs) were compared to both eCD4-Ig-TPST2 and the unmodified eCD4-Ig. eCD4-Ig had similar yield with CD4-Ig and 4Dm2m while co-transfection of 293FS cells with human TPST2-encoding plasmid resulted in a drastic decrease (by up to 10-fold) of eCD4-Ig-TPST2 expression.

Figure 11A:
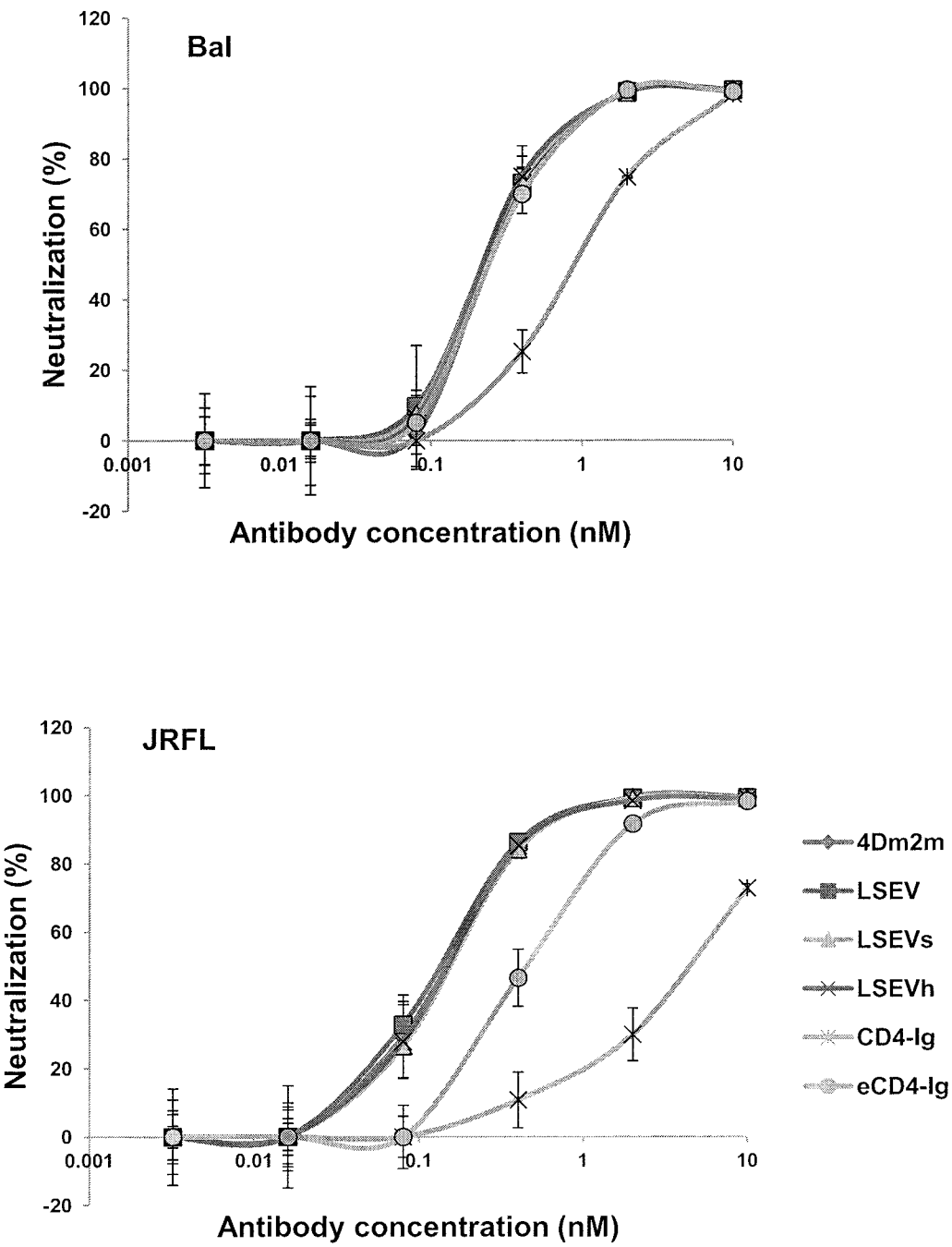
FIGS. 11A-B are graphs demonstrating the HIV-1 neutralizing activity of 4Dm2m variants (LSEV constructs) compared with eCD4-Ig (A) and eCD4-Ig-TPST2 (B). Bal and JRFL are two R5-tropic HIV-1 primary isolates from clade B. Viruses pseudotyped with HIV-1 Envs were produced in 293T cells and the assay was performed in duplicate with HOS-CD4-CCR5 cells as target cells.
Figure 11B:
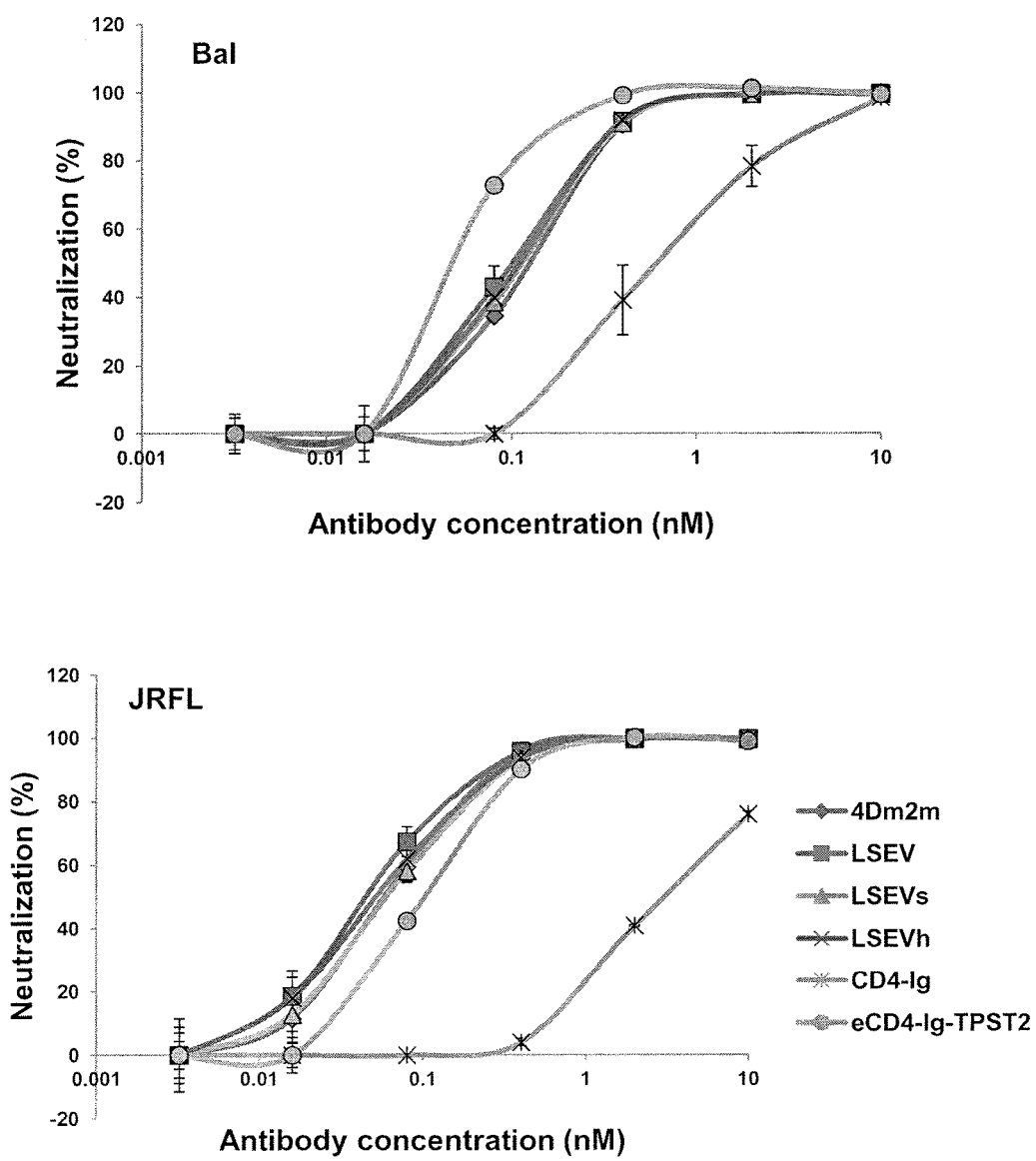

In a neutralization assay with two clade-B R5-tropic HIV-1 primary isolates (Bal and JRFL), we found that none of the engineering approaches apparently diminished the neutralizing activity of 4Dm2m (see FIGS. 11A-B). The 4Dm2m variants (LSEV constructs) and eCD4-Ig were equally potent against the tier-1 isolate Bal while the former neutralized the tier-2 isolate JRFL several-fold better than the latter (see FIG. 11A). As expected, eCD4-Ig-TPST2 showed an increased potency, about two-fold higher than that of the 4Dm2m variants (LSEV constructs) when Bal was tested; however, it was still less potent than the 4Dm2m variants (LSEV constructs) in neutralizing JRFL (see FIG. 11B). 4Dm2m and eCD4-Ig-TPST2 neutralized both isolates much more efficiently than CD-Ig.

The aggregation propensities of the proteins were evaluated by DLS. Because eCD4-Ig-TPST2 had very low yield and easily precipitated, eCD4-Ig was used in the DLS analysis and in the following animal study for pharmacokinetics. eCD4-Ig also began to precipitate when it was concentrated to 1 mg ml$^{-1}$ and above. Therefore, eCD4-Ig was tested at a concentration of 1 mg ml$^{-1}$ while all other proteins were analyzed at 5 mg ml$^{-1}$ in PBS (pH 7.4). All proteins were stored at −80° C. and slowly thawed on ice before measurement.

Results showed that after the freeze-thaw cycle, large precipitates were observed with eCD4-Ig and the supernatant recovered from high-speed centrifugation contained large particles (diameters, 100-200 nm) at about 10% of total particles. In contrast, all other protein solutions remained clear and no precipitates were observed after the treatment. The particles of 4Dm2m variants (LSEV constructs) were predominantly small (diameters, 13-15 nm) while a small percentage of the CD4-Ig particles were large. After incubation at 37° C. for one and three days, eCD4-Ig still precipitated but large soluble particles were not observed by DLS after the precipitates were removed; the protein was not prone to aggregate at 4'C. All other samples appeared to be stable throughout 7 days of incubation at both 4 and 37° C.

Example 7

This example demonstrates the improved pharmacokinetics of 4Dm2m variants (LSEV constructs).

Figure 12:
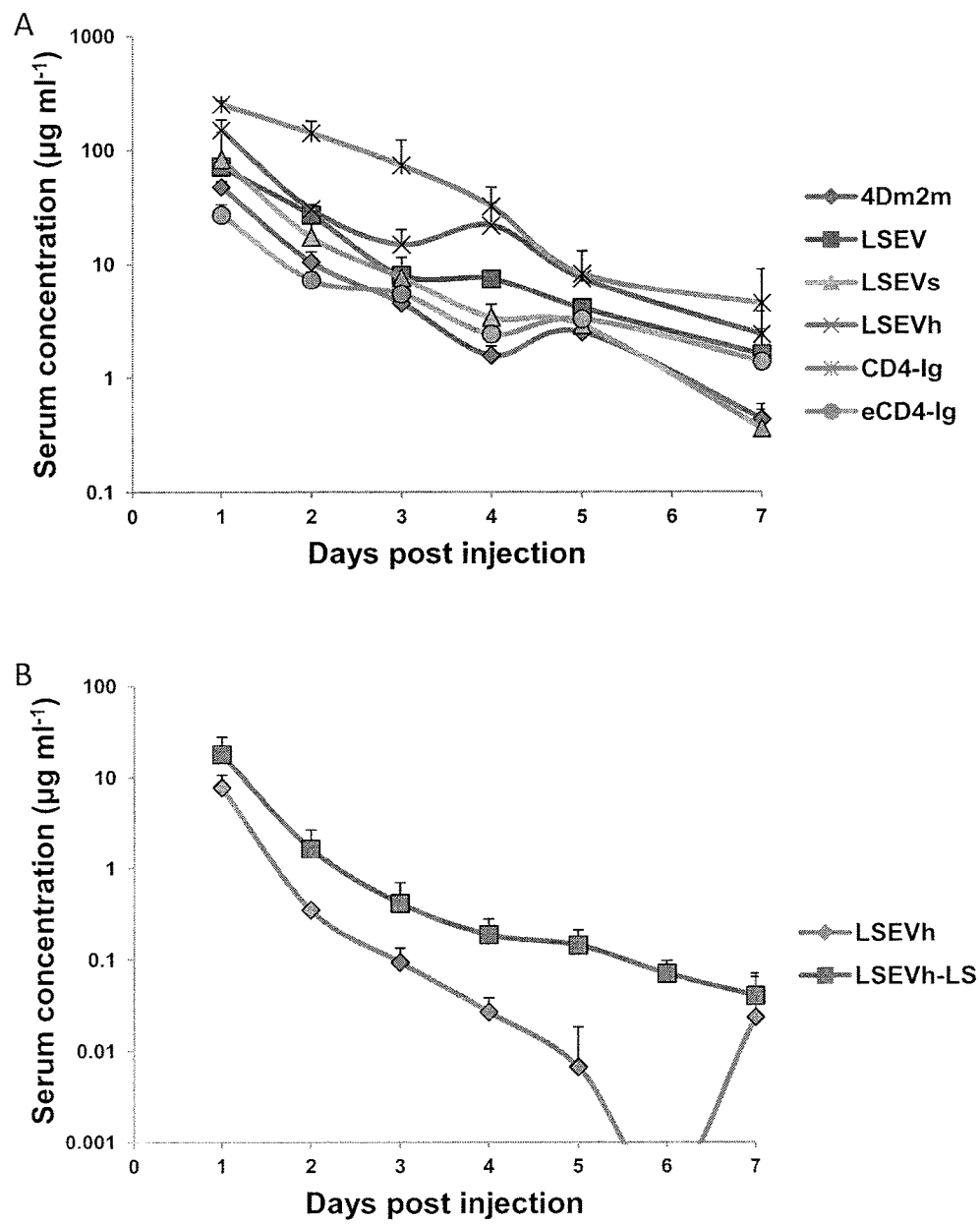
FIGS. 12A-B are graphs demonstrating pharmacokinetics of 4Dm2m variants (LSEV constructs) in C57BL/6 mice (A) and human FcRn transgenic mice (B). Animals were intravenously injected with either 0.1 (for eCD4-1g) or 1 mg (for all others) proteins on day 0. Plasma was collected by submandibular bleeding daily thereafter and serum concentrations of proteins were measured by ELISA. Each group included two or three animals. Plotted data are means+ standard deviations.

The pharmacokinetics of 4Dm2m variants (LSEV constructs) and the control proteins eCD4-Ig and CD4-Ig were tested in C57BL/6 mice. Each mouse received either 0.1 (for eCD4-Ig) or 1 mg (for all others) proteins and blood samples were collected daily (except on day 6) for 7 days. As expected, the new 4Dm2m variants (LSEV constructs) had higher, although insignificantly (P>0.1, Student t test), serum concentrations than 4Dm2m at almost all time points with LSEVh showing the slowest clearance (see FIG. 12A). The level of CD4-Ig declined at a lower rate than that of LSEVh within the first three days but CD4-Ig clearance was accelerated thereafter. In contrast, the serum concentrations of LSEVh reached a relatively steady state between day 3-5. Overall and statistically (P=0.32, Student t test), CD4-Ig did not appear to have more favorable pharmacokinetics than LSEVh. Albeit with 10-fold lower input, eCD4-Ig showed a similar level of retention with 4Dm2m.

Example 8

This example demonstrates that the pharmacokinetics of LSEVh could be improved by engineering Fc to enhance FcRn binding.

Figure 13:
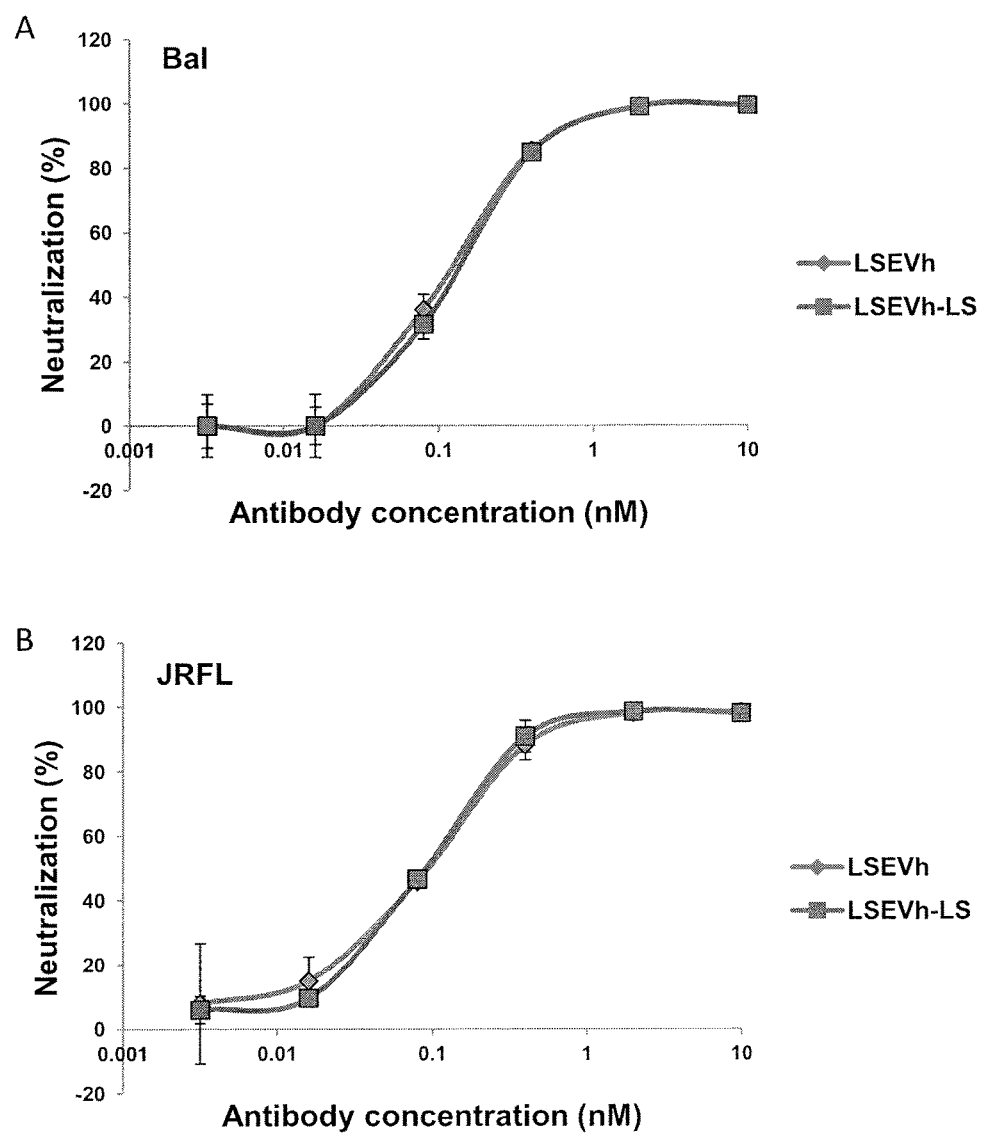
FIGS. 13A-B are graphs demonstrating the HIV-1 neutralizing activity of LSEVh-LS compared with LSEVh. Bal (A) and JRFL (B) are two R5-tropic HIV-1 primary isolates from clade B. Viruses pseudotyped with HIV-1 Envs were produced in 293T cells and the assay was performed in duplicate with HOS-CD4-CCR5 cells as target cells.

To further improve the pharmacokinetics of LSEVh, the M428L/N434S double mutations were introduced into Fc, which have been found to largely increase antibody binding to FcRn and half-lives in vivo (see Ko et al., Nature, 514: 642-5 (2014); and Zalevsky et al., Nat. Biotechnol., 28: 157-9 (2010)). SPR analysis revealed that at pH 6.0, LSEVh bound to a recombinant human FcRn with an affinity of 290 nM while no binding was detected at pH 7.4. The LSEVh mutant (LSEVh-LS) with M428L/N434S mutations also exhibited pH-dependent interaction with FcRn and showed an affinity (27 nM) about 11-fold higher than that of LSEVh at pH 6.0. The mutagenesis did not affect FcγRIIIa binding and HIV-1 neutralization (see FIGS. 13A-B).

The effects of the Fc engineering on the pharmacokinetics of LSEVh-LS were evaluated in human FcRn transgenic mice. LSEVh-LS showed several-fold higher serum concentrations than LSEVh at almost all time points (see FIG.

12B). LSEVh was undetectable on day 6. Interestingly, LSEVh appeared to be cleared much more rapidly in the FcRn transgenic mice than in the C57BL/6 mice (see FIGS. 12A-B).

Example 9

This example demonstrates the establishment of a CHO stable cell line producing defucosylated LSEVh-LS.

Previous studies have demonstrated that Fc-mediated effector functions of broadly neutralizing antibodies (bnAbs), particularly antibody-dependent cellular cytotoxicity (ADCC), contribute substantially to their ability to control HIV-1 infection in vivo and that bnAbs, when defucosylated, are much more efficient than fully fucosylated antibodies in killing HIV-1-infected cells through ADCC (see Lewis et al., *Immunology*, 142: 46-57 (2014); Bournazos et al., *Cell*, 158: 1243-53 (2014); and Moldt et al., *J. Virol.*, 86: 189-96 (2012)).

Figure 14:
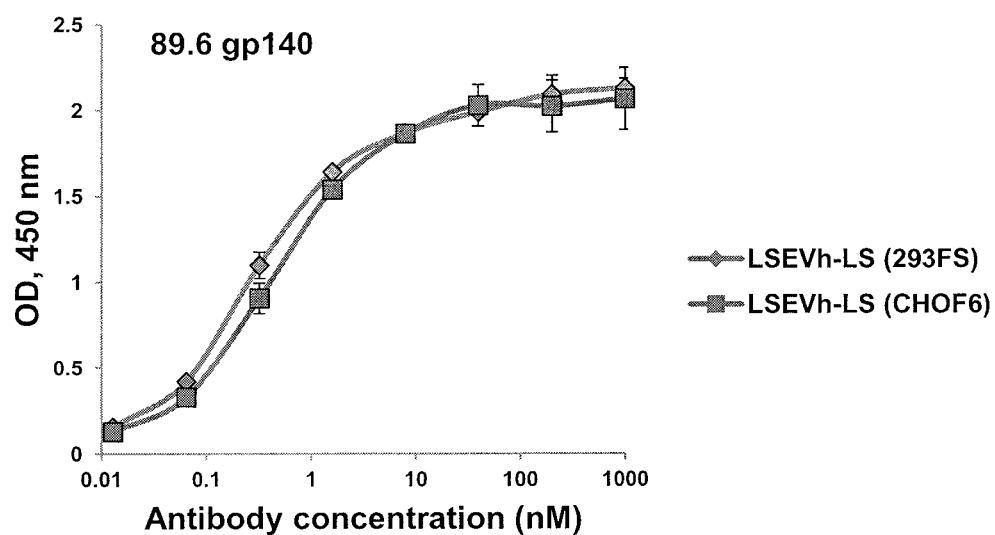
FIGS. 14A-B are graphs showing the characterization of LSEVh-LS (CHOF6). The graphs show ELISA binding to the HIV-1 Env gp140$_{89.6}$ (A) and FcγRIIIa (B). Antigens were coated on 96-well plates at a concentration of 2 μg ml$^{-1}$. Bound 4Dm2m variants (LSEV constructs) were detected by HRP-conjugated goat anti-human IgG (Fc-specific) antibody.
Figure 14:
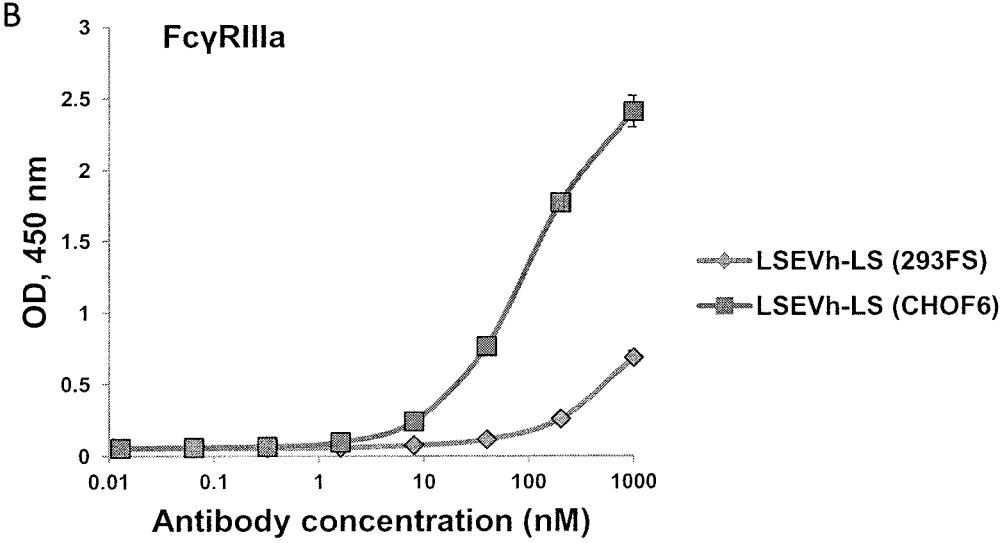

To test whether defucosylation could have an effect on the fusion proteins, a CHO cell line stably expressing defucosylated LSEVh-LS was generated, which was designated LSEVh-LS (CHOF6), with yield of approximately 400 mg liter$^{-1}$. LSEVh-LS (CHOF6) bound to the HIV-1 Env gp140$_{89.6}$ equally well compared to LSEVh-LS (293FS) (the fully fucosylated LSEVh-LS produced in 293FS cells) while showing much higher binding to FcγRIIIa than the latter (see FIGS. 14A-B). High-resolution mass spectrometry confirmed that the heavy chain of LSEVh-LS (CHOF6) was defucosylated.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A construct comprising
two fusion proteins of A-(optional linker)-C(Formula III), and
two fusion proteins of B-(optional linker)-D-(optional linker)-E-(optional linker)-B (Formula II),
wherein A is an antibody or antibody fragment and B is a single domain CD4,
wherein C is a modified immunoglobulin light chain constant region comprising one of SEQ ID NOs: 29-34,
wherein D is modified immunoglobulin heavy chain constant region comprising one of SEQ ID NOs: 22-27, and
wherein E is an Fc region or portion thereof.

2. The construct of claim 1, wherein the single domain CD4 comprises SEQ ID NO: 1 or SEQ ID NO: 2.

3. The construct of claim 1, wherein the antibody or antibody fragment binds to an HIV envelope glycoprotein.

4. The construct of claim 1, wherein the antibody or antibody fragment is an engineered antibody domain (eAd).

5. The construct of claim 4, wherein the eAd comprises an amino acid sequence selected from the group consisting of SEQ ID NOs: 10-14.

6. The construct of claim 1, wherein the Fc region or portion thereof comprises SEQ ID NO: 5, SEQ ID NO: 6, or SEQ ID NO: 51.

7. The construct of claim 1, wherein the Fc region or portion thereof is defucosylated.

8. The construct of claim 1, wherein the optional linker comprises one or more $G_4S$ motifs or a portion of human IgG1 hinge.

9. The construct of claim 8, wherein the optional linker comprises the amino acid sequence of SEQ ID NO: 7, SEQ ID NO: 8, SEQ ID NO: 9, SEQ ID NO: 35, or SEQ ID NO: 36.

10. The construct of claim 1, wherein the modified immunoglobulin light chain constant region comprises SEQ ID NO: 31.

11. The construct of claim 1, wherein the modified immunoglobulin heavy chain constant region comprises SEQ ID NO: 24.

12. The construct of claim 1, wherein
(a) the fusion protein of Formula III comprises SEQ ID NO: 40 and the fusion protein of Formula II comprises SEQ ID NO: 39;
(b) the fusion protein of Formula III comprises SEQ ID NO: 42 and the fusion protein of Formula II comprises SEQ ID NO: 41;
(c) the fusion protein of Formula III comprises SEQ ID NO: 44 and the fusion protein of Formula II comprises SEQ ID NO: 43;
(d) the fusion protein of Formula III comprises SEQ ID NO: 46 and the fusion protein of Formula II comprises SEQ ID NO: 45;
(e) the fusion protein of Formula III comprises SEQ ID NO: 48 and the fusion protein of Formula II comprises SEQ ID NO: 47; or
(f) the fusion protein of Formula III comprises SEQ ID NO: 50 and the fusion protein of Formula II comprises SEQ ID NO: 49.

13. A composition comprising the construct of claim 1 and a carrier.

14. A conjugate comprising (a) the construct of claim 1 and (b) a cytotoxic agent.

15. The conjugate of claim 14, wherein the cytotoxic agent is a toxin.

16. A composition comprising the conjugate of claim 14 and a carrier.

* * * * *